(12) United States Patent
Miyamoto et al.

(10) Patent No.: US 9,957,402 B2
(45) Date of Patent: May 1, 2018

(54) COMPOUND, ACTIVE ENERGY RAY CURABLE COMPOSITION, CURED ARTICLE THEREOF, PRINTING INK, AND INKJET RECORDING INK

(71) Applicant: DIC Corporation, Tokyo (JP)

(72) Inventors: Masanori Miyamoto, Sakura (JP); Youichi Tanimoto, Kitaadachi-gun (JP); Sei Yamamoto, Tokyo (JP); Azusa Yogo, Tokyo (JP); Akihiro Kondou, Sakura (JP); Tomokazu Yamada, Tokyo (JP)

(73) Assignee: DIC CORPORATION, Tokyo (JP)

( * ) Notice: Subject to any disclaimer, the term of this patent is extended or adjusted under 35 U.S.C. 154(b) by 0 days. days.

(21) Appl. No.: 15/309,954

(22) PCT Filed: May 12, 2015

(86) PCT No.: PCT/JP2015/063603
§ 371 (c)(1),
(2) Date: Nov. 9, 2016

(87) PCT Pub. No.: WO2015/174402
PCT Pub. Date: Nov. 19, 2015

(65) Prior Publication Data
US 2017/0152391 A1    Jun. 1, 2017

(30) Foreign Application Priority Data

May 15, 2014  (JP) .................................. 2014-101411
Nov. 10, 2014  (JP) .................................. 2014-227964

(51) Int. Cl.

| | | |
|---|---|---|
| C08F 2/46 | (2006.01) | |
| C08F 2/50 | (2006.01) | |
| C08G 61/04 | (2006.01) | |
| C09D 11/38 | (2014.01) | |
| B41J 2/01 | (2006.01) | |
| C07C 237/34 | (2006.01) | |
| C09D 11/101 | (2014.01) | |
| B41M 5/50 | (2006.01) | |

(Continued)

(52) U.S. Cl.
CPC ................. *C09D 11/38* (2013.01); *B41J 2/01* (2013.01); *B41M 5/50* (2013.01); *C07C 237/20* (2013.01); *C07C 237/34* (2013.01); *C07D 295/033* (2013.01); *C07D 295/192* (2013.01); *C09D 11/101* (2013.01); *C09D 11/107* (2013.01)

(58) Field of Classification Search
USPC .................. 522/33, 6, 71, 189, 184, 1; 520/1
See application file for complete search history.

(56) References Cited

U.S. PATENT DOCUMENTS 4,992,547 A    2/1991  Berner et al.
5,077,402 A    12/1991  Desobry et al.
(Continued)

FOREIGN PATENT DOCUMENTS

| CN | 102020728 A | 4/2011 |
|---|---|---|
| JP | 60-84248 A | 5/1985 |
| JP | 63-264560 A | 11/1988 |
| JP | 2-151822 A | 6/1990 |
| JP | 10-291969 A | 11/1998 |
| JP | 2005-505615 A | 2/2005 |
| JP | 2007-525573 A | 9/2007 |
| JP | 2008-519760 A | 6/2008 |
| JP | 2012-7071 A | 1/2012 |
| WO | 2011-001928 A1 | 1/2011 |

OTHER PUBLICATIONS

International Search Report dated Aug. 11, 2015, issued in counterpart International Application No. PCT/JP2015/063603 (2 pages).

*Primary Examiner* — Jessica Whiteley
(74) *Attorney, Agent, or Firm* — Westerman, Hattori, Daniels & Adrian, LLP

(57) ABSTRACT

A compound obtained through Michael addition reaction of an α-aminoacetophenone skeleton-containing compound (I) represented by the following general formula (1) and a reactive compound (II) having a function as a Michael acceptor is used as a photopolymerization initiator. In the general formula (1), $R_1$ represents an aliphatic group, $R_2$ to $R_3$ each independently represent an aliphatic group, etc., $R_4$ to $R_7$ each independently represent a hydrogen atom, $X_1$ represents a single bond or a C1-6 alkylene group, $X_2$ represents a carbonyl group, $Y_1$ and $Y_2$ represent a group represented by the following general formula (2). However, when $Y_1$ and $Y_2$ both have a structure represented by the general formula (2), $X_5$ in at least one of them is —NH—. In the general formula (2), $X_3$ and $X_4$ each independently represent a linear or branched alkylene group having 2 to 6 carbon atoms, $X_5$ represents a single bond, —O— or —NH—.

(1)

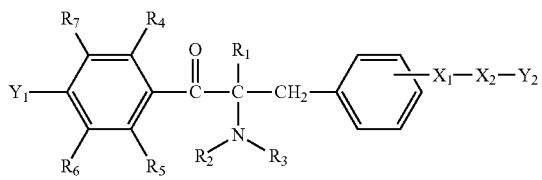

(2)

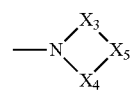

13 Claims, 4 Drawing Sheets

(51) Int. Cl.
  *C07C 237/20* (2006.01)
  *C07D 295/192* (2006.01)
  *C09D 11/107* (2014.01)
  *C07D 295/033* (2006.01)

(56) References Cited

U.S. PATENT DOCUMENTS

| | | | |
|---|---|---|---|
| 6,022,906 | A | 2/2000 | Ohwa et al. |
| 7,166,647 | B2 | 1/2007 | Herlihy et al. |
| 7,612,122 | B2 | 11/2009 | Herlihy et al. |
| 8,674,089 | B2 | 3/2014 | Fabian et al. |
| 2008/0021126 | A1* | 1/2008 | Dietliker .................. C08F 2/50 522/34 |

* cited by examiner

COMPOUND, ACTIVE ENERGY RAY CURABLE COMPOSITION, CURED ARTICLE THEREOF, PRINTING INK, AND INKJET RECORDING INK

TECHNICAL FIELD

The present invention relates to a compound having a group with a Michael addition donor functionality, a compound useful as an intermediate thereof, a photopolymerization initiator containing the compound having a group with a Michael addition donor functionality, and an active energy ray curable composition containing the photopolymerization initiator.

BACKGROUND ART

Heretofore, from the viewpoint of high production efficiency, curing energy cost reduction and VOC reduction, an active energy ray curable system has been widely applied. Above all, a UV-curable system is the mainstream since the facility introduction cost is low and the installation area can be small as compared with any other active ray curable system.

The photopolymerization initiator that is the essential component in the UV-curable system remains in a cured product as it is therein the photopolymerization itself or as a decomposed matter thereof, differing from a reactive monomer that is to form a polymer form after curing to be fixed in a cured film. Almost all photopolymerization initiators that are distributed in the art are low-molecular-weight compounds, and therefore the remaining photopolymerization initiator itself or decomposed matter thereof is also a low-molecular-weight substance, and heretofore this is a cause of an offensive odor.

Further, recently, it has become pointed out that the remaining material may migrate toward the substance that is kept in contact with the cured product, and in particular, in a UV-curable ink for use in food-wrapping prints, the remaining material may migrate toward the back surface of the print that is in direct contact with food, and the regulation on migration of a photopolymerization initiator is being severer year by year.

For this, there has been made a trial of reducing migration by making a photopolymerization initiator have a reactive group to fix it in a cured film.

For example, in PTL 1 and PTL 2, there are disclosed oligomer-type photopolymerization initiators having plural initiator groups in the molecule. The method disclosed in these publications is effective for reducing odor and migration by oligomerizing the photopolymerization initiator. However, against the recent regulations, the effect is still insufficient.

PTL 3 discloses a UV-curable resin obtained through Michael addition reaction of a photopolymerization initiator having an α-aminoacetophenone structure and a polyfunctional acrylate. According to the method disclosed in PTL 3, a reactive group is introduced into the photopolymerization initiator group so as to fix the photopolymerization initiator group in a cured coating film to thereby greatly reduce the odor of the photopolymerization initiator in the cured film. However, the photopolymerization initiator disclosed in PTL 3 is somewhat poor in photopolymerization performance and especially in use that requires a curing rate such as in a UV-curable ink or the like, there occurs a problem of curing insufficiency.

CITATION LIST

Patent Literature

PTL 1: JP-T 2005-505615
PTL 2: JP-T 2008-519760
PTL 3: WO11/001928

SUMMARY OF INVENTION

Technical Problem

The present invention is to provide a compound capable of reducing migration after curing and excellent in curability as a photopolymerization initiator, a photopolymerization initiator using the compound, and an active energy ray curable composition containing the photopolymerization initiator.

Solution to Problem

As a result of assiduous studies, the present inventors have found that a Michael addition reaction product obtained through Michael addition reaction of a specific compound having a function as a Michael addition donor and a reactive compound having a function as a Michael acceptor can solve the above-mentioned problems.

Specifically, the present invention relates to a Michael addition reaction product obtained through Michael addition reaction of a compound having a function as a Michael addition donor represented by the following general formula (1), and a reactive compound having a function as a Michael acceptor.

[Chem. 1]

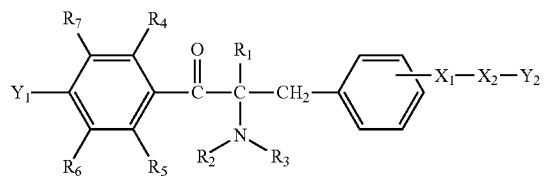

(1)

(In the general formula (1), $R_1$ represents an aliphatic group or an aryl group, $R_2$ to $R_3$ each independently represent an aliphatic group or an aryl group, $R_2$ and $R_3$ may together form a ring, $R_4$ to $R_7$ each independently represent a hydrogen atom, an aliphatic group or an aryl group, $X_1$ represents a single bond or a linear or branched alkylene group having 1 to 6 carbon atoms, $X_2$ represents a carbonyl group or a thiocarbonyl group, $Y_1$ represents a group represented by the following general formula (2), general formula (3) or general formula (4), and $Y_2$ represents a group represented by the following general formula (2) or general formula (4), provided that when $Y_1$ and $Y_2$ both have a structure represented by the general formula (2), $X_5$ in at least one of them is —NH—.)

[Chem. 2]

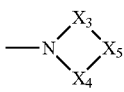

General Formula (2)

(In the general formula (2), $X_3$ and $X_4$ each independently represent a linear or branched alkylene or oxyalkylene group having 2 to 6 carbon atoms, and $X_5$ represents —O— or —NH—.)

[Chem. 3]

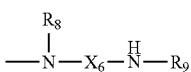

General Formula (3)

(In the general formula (3), $X_6$ represents a substituted or unsubstituted, linear or branched alkylene or oxyalkylene group having 2 to 6 carbon atoms, and $R_8$ and $R_9$ each independently represent an aliphatic group or an aryl group.)

[Chem. 4]

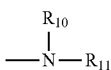

General Formula (4)

(In the general formula (4), $R_{10}$ and $R_{11}$ each independently represent an aliphatic group or an aryl group.)

The present invention also relates to a compound represented by the following formula (1'):

[Chem. 5]

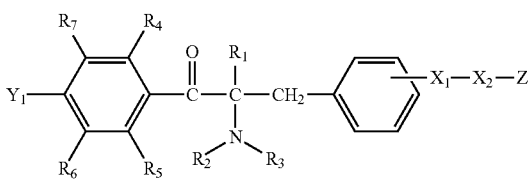

(1')

(In the general formula (1'), $R_1$ represents an aliphatic group or an aryl group, $R_2$ to $R_3$ each independently represent an aliphatic group or an aryl group, $R_2$ and $R_3$ may together form a ring, $R_4$ to $R_7$ each independently represent a hydrogen atom, an aliphatic group or an optionally substituted aryl group, $X_1$ represents a single bond or a linear or branched alkylene group having 1 to 6 carbon atoms, $X_2$ represents a carbonyl group or a thiocarbonyl group, and $Y_1$ represents a group represented by the following general formula (2'), general formula (3') or general formula (4'), and Z represents a hydroxyl group or a thiol group.)

[Chem. 6]

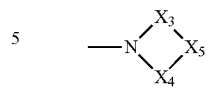

General Formula (2')

(In the general formula (2'), $X_3$ to $X_4$ each independently represent a linear or branched alkylene or oxyalkylene group having 2 to 6 carbon atoms, and $X_5$ represents —O— or —NH—.)

[Chem. 7]

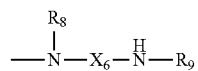

General Formula (3')

(In the general formula (3'), $X_6$ represents a substituted or unsubstituted, linear or branched alkylene or oxyalkylene group having 2 to 6 carbon atoms, and $R_8$ and $R_9$ each independently represent an aliphatic group or an aryl group.)

[Chem. 8]

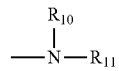

General Formula (4')

(In the general formula (4'), $R_{10}$ and $R_{11}$ each independently represent an aliphatic group or an aryl group.)

The present invention also relates to a photopolymerization initiator containing the above-mentioned Michael addition reaction product.

The present invention also relates to an active energy ray curable composition containing the photopolymerization initiator.

The present invention also relates to a cured product produced by curing the active energy ray curable composition.

The present invention also relates to an active energy ray curable printing ink containing the active energy ray curable composition.

The present invention also relates to an active energy ray curable inkjet recording ink containing the active energy ray curable composition.

Advantageous Effects of Invention

According to the present invention, there can be obtained a photopolymerization initiator capable of reducing migration and excellent in curability. Using it, there can also be obtained an active energy ray curable composition having a rapid curing rate.

DESCRIPTION OF EMBODIMENTS

Figure 1:
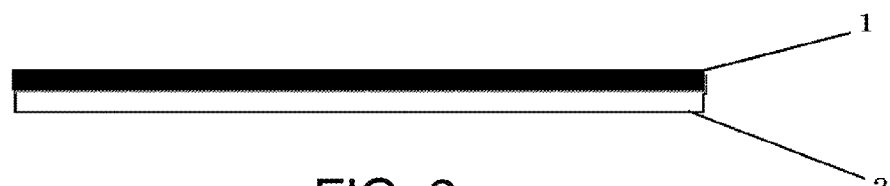
FIG. 1 This is a view showing a print produced by UV-irradiating a print prepared by drawing thereon an active energy ray curable composition of the present invention as an ink, followed by curing the ink layer.

Compound Functioning as Michael Addition Donor Represented by General Formula (1)

The Michael addition reaction product of the present invention is, as described above, one obtained through Michael addition reaction of an α-aminoacetophenone skeleton-containing compound (I) having a function as a Michael addition donor represented by the above-mentioned general formula (1), and a reactive compound (II) having a function as a Michael acceptor.

Here, the α-aminoacetophenone skeleton-containing compound (I) having a function as a Michael addition donor for use in the present invention is one having a functional group with a Michael addition donor function as typified by a secondary amino group such as a piperazinyl group, a methylamino group, an ethylamino group, a benzylamino group, and the like, in the molecular structure, and is concretely represented by the following general formula (1).

[Chem. 9]

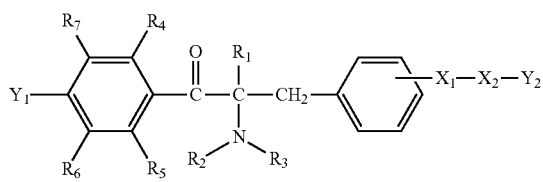

General Formula (1)

(In the general formula (1), $R_1$ represents an aliphatic group or an aryl group, $R_2$ to $R_3$ each independently represent an aliphatic group or an aryl group, $R_2$ and $R_3$ may together form a ring, $R_4$ to $R_7$ each independently represent a hydrogen atom, an aliphatic group or an aryl group, $X_1$ represents a single bond or a linear or branched alkylene group having 1 to 6 carbon atoms, $X_2$ represents a carbonyl group or a thiocarbonyl group, $Y_1$ represents a group represented by the following general formula (2), general formula (3) or general formula (4), and $Y_2$ represents a group represented by the following general formula (2) or general formula (3). However, when $Y_1$ and $Y_2$ both have a structure represented by the general formula (2), and $X_5$ in at least one of them is —NH—.)

[Chem. 10]

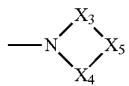

General Formula (2)

(In the general formula (2), $X_3$ and $X_4$ each independently represent a linear or branched alkylene or oxyalkylene group having 2 to 6 carbon atoms, $X_5$ represents a single bond, —O— or —NH—.)

[Chem. 11]

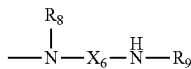

General Formula (3)

(In the general formula (3), $X_6$ represents a substituted or unsubstituted, linear or branched alkylene or oxyalkylene group having 2 to 6 carbon atoms, and $R_8$ and $R_9$ each independently represent an aliphatic group or an aryl group.)

[Chem. 12]

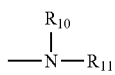

General Formula (4)

(In the general formula (4), $R_{10}$ and $R_{11}$ each independently represent an aliphatic group or an aryl group.)

Here, the aliphatic group constituting $R_1$ to $R_7$ in the general formula (1) includes an alkyl group, an alkenyl group, an alkynyl group.

Here, the alkyl group is, for example, any of a linear, branched or cyclic alkyl group having 1 to 18 carbon atoms. Specifically, for example, there are mentioned a linear or branched alkyl group such as a methyl group, an ethyl group, a propyl group, an n-butyl group, a t-butyl group, an s-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an isopropyl group, a sec-butyl group, an isobutyl group, a tert-butyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramaethylpentyl group, an isodecyl group, a 1-methylundecyl group, a 1,1,3,3,5,5-hexamethylhexyl group, a dodecyl group, a tetradecyl group, an octadecyl group, etc.; and a cycloalkyl group such as a cyclopentyl group, a cyclohexyl group, a cyclopentyl group, etc.

As the alkenyl group, there are mentioned an alkenyl group such as a propenyl group, an allyl group, a butenyl group such as a 2-butenyl group, a 3-butenyl group or an isobutenyl group, as well as an n-2,4-pentadienyl group, etc.

The alkynyl group includes an ethynyl group, a 1-propynyl group, a 1-butynyl group, a trimethylsilylethynyl group, etc.

Among these aliphatic groups, in particular, a linear alkyl group having 1 to 12 carbon atoms, a branched alkyl group having 3 to 12 carbon atoms, and a cyclic alkyl group having 5 to 10 carbon atoms are more preferred.

The aliphatic group may further have a substituent on the carbon atom therein, and the substituent includes those containing a monovalent non-metallic atom except a hydrogen atom.

Specifically, for example, there are mentioned a halogen atom (—F, —Br, —Cl, —I), a hydroxyl group, an alkoxy group, an aryloxy group, a mercapto group, an alkyl thio group, an arylthio group, an alkyldithio group, an aryldithio group, an amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N, N-diarylcarbamoyloxy group, an N-alkyl-N-arylcarbamoyloxy group, an alkylsulfoxy group, an arylsulfoxy group, an acylthio group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, a carboxyl group, an alkoxycarbonyl group, an aryloxycarbonyl group, a carbamoyl group, an N-alkylcarbamoyl group, an N-dialkylcarbamoyl group, an N-arylcarbamoyl, group, an N,N-diarylcarbamoyl group, an N-alkyl-N-arylcarbamoyl group, an alkylsulfinyl group, an arylsulfinyl group, an alkylsulfonyl group, an arylsulfonyl group, a sulfo group (—$SO_3H$) and a conjugated base group thereof (referred to as a sulfonate group), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N, N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, a phosphono group (—$PO_3H_2$) and a conjugated base group thereof (referred to as a phosphonate group), a dialkylphosphono group (—$PO_3(alkyl)_2$) (where alkyl means an alkyl group, and the same shall apply hereinunder), a diarylphosphono group (—$PO_3(aryl)_2$) (where aryl means an aryl group, and the same shall apply hereinunder), an alkylarylphosphono group (—$PO_3(alkyl)(aryl)$), a monoalkylphosphono group (—$PO_3H(alkyl)$) and a conjugated base group thereof (referred to as an alkylphosphonate group), a monoarylphosphono group (—$PO_3H(aryl)$) and a conjugated base group thereof (referred to as an arylphosphonate group), a phosphonoxy group (—$OPO_3H_2$) and a conjugated base group thereof (referred to as a phosphonatoxy group), a dialkylphosphonoxy group (—$OPO_3H(alkyl)_2$) a diarylphosphonoxy group (—$OPO_3(aryl)_2$), an alkylarylphosphonoxy group (—$OPO_3(alkyl)(aryl)$), a monoalkylphosphonoxy group (—$OPO_3H(alkyl)$) and a conjugated base group thereof (referred to as an alkylphosphonatoxy group), a monoarylphosphonoxy group (—$OPO_3H(aryl)$) and a conjugated base group thereof (referred to as an arylphosphonatoxy group), a cyano group, a nitro group, an aryl group, an alkenyl group, an alkynyl group, a heterocyclic group, a silyl group, etc.

Specific examples of the alkyl group in these substituents include the above-mentioned alkyl groups. Specific examples of the aryl group in the substituents include a phenyl group, a biphenyl group, a naphthyl group, a tolyl group, a xylyl group, a mesityl group, a cumenyl group, a chlorophenyl group, a bromophenyl group, a chloromethylphenyl group, a hydroxyphenyl group, a methoxyphenyl group, an ethoxyphenyl group, a phenoxyphenyl group, an acetoxyphenyl group, a benzoyloxyphenyl group, a methylthiophenyl group, a phenylthiophenyl group, a methylaminophenyl, group, a dimethylaminophenyl group, an acetylaminophenyl group, a carboxyphenyl group, a methoxycarbonylphenyl group, an ethoxyphenylcarbonyl group, a phenoxycarbonylphenyl group, an N-phenylcarbamoylphenyl group, a cyanophenyl group, a sulfophenyl group, a sulfonatophenyl group, a phosphonophenyl group, a phosphonatophenyl group, etc.

Examples of the alkenyl group in the substituents include a vinyl group, a 1-propenyl group, a 1-butenyl group, a cinnamyl group, a 2-chloro-1-ethenyl group, etc.

Examples of the alkenyl group in the substituents include an ethynyl group, a 1-propynyl group, a 1-butynyl group, a trimethylsilylethynyl group, etc.

Next, the aryl group constituting $R_1$ to $R_7$ in the general formula (1) includes those formed of 1 to 3 benzene rings to be a condensed ring, and those formed of a benzene ring and a 5-membered unsaturated ring to be a condensed ring. Specifically, for example, there are mentioned a phenyl group, a methoxyphenyl group, an ethoxyphenyl group, a fluorophenyl group, a chiorophenyl group, a bromophenyl group, a tolyl group, a xylyl group, a naphthyl group, a benzyl group, an α-methylbenzyl group, an α,α-dimethylbenzyl group, a phenethyl group, a naphthyl group, an anthryl group, a phenanthryl group, an indenyl, group, an acenaphtenyl group, a fluorenyl group. Among these, a phenyl group and a naphthyl group are more preferred.

The aryl group may have a substituent containing a monovalent nonmetallic atomic group except a hydrogen atom, as a substituent on the ring-forming carbon atom of the aryl group. Here, preferred examples of the substituent include the above-mentioned alkyl groups as well as those shown hereinabove as the substituent in the alkyl group.

Preferred examples of the aryl group having a substituent include a biphenyl group, a tolyl group, a xylyl group, a mesityl group, a cumenyl group, a chlorophenyl group, a bromophenyl group, a fluorophenyl group, a chloromethylphenyl group, a trifluoromethylphenyl group, a hydroxyphenyl group, a methoxyphenyl group, a methoxyethoxyphenyl group, an allyloxyphenyl group, a phenoxphenyl group, a methylthiophenyl group, a tolylthiophenyl group, an ethylaminophenyl group, a diethylaminophenyl group, a morpholinophenyl group, an acetyloxyphenyl group, a benzoyloxyphenyl group, an N-cyclohexylcarbamoyloxyphenyl group, an N-phenylcarbamoyloxyphenyl group, an acetylaminophenyl group, an N-methylbenzoylaminophenyl group, a carboxyphenyl group, a methoxycarbonylphenyl group, an allyloxycarbonylphenyl group, a chlorophenoxycarbonylphenyl group, a carbamoylphenyl group, an N-methylcarbamoylphenyl group, an N,N-dipropylcarbamoylphenyl group, an N-(methoxyphenyl)carbamoylphenyl group, an N-methyl-N-(sulfophenyl)carbamoylphenyl group, a sulfophenyl group, a sulfonatophenyl group, a sulfamoylphenyl group, an N-ethylsulfamoylphenyl group, an N,N-dipropylsulfamoylphenyl group, an N-tolylsulfamoylphenyl group, an N-methyl-N-(phosphonophenyl)sulfamoylphenyl group, a phosphonophenyl group, a phosphonatophenyl group, a diethylphosphonophenyl group, a diphenylphosphonophenyl group, a methylphosphonophenyl group, a methylphosphonatoaphenyl group, a tolylphosphonophenyl group, a tolylphosphonatophenyl group, an allylphenyl group, a 1-propenylmethylphenyl group, a 2-butenylphenyl group, a 2-methylalylphenyl group, a 2-methylpropenylphenyl group, a 2-propynylphenyl group, a 2-butynylphenyl group, a 3-butynylphenyl group, etc.

In the present invention, specifically, $R_1$ is preferably a linear alkyl group having 1 to 12 carbon atoms, from the viewpoint of easy availability of starting materials and of easy reaction control in production, and is more preferably a linear alkyl group having 1 to 6 carbon atoms.

Also specifically, $R_2$ to $R_3$ each are preferably a linear alkyl group having 1 to 12 carbon atoms, more preferably a linear alkyl group having 1 to 6 carbon atoms.

Also specifically, $R_4$ to $R_7$ each are preferably a hydrogen atom or a linear alkyl group having 1 to 6 carbon atoms.

In the general formula (1), $X_1$ represents a single bond, or a linear or branched alkylene group having 1 to 6 carbon atoms such as a methylene group, an ethylene group, a propylene group, etc. Here, as the substituent, there are mentioned those described hereinabove for the aliphatic group optionally having a substituent.

Next, in the general formula (1), $X_2$ represents a carbonyl group or a thiocarbonyl group.

In the general formula (1), $Y_1$ and $Y_2$ each independently represent a group represented by the general formula (2) or the general formula (3).

Here, the general formula (2) to constitute $Y_1$ and $Y_2$ is a structural formula shown below.

[Chem. 13]

General Formula (2)

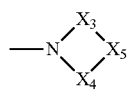

In the general formula (2), $X_3$ and $X_4$ each independently represent a linear or branched alkylene or oxyalkylene group having 2 to 6 carbon atoms, $X_5$ represents a single bond, —O— or —NH—. Specifically, $X_3$ and $X_4$ include linear or branched methylene group, ethylene group, propylene group, butylene group, oxymethylene group, oxypropylene group, oxybutylene group, etc.

Specifically, the structural part represented by the general formula (2) described in detail hereinabove includes the following structures.

[Chem. 14]

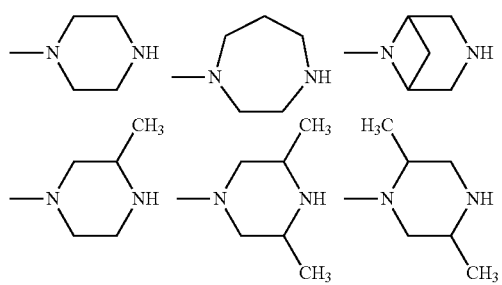

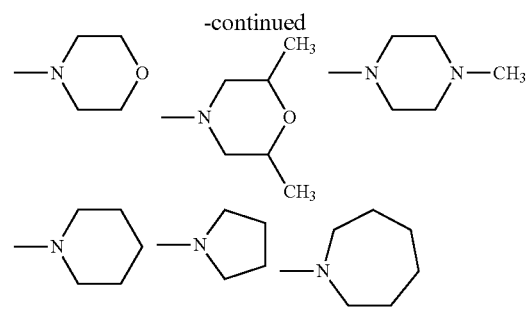

Next, the general formula (3) constituting $Y_1$ and $Y_2$ is represented by the following structural formula.

[Chem. 15]

General Formula (3)

Here, in the general formula (3), $X_6$ represents a substituted or unsubstituted, linear or branched alkylene or oxyalkylene group having 2 to 6 carbon atoms, and $R_8$ and $R_9$ each independently represent an aliphatic group or an aryl group. Here, specifically, the substituent in $X_6$ includes a linear or branched methylene group, a propylene group, a butylene group, an oxymethylene group, an oxypropylene group, an oxybutylene group, etc.

$R_8$ and $R_9$ each independently represent an aliphatic group or an aryl group. Here, as the aliphatic group and the aryl group, those to constitute the above-mentioned $R_1$ to $R_7$ are mentioned.

Next, the general formula (4) constituting $Y_1$ is one represented by the following structural formula.

[Chem. 16]

General Formula (4)

In the above general formula (4), $R_{10}$ and $R_{11}$ each independently represent an aliphatic group or an aryl group. As the aliphatic group and the aryl group, those exemplified as the aliphatic group and the aryl group to constitute the above-mentioned $R_1$ to $R_7$ are mentioned.

Here, in the present invention, in the case where $Y_1$ and $Y_2$ in the general formula (1) both have a structure represented by the general formula (2), $X_5$ in at least one of them is —NH—. With this, the α-aminoacetophenone skeleton-containing compound (I) can exhibit a Michael addition donor function.

Among those of the above-mentioned general formula (1), above all, compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group, and $Y_2$ is a piperazinyl group; compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is —CH(CH$_3$)—, $X_2$ is a carbonyl group, $Y_1$ is a piperazinyl group, and $Y_2$ is a piperazinyl group; compounds where $R_1$ is an ethyl group, $R_2$ is a 1-hexyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group, and $Y_2$ is a piperazinyl group; compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a morpholino group, and $Y_2$ is a piperazinyl group; and compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group, and $Y_2$ is a morpholino group are especially preferred.

Specifically, the compounds represented by the general formula (1) include compounds represented by the following structural formula (5) to structural formula (26).

Above all, from the viewpoint of high curability thereof, aminoacetophenone-type compounds having one cyclic secondary amino group such as a piperazinyl group or the like, that is, those of the structural formula (14), the structural formula (15), the structural formula (17) the structural formula (18), the structural formula (20), the structural formula (21), the structural formula (23), the structural formula (24) and the structural formula (25) are preferred, and in particular, those of the structural formula (14), the structural formula (15), the structural formula (23), and the structural formula (24) are preferred.

The compounds having the above-mentioned cyclic secondary amino group in $Y_1$ alone in the general formula (1) are preferred as the curability thereof are extremely high. Such compounds are those of the structural formula (23), the structural formula (24) and the structural formula (25).

Compounds having the above-mentioned cyclic secondary amino group in $Y_2$ only in the general formula (1) are especially preferred since the curability thereof is extremely high and since the ability thereof to take the cleaved product to be generated through active energy ray absorption in a polymer matrix could be promoted. Such compounds are the compounds of the structural formula (14), the structural formula (15), the structural formula (17), the structural formula (18), the structural formula (20) and the structural formula (21).

[Chem. 17]

(5)

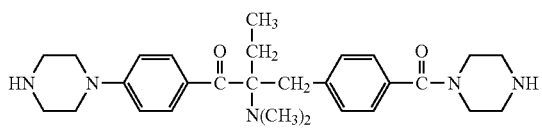

[Chem. 18]

(6)

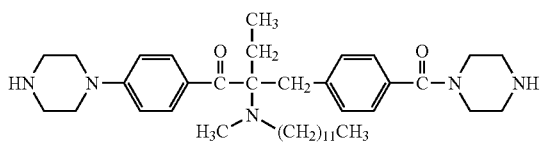

[Chem. 19]

(7)

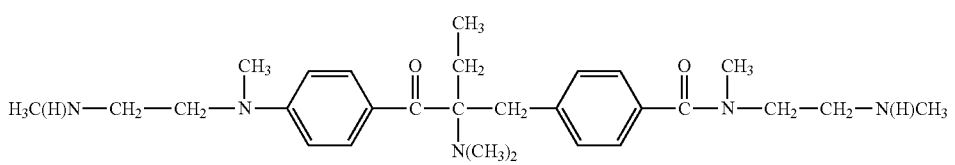

[Chem. 20]

(8)

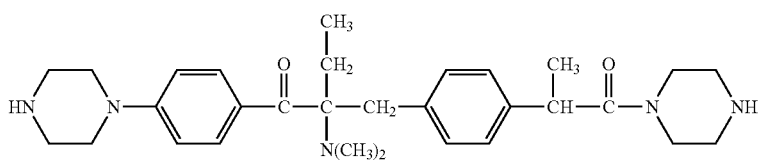

[Chem. 21]

(9)

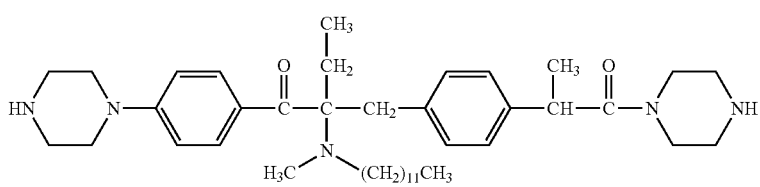

[Chem. 22]

(10)

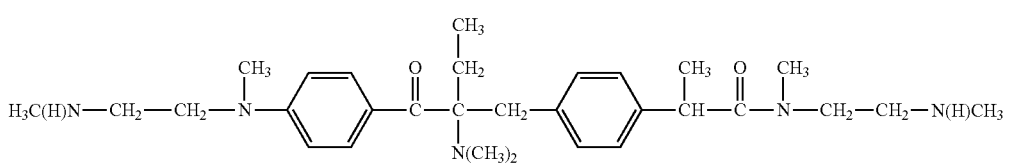

-continued
[Chem. 23]
(11)
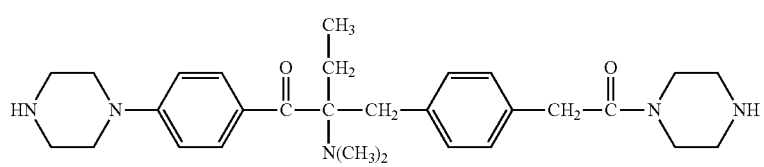
[Chem. 24]
(12)
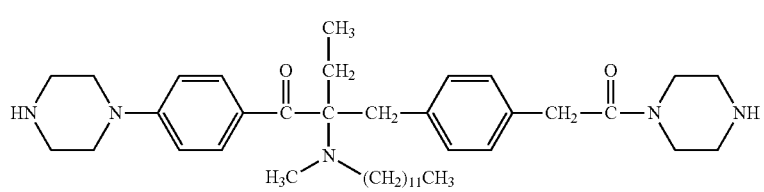
[Chem. 25]
(13)
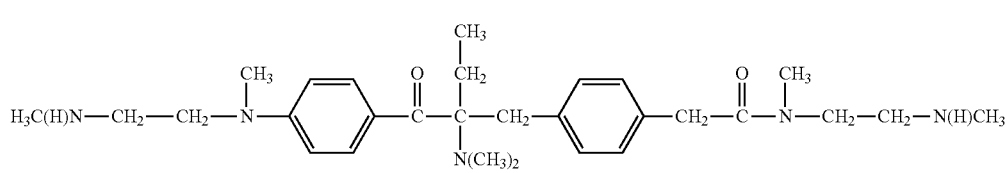
[Chem. 26] (14) [Chem. 27] (15)
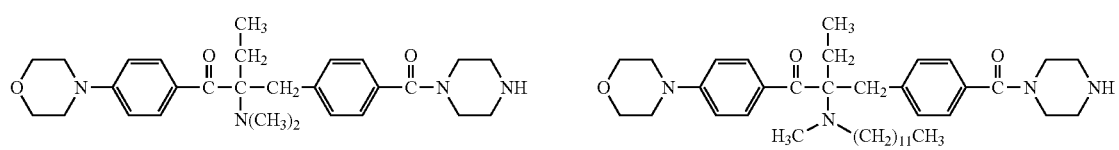
[Chem. 28]
(16)
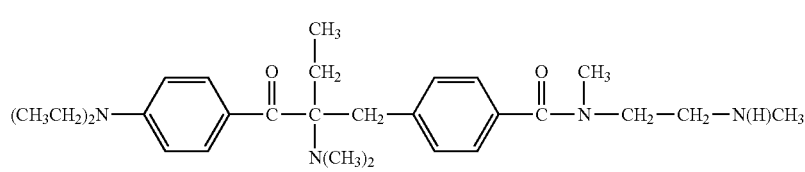
[Chem. 29]
(17)
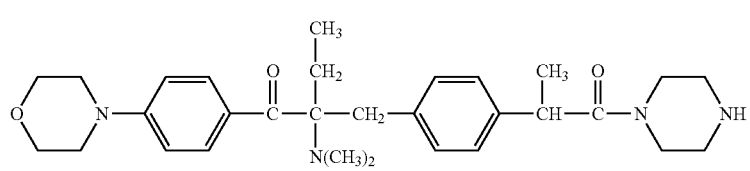
[Chem. 30]
(18)
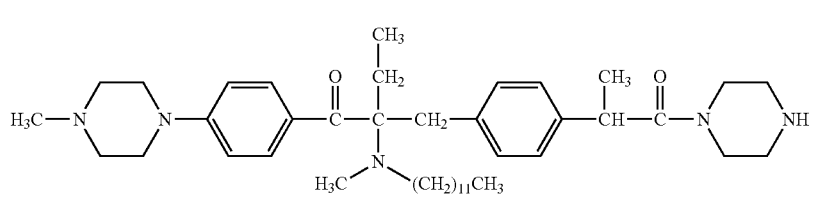

-continued
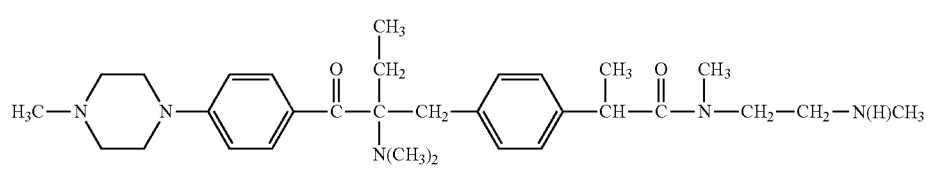
(19)
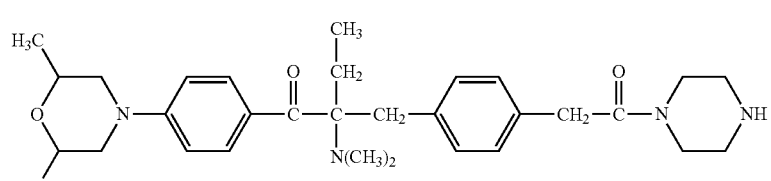
(20)
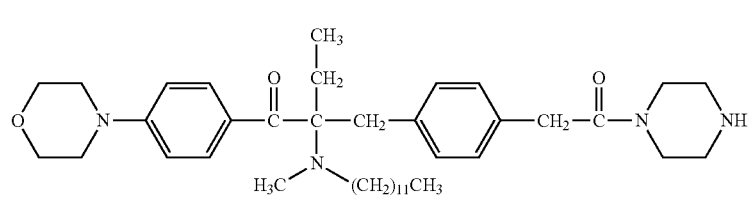
(21)
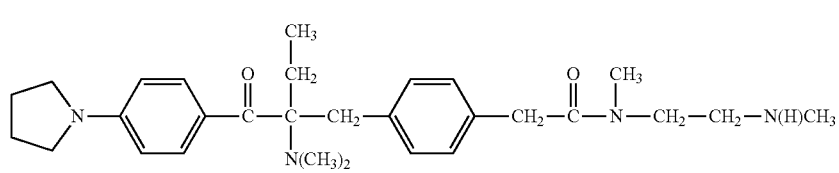
(22)
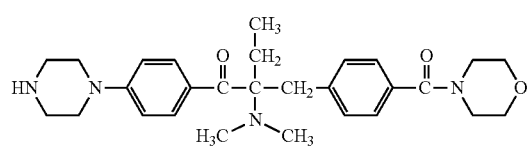
(23)
(24)
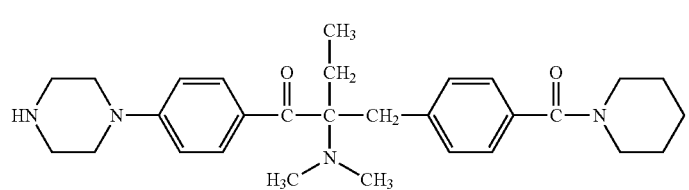
(25)
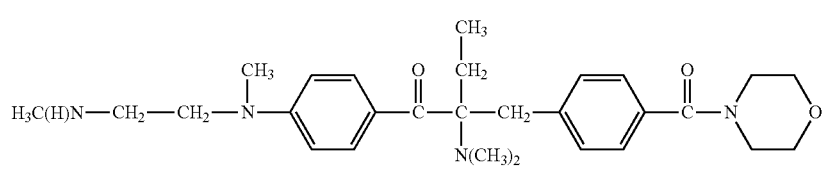
(26)

These α-aminoacetophenone skeleton-containing compounds (I) can be produced according to any of the following methods 1 to 3 depending on the difference in the process of introduction of $Y_1$— and $Y_2$— in the general formula (1).

(Method 1)

In the method 1, an alkylacetophenone having a halogen atom in the aromatic nucleus is reacted with a secondary amino group-containing compound ($Y_1$—H), then a bromine atom is introduced into the α-position of the carbonyl group, and thereafter this is reacted with a secondary monoamine compound ($HN(R_2)(R_3)$), and then with a benzyl bromide having a substituent (—X1-X2-OR) as a substituent on the aromatic nucleus. Here, R represents an alkyl group. Next, this is processed with an alkali to give a compound (A) that is an intermediate having a hydroxyl group (or a thiol group) at the terminal. Further, this is reacted with a secondary amino group-containing compound ($Y_2$—H) to give the intended product, α-aminoacetophenone skeleton-containing compound (I). In this case, in the reaction between the intermediate compound (A) and the secondary amino group-containing compound ($Y_2$—H)), where the secondary amino group-containing compound ($Y_2$—H) is an active hydrogen-having diamine compound, a method is employable, where one amino group of the compound is protected with an oxycarbonyl group or the like and the resultant protected compound is used in the reaction, and finally the product is treated with an acid to remove the protective group.

Method 1

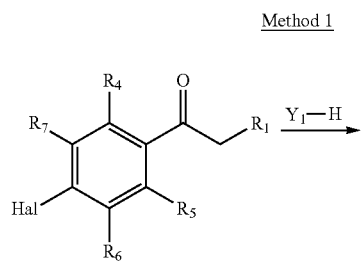

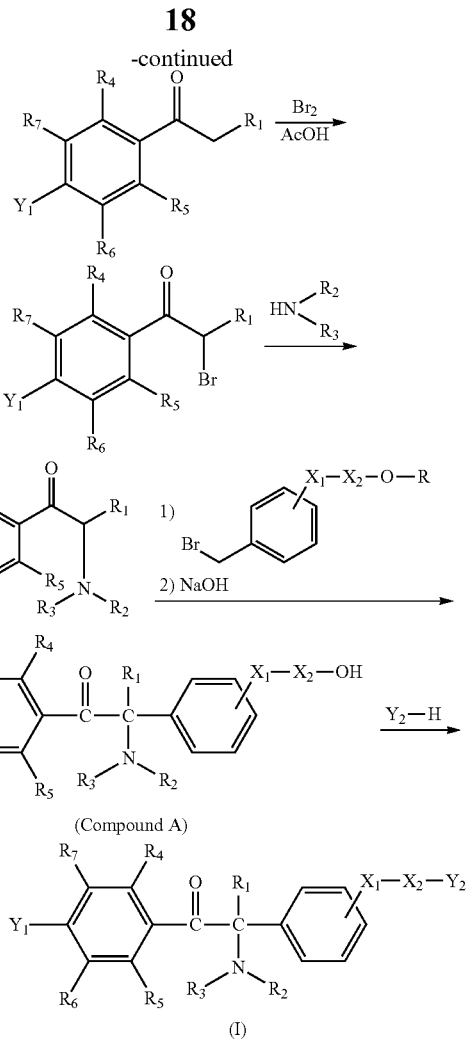

[Chem.39]

Regarding the above method 1, more specifically, an example of producing a compound represented by the above formula (14) is described according to the following reaction formula. (In the following structural formulae, C, CH and $CH_2$ are omitted, as the case may be)

[Chem.40]

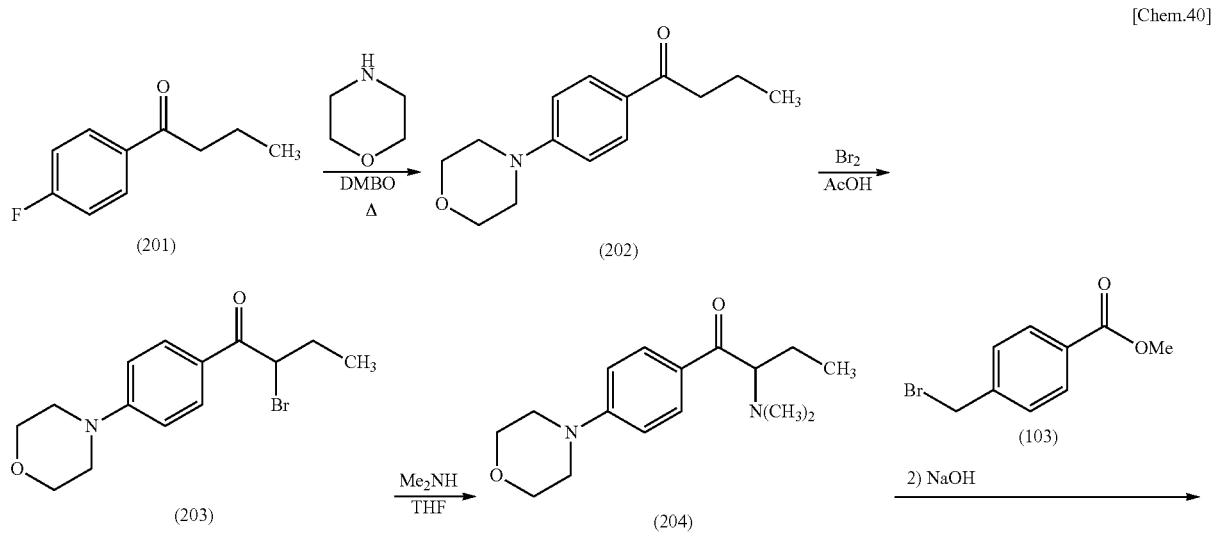

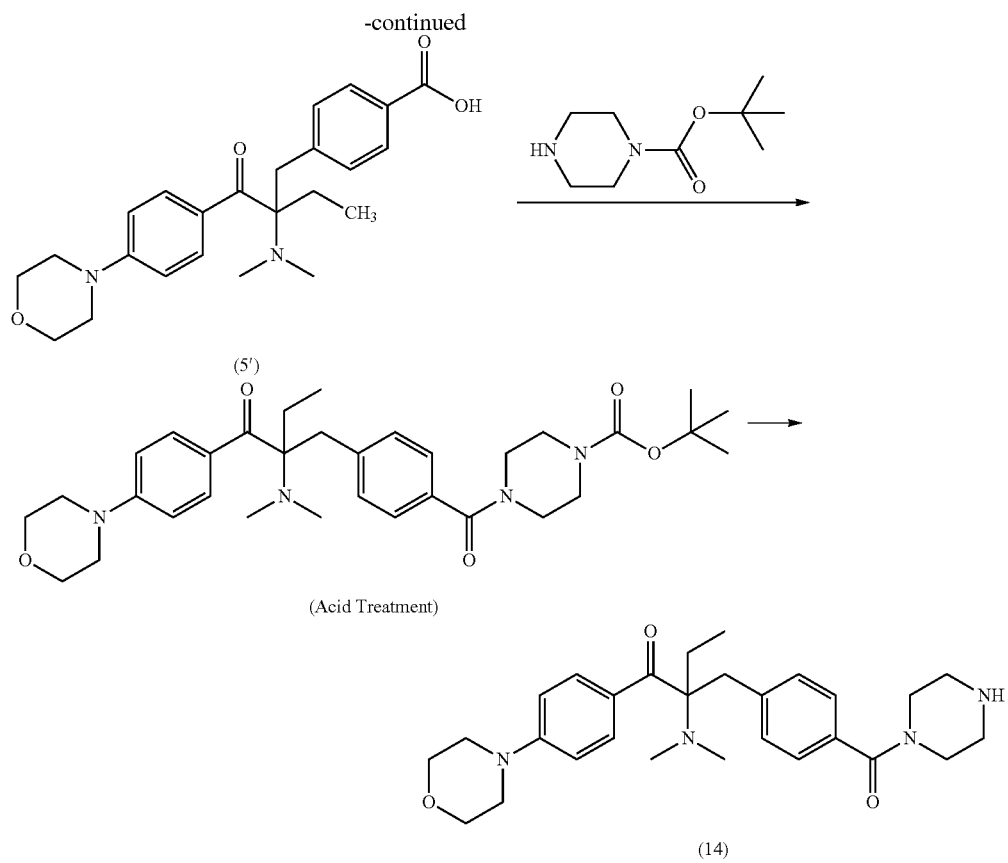

(Acid Treatment)

(14)

Specifically, morpholine is reacted with 4-fluorophenylbutanone to produce morpholinophenylbutanone (202), and then reacted with bromine to produce a bromo-morpholinophenylbutanone (203) in which a bromine atom is introduced into the α-positioned carbon atom of the carbonyl group. Next, this is substituted with dimethylamine to give a dimethylamino form (204), and is further reacted with a bromobenzyl derivative (103) having a substituent at the 4-position to be led to a quaternary ammonium chloride, and then subjected to 1,2-rearrengement reaction (Stevens rearrengement) with a base to give an α-aminoacetophenone skeleton-having intermediate (5'). Subsequently, through an active esterification using a cyclohexylcarbodiimide reagent or the like or through an acid chloride forming reaction using thionyl chloride or the like, this is reacted with a piperazine derivative, and then treated with an acid to produce the intended compound (14).

(Method 2)

In the method 2, a halogenobenzene and an acid halide are reacted to give an alkylacetophenone having a halogen atom on the α-carbon atom of the carbonyl group and having a halogen atom on the aromatic nucleus, and then this is reacted with a secondary monoamine compound (HN($R_2$)($R_3$)) and with a secondary amino group-containing compound ($Y_1$—H). Next, this is reacted with a benzyl bromide having a substituent (—$X_1$—$X_2$—OR) as a substituent on the aromatic nucleus (where R represents an alkyl group), and created with an alkali to give an intermediate compound (A) having a hydroxyl group (or a thiol group) at the terminal. Further, this is reacted with a secondary amino group-containing compound ($Y_2$—H) to give the intended product, α-aminoacetophenone skeleton-containing compound (I). In this case, in the reaction between the intermediate compound (A) and the secondary amino group-containing compound ($Y_2$—H), where the secondary amino group-containing compound ($Y_2$—H) is an active hydrogen-having diamine compound, a method is also employable like in the method 1, where one amino group of the compound is protected with an oxycarbonyl group or the like and the resultant protected compound is used in the reaction, and finally the product is treated with an acid to remove the protective group.

Method 2

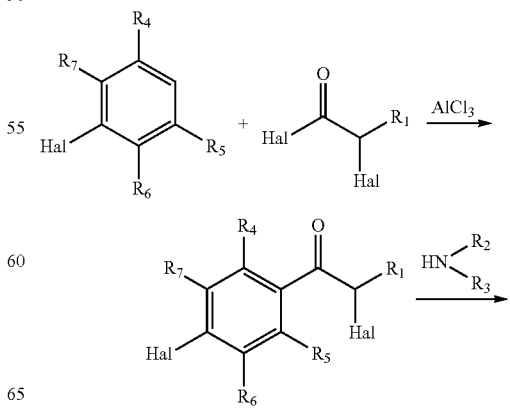

[Chem. 41]

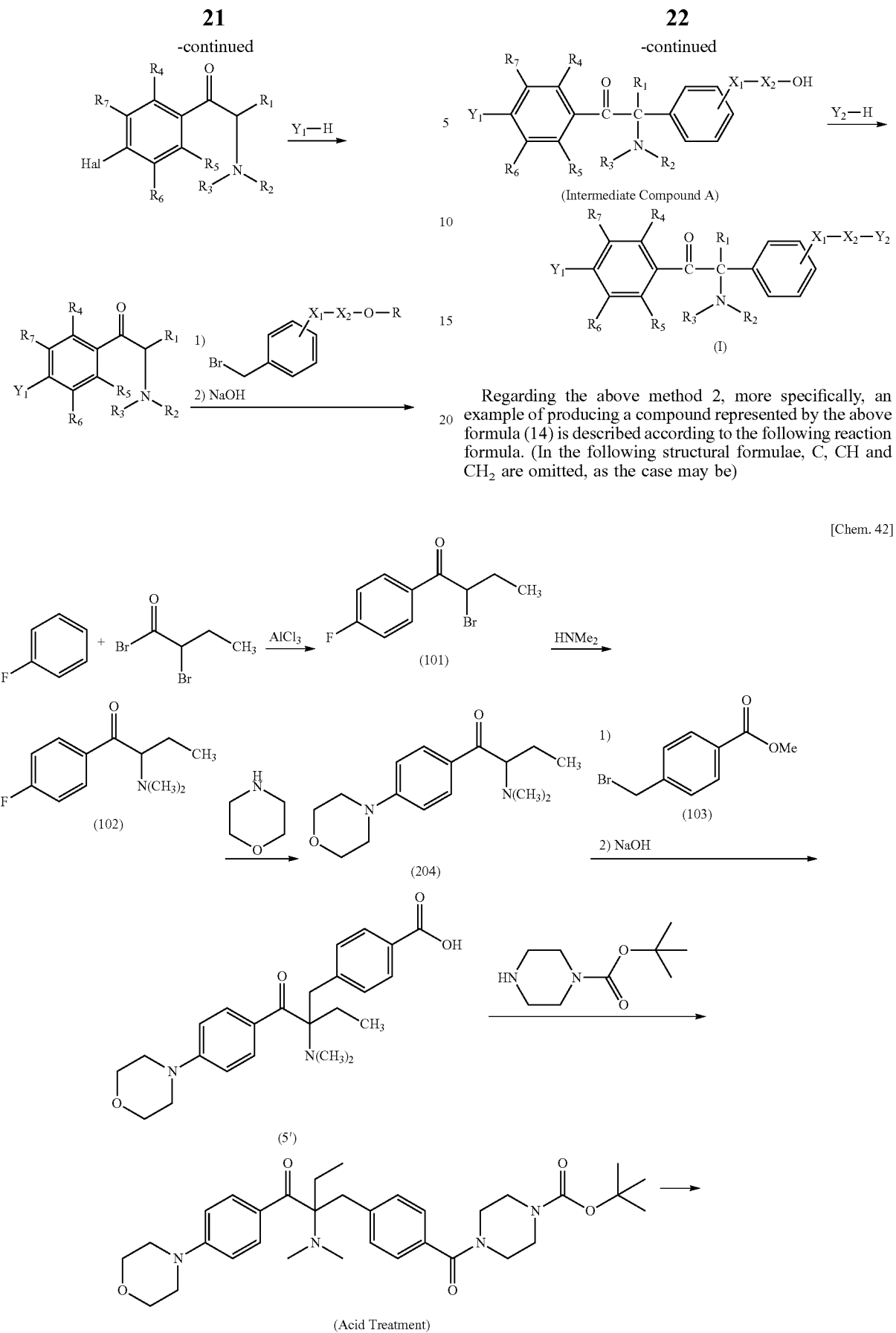
(Intermediate Compound A)
(I)
Regarding the above method 2, more specifically, an example of producing a compound represented by the above formula (14) is described according to the following reaction formula. (In the following structural formulae, C, CH and CH₂ are omitted, as the case may be)
[Chem. 42]

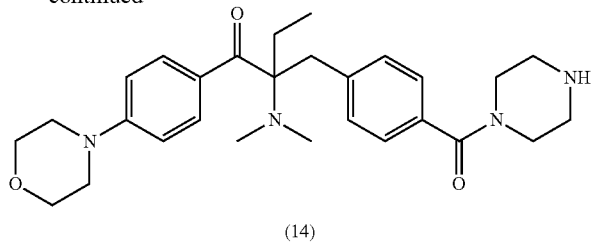

(14)

Specifically, fluorobenzene and 2-bromobutanoic acid bromide are acylated using anhydrous aluminum chloride, and the resultant acylated bromide form (101) is substituted with dimethylamine to give a dimethylamino form (102). Next, the dimethylamino form (102) is subjected to nucleophilic substitution at the 4-position on the aromatic ring, with a secondary amine, morpholine to give a 4-morpholinylphenylbutanone derivative (204), and is further reacted, with a bromobenzyl derivative (103) having a substituent such as an ester or the like at the para-position to be led to a quaternary ammonium chloride, and then subjected to 1,2-rearrangement reaction with a base to give an α-amino-acetophenone skeleton-having intermediate (5'). Subsequently, through an active esterification using a dicyclohexylcarbodiimide reagent or the like or through an acid chloride forming reaction using thionyl chloride or the like, this is reacted with a piperazine derivative, and then treated with an acid to produce the intended compound (14).

(Method 3)

In the method 3, a halogenobenzene and an acid halide compound are reacted to give an alkylacetophenone having a halogen atom on the α-carbon atom of the carbonyl group and having a halogen atom on the aromatic nucleus, and then reacted with a secondary monoamine compound ($HN(R_2)(R_3)$). Next, this is reacted with a benzyl bromide having a substituent ($-X_1-X_2-OR$) as a substituent on the aromatic nucleus (where R represents an alkyl group), and then treated with an alkali to give a compound having a hydroxyl group (or a thiol group) at the terminal, and this is reacted with a secondary amino group-containing compound ($Y_1-H$) and then with a secondary amino group-containing compound ($Y_2-H$) to produce the intended product, α-aminoacetophenone skeleton-containing compound (I).

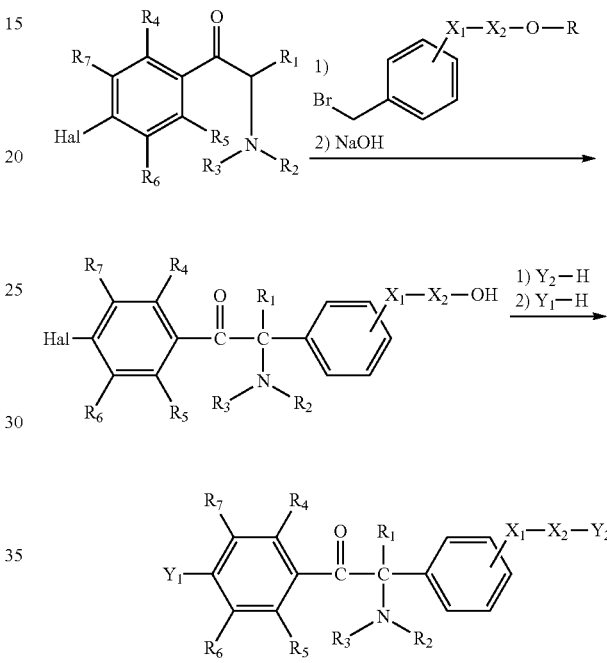

Regarding the above method 3, more specifically, an example of producing a compound represented by the above formula (5) is described according to the following reaction formula. (In the following structural formulae, C, CH and $CH_2$ are omitted, as the case may be)

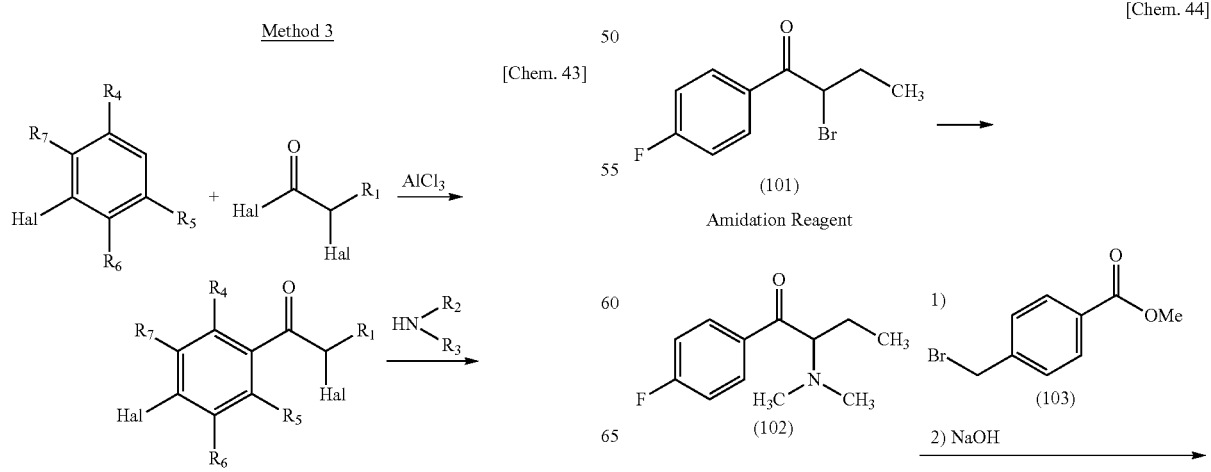

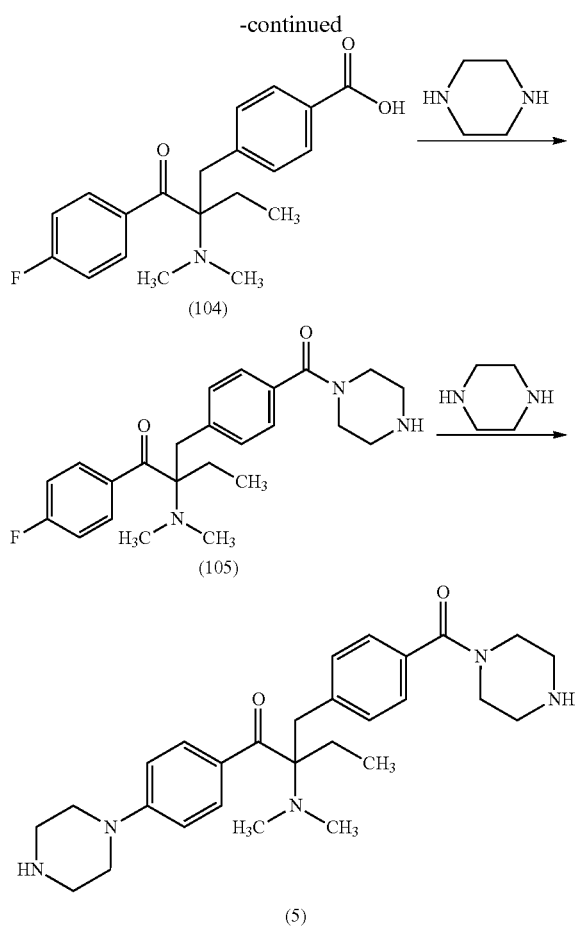

(104)

(105)

(5)

Specifically, a bromide (101) is substituted with dimethylamine to give a dimethylamino form (102), this is reacted with a bromobenzyl derivative (103) having a substituent at the 4-position to be led to a quaternary ammonium chloride, and then subjected to 1,2-rearrangement reaction (Stevens rearrangement) with a base to give an α-aminoacetophenone skeleton-having intermediate (104). Subsequently, through an active esterification or through an acid chloride forming reaction, this is reacted with an amine such as piperazine or the like to be led to an amidation form (105), and is further reacted with piperazine at 60° C. to 160° C. to produce the intended product, compound (5) where the piperazino group has a Michael addition donor functionality.

Here, in the reaction formulae of the above-mentioned methods 1 to 3, $R_1$ to $R_6$, $X_1$, $X_2$, $Y_1$ and $Y_2$ have the same meanings as in the above-mentioned general formula (1), and Hal represents a halogen atom such as a fluorine atom, a bromine atom, a chlorine atom, etc.

In the methods 1 to 3, the secondary monoamine compound ($HN(R_2)(R_3)$) includes dimethylamine, diethylamine, methylbutylamine, methyloctylamine, methyldodecylamine, ethylhexylamine, diethanolamine, 2,2'-diethoxydiethylamine, diisopropanolamine, morpholine, pyrrolidone, piperidine, N-methylpiperazine, 2,6-dimethylmorpholine, etc. The benzyl bromide compound having a substituent ($—X_1—X_2—OR$) on the aromatic nucleus includes, for example, methyl bromomethylbenzoate, methyl 2-[4-(bromomethyl)phenyl]propionate, ethyl 2-[4-(bromomethyl)phenyl]acetate, methyl bromomethylthiobenzoate, methyl 2-[4-(bromomethyl)phenyl]thiopropionate, etc.

Here, the intermediate in the method 1 and the method 2, the compound (A) in the present invention is, as described above, represented by the following general formula (1').

[Chem. 45]

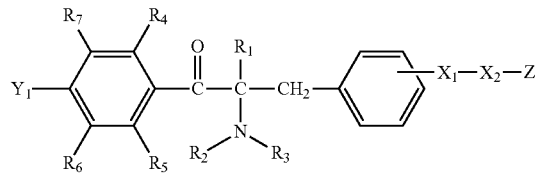

(1')

(In the general formula (1'), $R_1$ represents an aliphatic group or an aryl group, $R_2$ to $R_3$ each independently represent an aliphatic group or an aryl group, $R_2$ and $R_3$ may together form a ring, $R_4$ to $R_7$ each independently represent a hydrogen atom, an aliphatic group or an optionally substituted aryl group, $X_1$ represents a single bond or a linear or branched alkylene group having 1 to 6 carbon atoms, $X_2$ represents a carbonyl group or a thiocarbonyl group, $Y_1$ represents a group represented by the following general formula (2'), general formula (3') or general formula (4'), Z represents a hydroxyl group or a thiol group).

[Chem. 46]

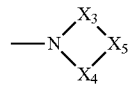

General Formula (2')

(In the general formula (2'), $X_3$ and $X_4$ each independently represent a linear or branched alkylene or oxyalkylene group having 2 to 6 carbon atoms, $X_5$ represents a single bond, —O— or —NH—.)

[Chem. 47]

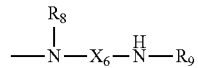

General Formula (3')

(In the general formula (3'), $X_6$ represents a substituted or unsubstituted, linear or branched alkylene or oxyalkylene group having 2 to 6 carbon atoms, and $R_8$ and $R_9$ each independently represent an aliphatic group or an aryl group.)

[Chem. 48]

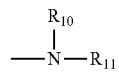

General Formula (4')

(In the general formula (4'), $R_{10}$ and $R_{11}$ each independently represent an aliphatic group or an aryl group.)

Here, $R_1$ to $R_7$ in the general formula (1') have the same meanings as in the above-mentioned general formula (1), and $X_1$ has the same meaning as that of $X_1$ in the general formula (1).

The general formula (2') constituting $Y_1$ in the general formula (1') is represented by the following structural formula.

[Chem. 49]

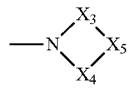

General Formula (2')

In the general formula (2'), $X_3$ and $X_4$ each independently represent a linear or branched alkylene or oxyalkylene group having 2 to 6 carbon atoms, $X_5$ represents a single bond, —O— or —NH—. Specifically, $X_3$ and $X_4$ include linear or branched methylene group, ethylene group, propylene group, butylene group, oxymethylene group, oxypropylene group, oxybutylene group, etc.

Specifically, the structural moiety represented by the general formula (2') described in detail hereinabove includes the following structures.

[Chem. 50]

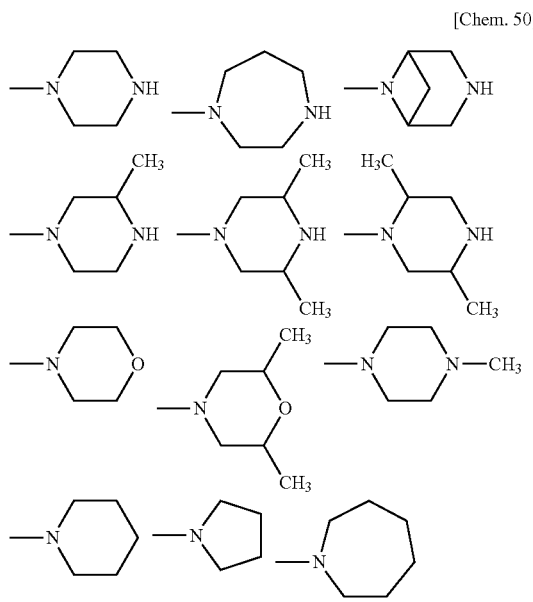

Next, the general formula (3') constituting $Y_1$ is represented by the following structural formula.

[Chem. 51]

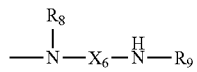

General Formula (3')

In the general formula (3'), $X_6$ represents a substituted or unsubstituted, linear or branched alkylene or oxyalkylene group having 2 to 6 carbon atoms, and $R_8$ and $R_9$ each independently represent an aliphatic group or an aryl group.

$X_6$ represents a linear or branched alkylene group or oxyalkylene group having 2 to 6 carbon atoms. Here, as the substituent, there are mentioned the substituents described hereinabove for the aliphatic group optionally having a substituent. Concretely, the substituent includes linear or branched methylene group, propylene group, butylene group, oxymethylene group, oxypropylene group, oxybutylene group, etc.

$R_8$ and $R_9$ each independently represent an aliphatic group or an aryl group optionally having a substituent. Here, as the aliphatic group and the aryl group, those described hereinabove are mentioned.

Next, the general formula (4') constituting $Y_1$ in the general formula (1') is one represented by the following structural formula.

[Chem. 52]

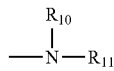

General Formula (4')

In the general formula (4'), $R_{10}$ and $R_{11}$ each independently represent an aliphatic group or an aryl group. As the aliphatic group or the aryl group, those exemplified hereinabove for the aliphatic group or the aryl group constituting $R_1$ to $R_7$ in the general formula (1) are mentioned.

Among those of the above-mentioned general formula (1'), above all, compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group, Z is a hydroxyl group; compounds where $R_1$ is an ethyl group. $R_2$ is a methyl group, $R_3$ is a methyl group, $R_4$ is hydrogen, $R_5$ is hydrogen, $R_6$ is hydrogen, $R_7$ is hydrogen, $X_1$ is —CH($CH_3$)—, $X_2$ is a carbonyl group, $Y_1$ is a piperazinyl group, and $Y_2$ is a piperazinyl group; compounds where $R_1$ is an ethyl group, $R_2$ is a 1-hexyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group and Z is a hydroxyl group; compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a morpholino group, and Z is a hydroxyl group; and compounds where $R_1$ is an ethyl group, $R_2$ is a methyl group, $R_3$ is a methyl group, $R_4$ is hydrogen, $R_5$ is hydrogen, $R_6$ is hydrogen, $R_7$ is hydrogen, $X_1$ is a single bond, $X_2$ is a carbonyl group, $Y_1$ is a piperazinyl group, and Z is a hydroxyl group are especially preferred.

Among the above-mentioned compounds (A), compounds of the following structural formula (5') to structural formula (14') are especially preferred as the starting materials for them are easily available.

[Chem. 53]

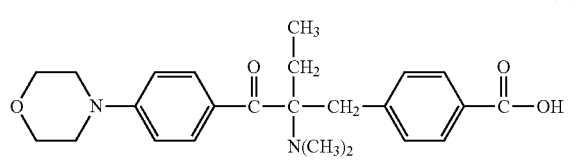

(5')

[Chem. 54]

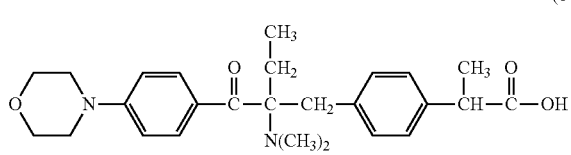
(6')

[Chem. 55]

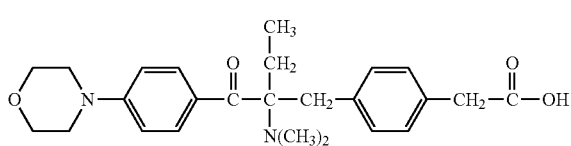
(7')

[Chem. 56]

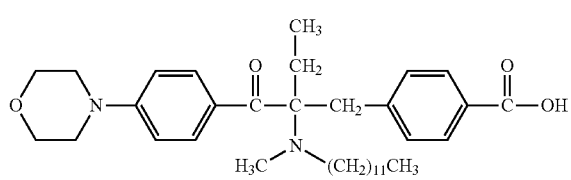
(8')

[Chem. 57]

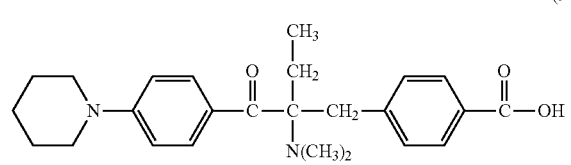
(9')

[Chem. 58]

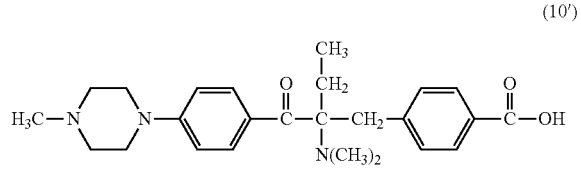
(10')

[Chem. 59]

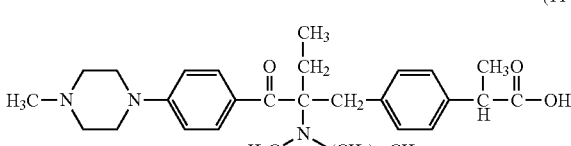
(11')

[Chem. 60]

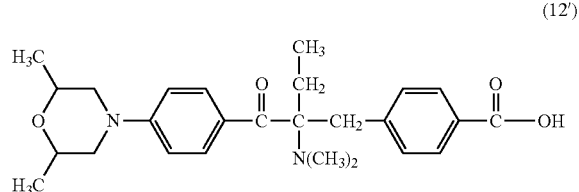
(12')

[Chem. 61]

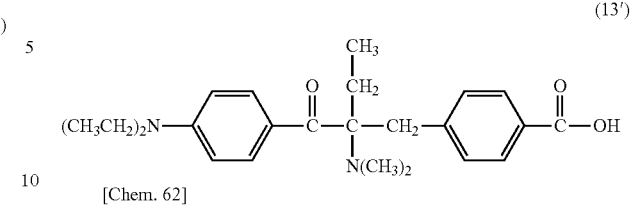
(13')

[Chem. 62]

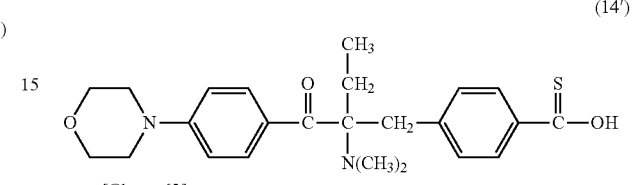
(14')

[Chem. 63]

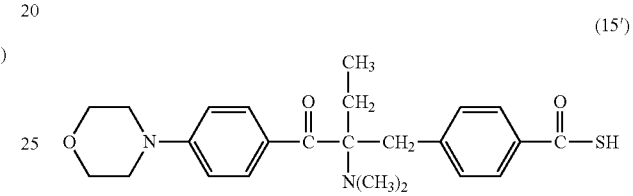
(15')

Among these structural formulae (5') to (15'), compounds represented by the formula (5') to (13') where the group represented by $X_2$—$Y_2$ is a carboxyl group are preferred as the starting materials for synthesizing them are easily available, and compounds represented by the formula (5'), the formula (6') and the formula (7') are especially preferred.

The compounds (A) represented by the general formula (1') can be produced as intermediates in the production method of the method 1 or the method 2 mentioned hereinabove.

The α-aminoacetophenone skeleton-containing compound (I) that functions as a Michael addition donor represented by the general formula (1) described in detail hereinabove has a Michael addition donor functionality, and can react with the compound (II) having a function as a Michael acceptor through Michael addition reaction to give a Michael addition reaction product.

In the present invention, in the case where a reactive compound having a reactive group that contributes toward curing through photoirradiation (hereinafter abbreviated as "photocuring group") is used as the compound (II) having a function as a Michael acceptor, the Michael addition reaction product to be obtained shall have both a photoinitiation performance and a photocuring functionality, and therefore well functions as a reactive initiator to further better the effect of migration prevention.

(Reactive Compound (II) Functioning as Michael Acceptor)

The reactive compound (II) having a function as a Michael acceptor that can be used here is preferably a polyfunctional reactive group having plural photocuring groups as capable of further bettering the photocuring functionality.

Here, the polyfunctional reactive compound having plural photocuring groups includes an α,β-unsaturated carbonyl compound such as a maleimide compound, a maleate compound, a fumarate compound, a (meth)acrylate compound, etc. Among these, a (meth)acrylate compound is especially preferred as facilitating Michael addition reaction control in synthesis and as capable of expecting high reactivity in photocuring and effective migration prevention.

Examples of the (meth)acrylate compound include, for example and though not limited thereto, difunctional acrylates such as diethylene glycol di(meth)acrylate, dipropylene glycol di(meth)acrylate, tripropylene glycol di(meth)acrylate, 3-methyl-1,5-pentanediol di(meth)acrylate, hexanediol di(meth)acrylate, neopentyl glycol di(meth)acrylate, etc.; polyfunctional (meth)acrylates such as trimethylolpropane tri(meth)acrylate and alkyleneoxide-modified derivatives thereof with, for example, ethylene oxide, propylene oxide, etc., pentaerythritol tri or tetra(meth)acrylate and alkyleneoxide-modified derivatives thereof with, for example, ethylene oxide, propylene oxide, etc., ditrimethylolpropane tetra(meth)acrylate and alkyleneoxide-modified derivatives thereof with, for example, ethylene oxide, propylene oxide, etc., dipentaerythritol tetra or penta or hexa(meth)acrylate and caprolactone-modified derivatives thereof, etc.; epoxy (meth)acrylates obtained through reaction of a polyglycidyl ether such as bisphenol A diglycidyl ether, trimethylolpropane triglycidyl ether or the like and (meth)acrylic acid; urethane (meth)acrylates to be obtained through reaction of a polyisocyanate compound such as isophorone diisocyanate, hexamethylene diisocyanate trimer or the like, and a hydroxyl group-having acrylate such as hydroxyethyl (meth)acrylate, pentaerythritol tri(meth)acrylate or the like; polyester (meth)acrylates to be obtained through reaction of a polybasic acid such as trimellitic acid, succinic acid or the like, a polyol such as ethylene glycol, neopentyl glycol or the like, and a hydroxyl group-having (meth)acrylate such as hydroxyethyl (meth)acrylate, pentaerythritol tri(meth)acrylate or the like; high-molecular-weight poly(meth)acrylates to be obtained through reaction of a polymer of glycidyl (meth)acrylate and a monofunctional (meth)acrylate, and (meth)acrylic acid, etc. These reactive compounds may be used either singly or as combined by mixing a plurality of these.

Above all, the reactive compound is most preferably a trifunctional or more polyfunctional (meth)acrylate compound, as capable of forming a high-molecular-weight form after cured and capable of being firmly fixed by a cured film. When a trifunctional or more polyfunctional (meth)acrylate having 3 or more (meth)acryloyl groups is selected as the reactive compound having a function as a Michael acceptor, the embodiment is preferred since the Michael addition reaction product of the present invention can have 2 or more photocuring groups.

(Michael Addition Reaction)

In the present invention, the Michael addition reaction between the above-mentioned α-aminoacetophenone skeleton-containing compound (I) and the reactive compound (II) having a function as a Michael acceptor is not specifically limited, and the reaction can be carried out under known conventional reaction conditions. As one general method, there is mentioned a method of mixing the α-aminoacetophenone skeleton-containing compound (I) and the reactive compound (II) having a function as a Michael acceptor, at 0 to 150° C. in a reactor, in which a catalyst and a solvent can be used.

Examples of usable catalysts include tetraethylammonium fluoride, tetrabutylammonium hydroxide, potassium hydroxide, tetramethylguanidine, diazabicycloundecene, sodium t-butyrate, tri-n-octyl phosphine, triphenyl phosphine, etc.

Examples of the organic solvent include saturated hydrocarbons such as pentane, hexane, heptane, cyclohexane, etc.; aromatic hydrocarbons such as toluene, xylene, etc.; alcohols such as methanol, ethanol, isopropanol, 2-butanol, t-butanol, ethylene glycol, carbitol, etc.; ethers such as dimethyl ether, diethyl ether, 1,4-dioxane, tetrahydrofuran (THF), etc.; amides such as dimethylformamide (DMF), etc.; halogen-containing solvents such as chloroform, dichloromethane, etc.; dimethyl sulfoxide (DMSO), etc.

The mixing ratio of the above-mentioned α-aminoacetophenone skeleton-containing compound (I) and the reactive compound (II) having a function as a Michael acceptor is, though not specifically limited, preferably such that the equivalent ratio of the group (ii) having a Michael acceptor function to the group (i) having a Michael addition donor function [(ii)/(i)] is 1/1.5 to 1/30. When the equivalent ratio [(ii)/(i)] is more than 1/1.5, a possibility of migration of the compound (I) or a decomposed matter thereof from a coating film may increase, and when the equivalent ratio [(ii)/(i)] is less than 1/30, the curing performance of the Michael addition reaction product may worsen. From the viewpoint of the curing performance of the Michael addition reaction product and the amount of the materials that may be released from a coating film, the equivalent ratio [(ii)/(i)] is especially preferably 1/2 to 1/20.

As the Michael addition reaction products to be obtained in the manner as above, for example, the following formulae (M1) to (M16) are mentioned.

[Chem. 64]

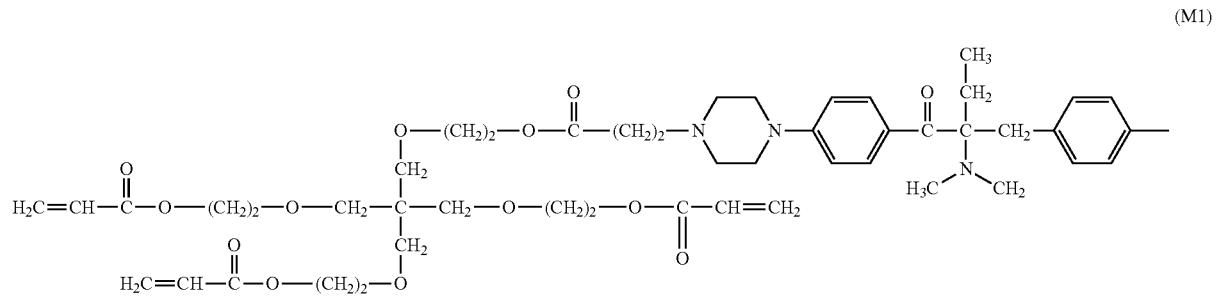

(M1)

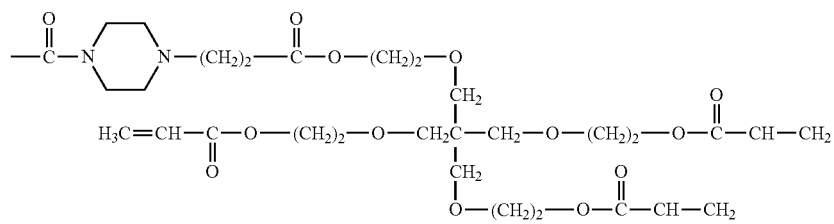
[Chem. 65]
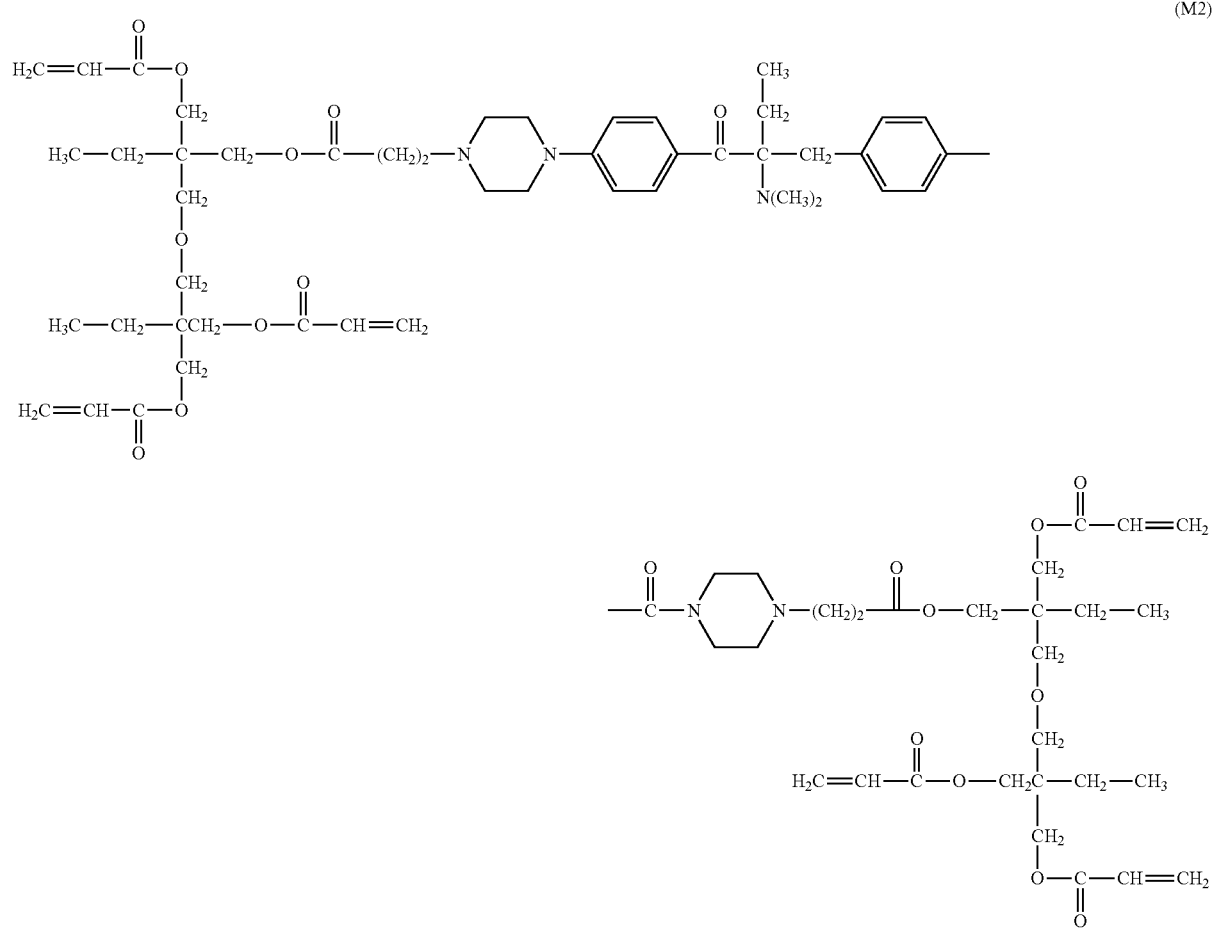
(M2)
[Chem. 66]
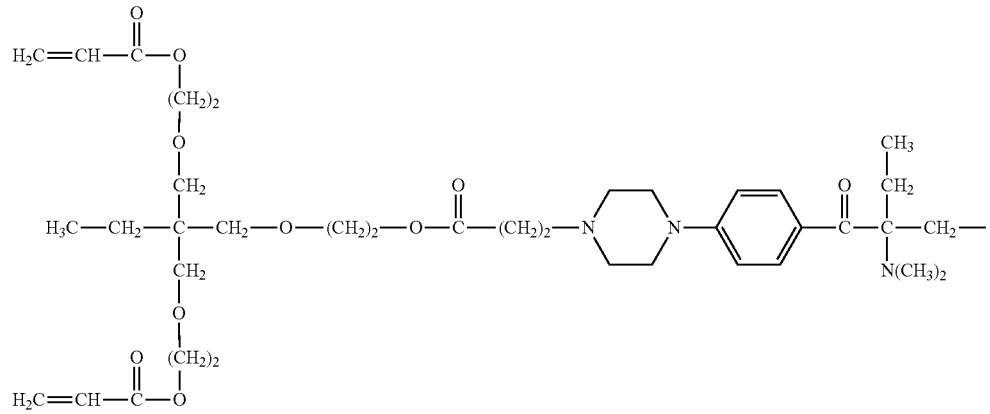
(M3)

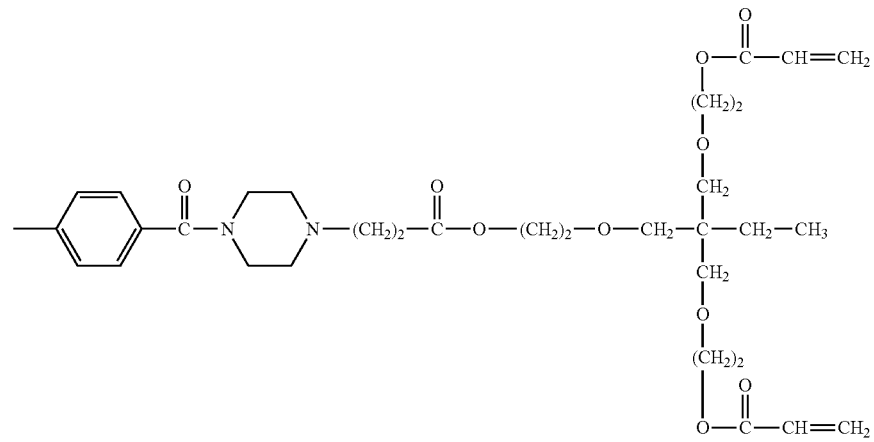
[Chem. 67]
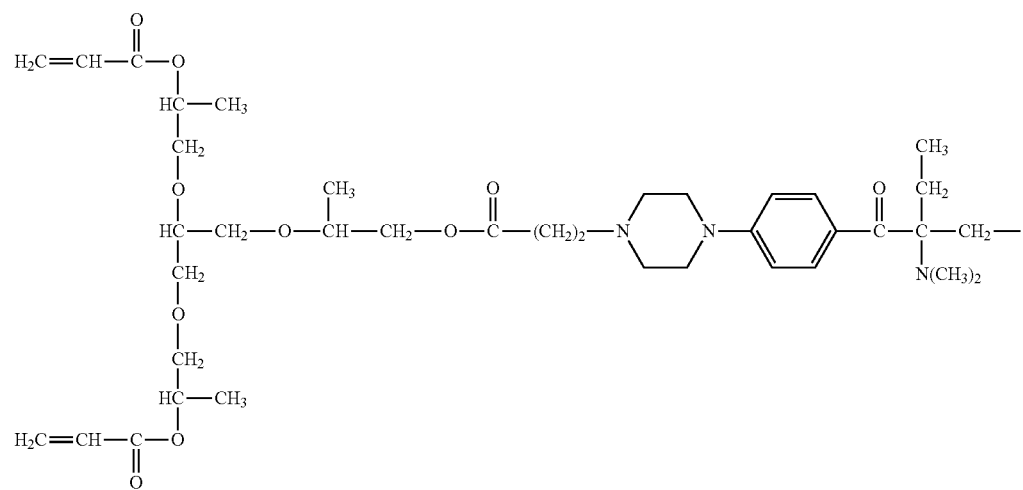
(M4)
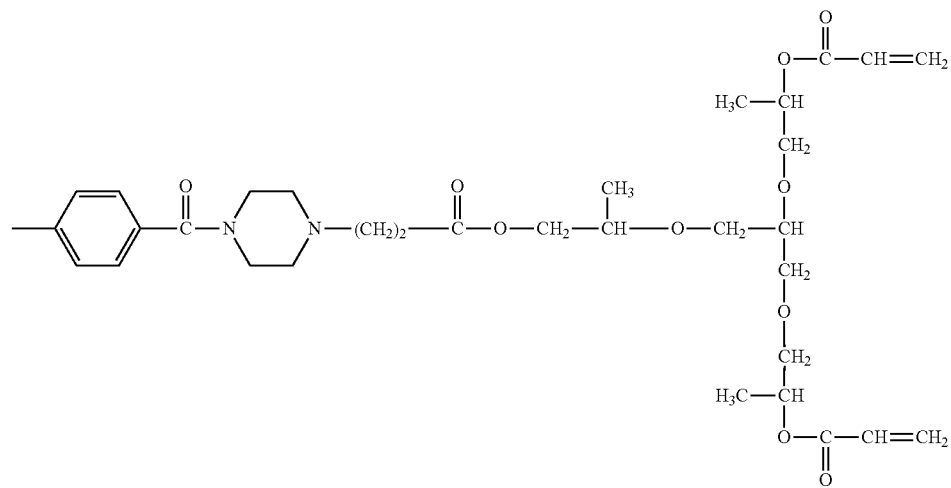

-continued
[Chem. 68]
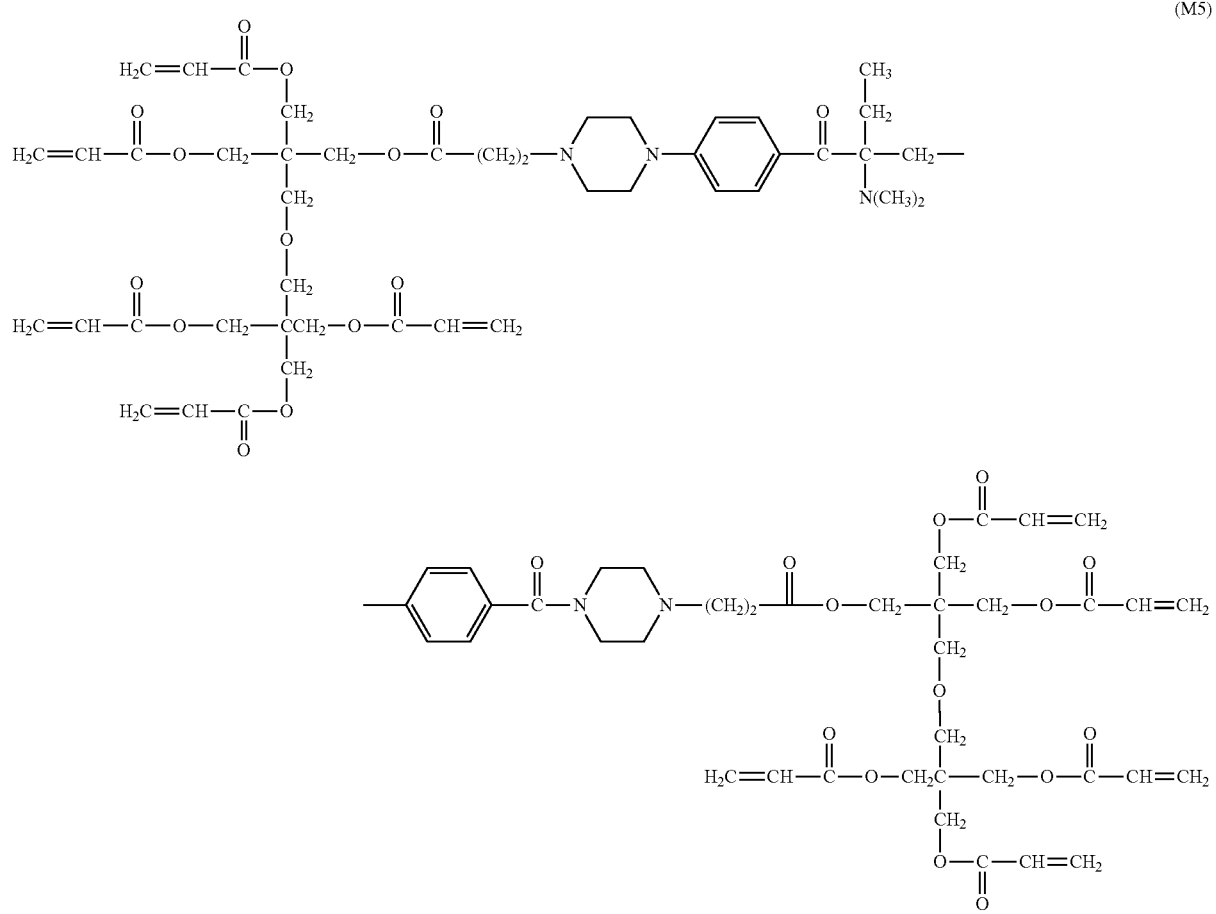
(M5)
[Chem. 69]
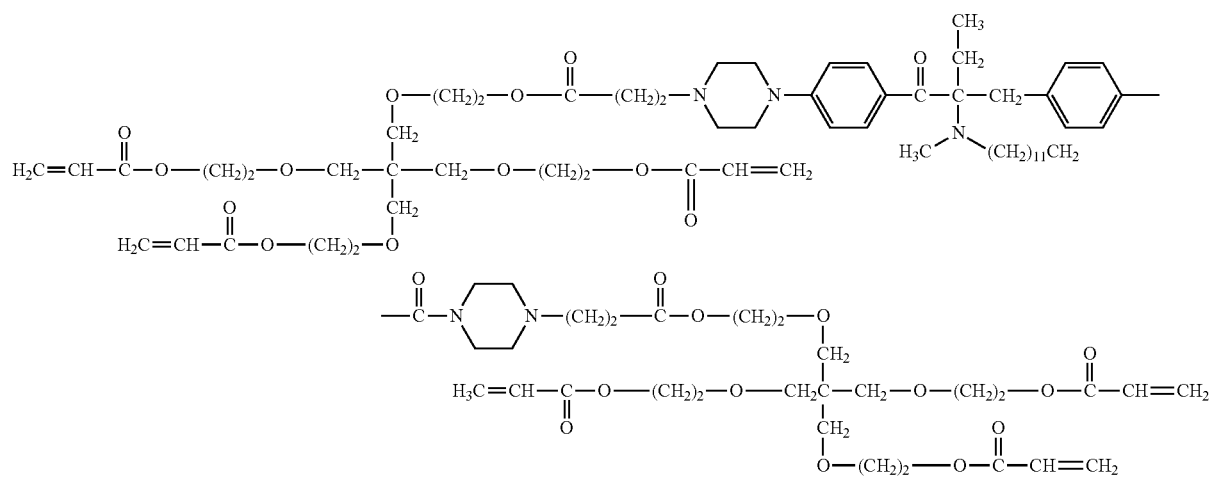
(M6)

-continued
[Chem. 70]
(M7)
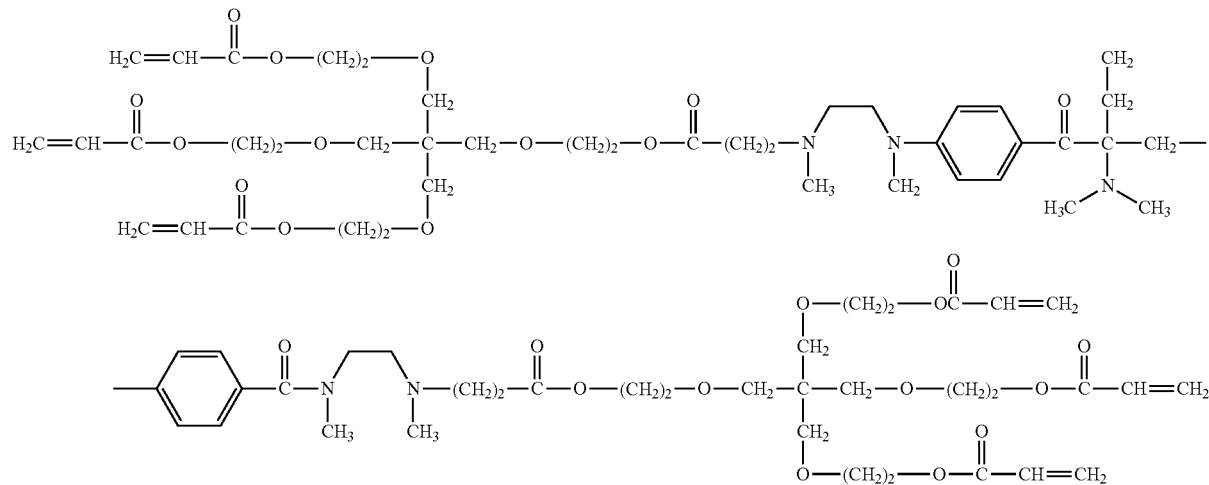
[Chem. 71]
(M8)
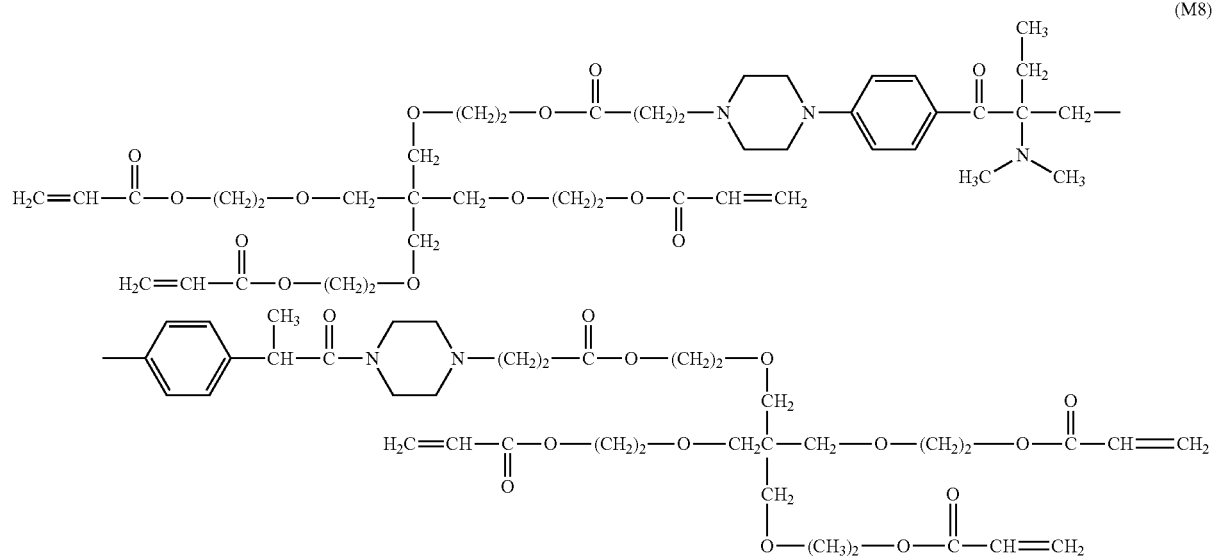
[Chem. 72]
(M9)
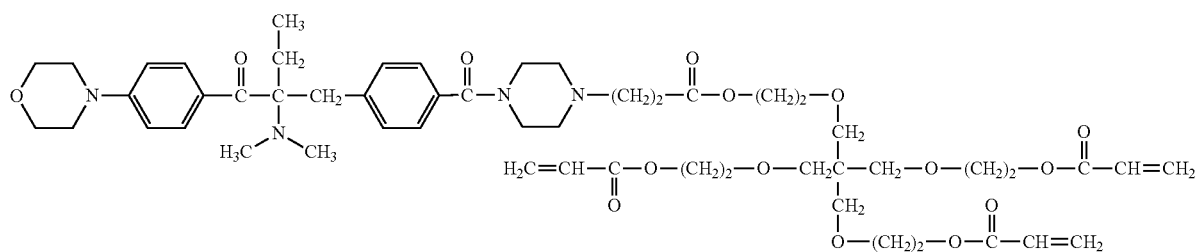

[Chem. 73]
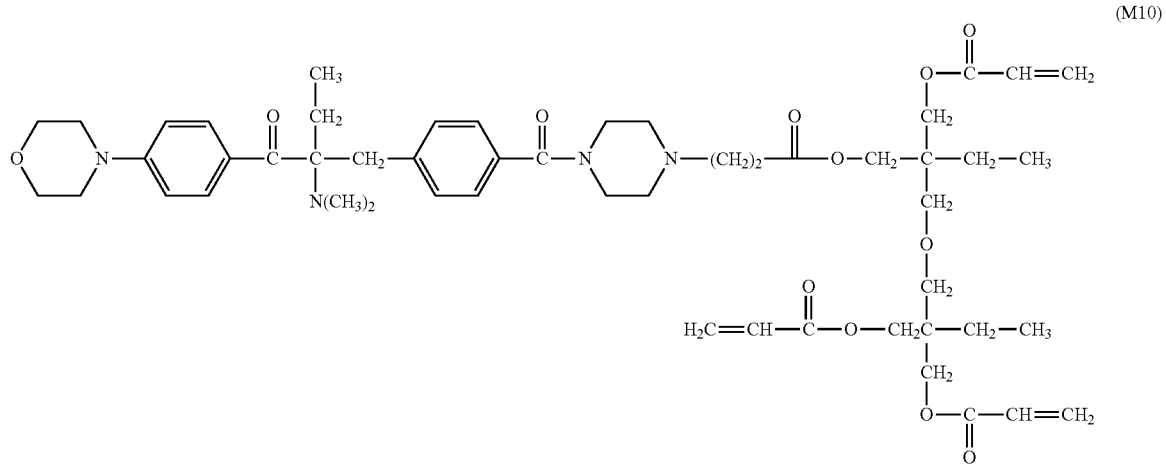
(M10)
[Chem. 74]
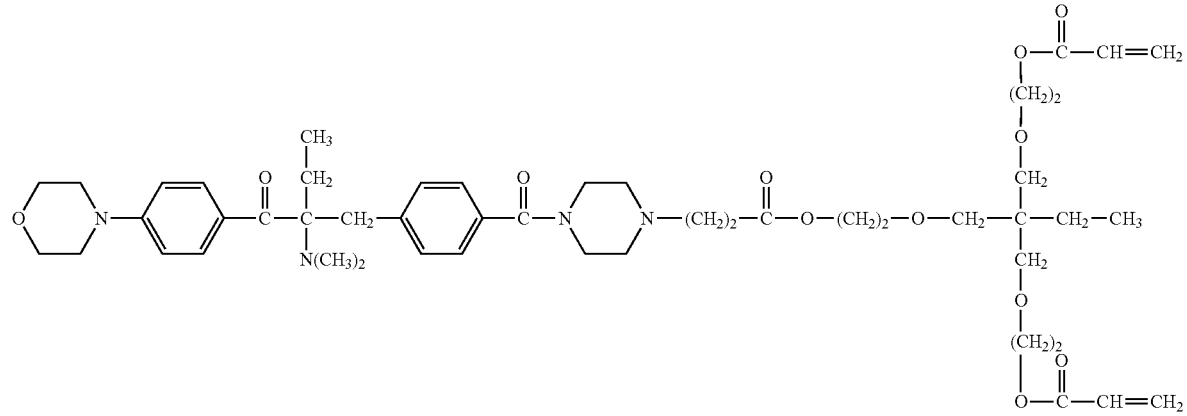
(M11)
[Chem. 75]
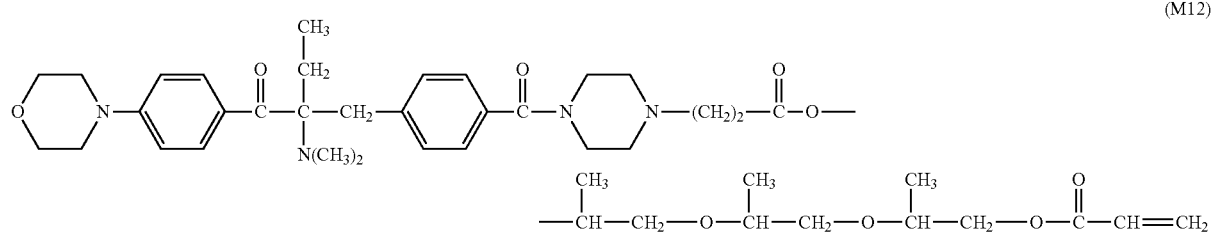
(M12)
[Chem. 76]
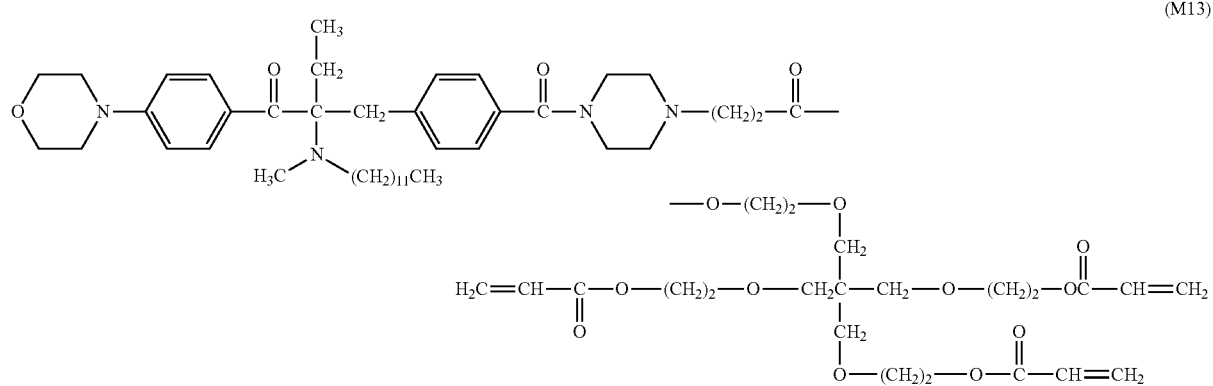
(M13)

[Chem. 77]

(M14)

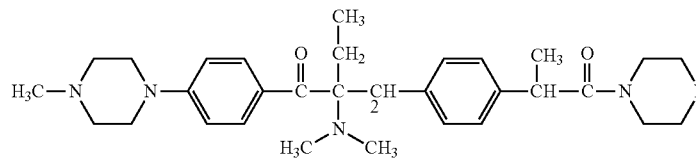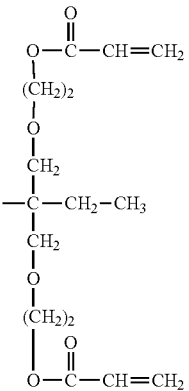

[Chem. 78]

(M15)

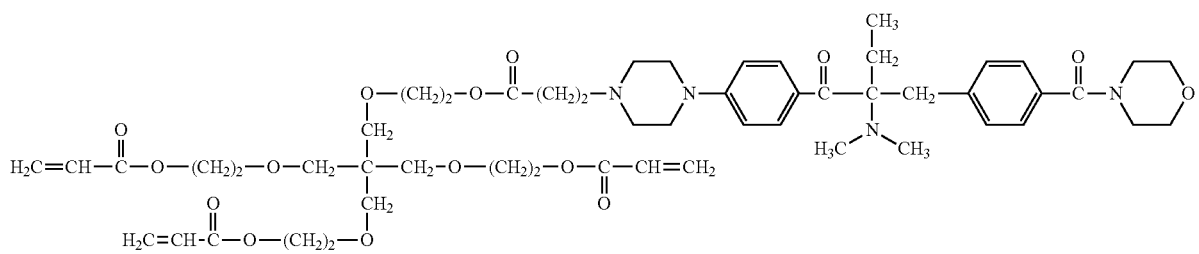

[Chem. 79]

(M16)

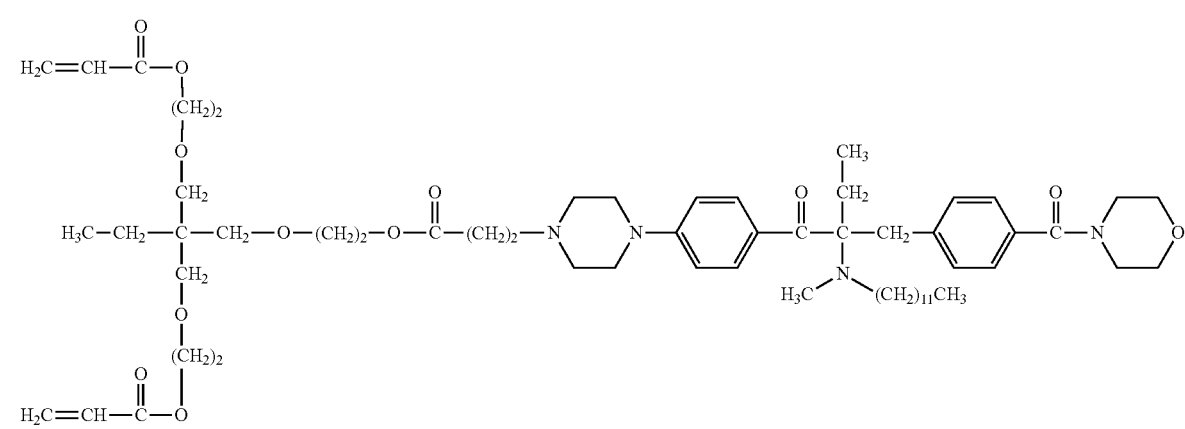

The compound (A) of the present invention described in detail hereinabove can be used not only as a production starting material for the above-mentioned α-aminoacetophenone skeleton-containing compound (I) but also as a polymerization initiator as it is the compound (A) itself.

The compound (A) may be reacted with a compound (B) capable of being reacted with the compound (A) to produce a compound (C) having a polymerization initiation performance depending on the use and the required characteristics. Specifically, by selecting the compound (B), various modes of molecular planning typically including molecular weight increase to give high-molecular-weight polymers can be readily attained thereby providing compounds having various functions depending on the desired use.

The compound (B) to be used herein may be any one having, in the molecular structure of the compound (B), a functional group capable of reacting with the reactive functional group existing in the compound (A), and specifically in the case where the compound (A) has a secondary amino group as the functional group represented by $Y_1$— in the compound (A), a compound having a functional group (b1) reactive with the secondary amino group or a functional group (b2) reactive with the structural moiety represented by the following structural formula:

—$X_2$—Z  [Chem. 80]

In the above-mentioned general formula (1') may be mentioned.

The functional group (b1) in the compound (B) includes a carboxyl group, an acid anhydride group, a glycidyl group. On the other hand, the functional group (b2) in the compound (B) includes an amino group, a hydroxyl group, a thiol group, a glycidyl group.

As the compound (B) having such a functional group, specifically, as the compound having a hydroxyl group as the functional group (b2), for example, there are mentioned linear alkylene dials such as ethylene glycol, diethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,12-dodecanediol, 1,14-tetradecanediol, 1,16-hexadecanediol, 1,18-octadecanediol, 1,20-eicosanediol, etc.; polyether glycols such as polyoxyethylene glycol, polyoxypropylene glycol, etc.; modified polyether polyols obtained through ring-cleavage polymerization of the above-mentioned linear alkylene diol with various types of cyclic ether bond-containing compounds such as ethylene oxide, propylene oxide, tetrahydrofuran, ethylglycidyl ether, propylglycidyl other, butylglycidyl, there, phenylglycidyl ether, allylglycidyl ether, etc.;

lactone-type polyester dials obtained through polycondensation reaction of the above-mentioned linear alkylene diol with various types of lactones such as ε-caprolactone, etc.; trifunctional or more polyfunctional polyols such as trimethylolethane, trimethylolpropane, 2,2,4-trimethyl-1,3-pentanediol, glycerin, hexanetriol, pentaerythritol, and ethylene oxide-modified or propylene oxide-modified derivatives thereof, etc.;

hydroxyl group-containing (meth)acrylates such as diethylene glycol mono(meth)acrylate, dipropylene glycol mono (meth)acrylate, tripropylene glycol mono(meth)acrylate, 3-methyl-1,5-pentanediol mono(meth)acrylate, hexanediol mono(meth)acrylate, neopentyl glycol mono(meth)acrylate, trimethylolpropane di(meth)acrylate, and ethylene oxide or propylene oxide-modified derivatives thereof, pentaerythritol tri(meth)acrylate and ethylene oxide or propylene oxide-modified derivatives thereof, ditrimethylolpropane di or tri(meth)acrylate and alkylene oxide-modified derivatives thereof with ethylene oxide, propylene oxide or the like, dipentaerythritol tri or tetra or penta(meth)acrylate and caprolactone-modified derivatives thereof, etc.

As the compound having a thiol group as the functional group (b1) or the functional group (b2), there are mentioned polythiol compounds including aliphatic polythiols such as 1,2-ethanedithiol, 1,2- and 1,3-propanedithiol, 1,4- and 1,2- and 2,3-butanedithiol, 1,6-hexanedithiol, 1,8-octanedithiol, 1,10-decanedithiol, 2,2'-mercaptoethyl ether, 3,6-dioxa-1,8-octanedithiol, 3,7-dithia-1,9-nonanedithiol, etc.; aromatic dithiols such as 1,4-benzenedimethanethiol, 1,3-benzenedimethanethiol, etc.

The compound having an amino group as the functional group (b2) includes aliphatic polyamines such as ethylenediamine, 1,2- and 1,3-diaminopropane, 1,4-diaminobutane, 1,6-diaminohexane, 1,8-diaminooctane, 1,10-diaminodecane, 2,2'-diaminodiethyl ether, 1,2-diaminocyclohexane, 2,2',2'-triaminotriethylamine, tris(3-aminopropyl)amine, etc.; aromatic polyamine compounds such as 1,2- or 1,3- or 1,4-phenylenediamine, 3,4'- or 4,4'-diaminodiphenyl ether, tris(4-aminophenyl)amine, 1,3,5-tris(4-aminophenyl)benzene, 1,3- or 1,4-xylylenediamine, etc.

Here, the compound (B) having a glycidyl group as the functional group (b1) or (b2) includes aliphatic diglycidyl ethers such as the above-mentioned ethylene glycol diglycidyl ether, 2,2'-(2,6-dioxaheptane-1,7-diyl)bisoxirane, 1,4-bis(glycidyloxy)butane, 2,3-butylene glycol diglycidyl ether, 1,5-pentylene glycol diglycidyl ether, 1,6-bis(glycidyloxy)hexane, 1,7-heptylene glycol diglycidyl ether, 1,8-octylene glycol diglycidyl ether, etc.; aliphatic polyglycidyl ethers having 3 or more epoxy groups in the molecular structure, such as trimethylolpropane triglycidyl ether, pentaerythritol tetraglycidyl ether, etc.; epoxy group-containing vinyl polymers obtained through polymerization of a glycidyl group-containing compound such as glycidyl (meth) acrylate glycidyl α-ethyl (meth)acrylate or the like with a vinyl group-containing aliphatic compound such as butadiene, methyl (meth)acrylate, ethyl (meth)acrylate, dimethyl fumarate or the like; aromatic diglycidyl ethers such as bisphenol A-type epoxy resin, bisphenol F-type epoxy resin, bisphenol, S-type epoxy resin, 1,4-naphthalenediol diglycidyl ether, 1,6-naphthalenediol diglycidyl ether, 2,6-naphthalenediol diglycidyl ether, 2,7-naphthalenediol diglycidyl ether, naphthalene-2,6-dimethanoldiglycidyl ether, etc.; aromatic polyglycidyl ethers having 3 or more epoxy groups in the molecular structure, such as 4,4,4''-methylidynetrisphenol triglycidyl ether, etc.; phenol-novolak epoxy resins, cresol novolak epoxy resins, bisphenol novolak epoxy resins;

compounds having a glycidyl group and a (meth)acrylate group, such as glycidyl (meth)acrylate, 2-hydroxyethyl (meth)acrylate glycidyl ether, 4-hydroxybutyl (meth)acrylate glycidyl ether, 6-hydroxyhexyl (meth)acrylate glycidyl ether, 8-hydroxyoctyl (meth)acrylate glycidyl ether, mono (meth)acrylates of the above-mentioned aromatic diglycidyl ethers, trimethylolpropane triglycidyl ether mono or di(meth)acrylate, mono or di(meth)acrylates of the above-mentioned aromatic polyglycidyl ethers having 3 or more epoxy groups in the molecular structure, etc. One alone or two or more of these may be used either singly or as combined.

The compound (B) having an acid anhydride group as the functional group (b1) includes, for example, acetic anhydride, propionic anhydride, succinic anhydride, maleic anhydride, phthalic anhydride, etc.

The compound (B) having a carboxyl group as the functional group (b1) includes formic acid, acetic acid, saturated fatty acids, unsaturated fatty acids, benzoic acid, (meth) acrylic acid, etc.

Among these, use of the linear alkylene diol, the polyether glycol, the modified polyether polyol, the lactone-type polyester diol, or the trifunctional or more polyfunctional polyol is preferred, as the compound (C) to be obtained can function as a high-molecular-weight polymerization initiator while maintaining good curability, therefore realizing a good migration-reducing effect. Use of the hydroxyl group-containing (meth)acrylate or the compound having a glycidyl group and a (meth)acrylate group is also preferred, since the compound (C) to be obtained functions as a polymerizing polymerization initiator and has a high effect of fixation in a cured film, therefore realizing a good migration-reducing effect. In particular, a difunctional or more polyfunctional (meth)acrylate having 2 or more (meth)acryloyl groups in one molecule is most preferred as realizing a high effect of fixation in a cured film.

In the case where the compound (B) having a glycidyl group as the functional group (b2) is used, the compound (A) represented by the general formula (1') and the compound (B) having a glycidyl group may be reacted in a mode of heating reaction or the like, using a tetraalkylammonium salt such as tetrabutylammonium bromide or the like or a triaryl phosphine such as triphenyl phosphine or the like as a catalyst, thereby producing the compound (C).

In the case where a linear alkylene diol, a polyether glycol, the above-mentioned modified polyether polyol, the above-mentioned lactone-type polyester diol or the above-mentioned trifunctional or more polyfunctional polyol is used as the compound (B), or where the above-mentioned hydroxyl group-containing (meth)acrylate or the compound having a glycidyl group and a (meth)acrylate group is used as the compound, $Y_1$ in the general formula (1') is preferably a morpholino group from the viewpoint of curability, and in the case, compounds represented by the following structural formula (M'1) to structural formula (M'24) are especially preferred.

[Chem. 81]
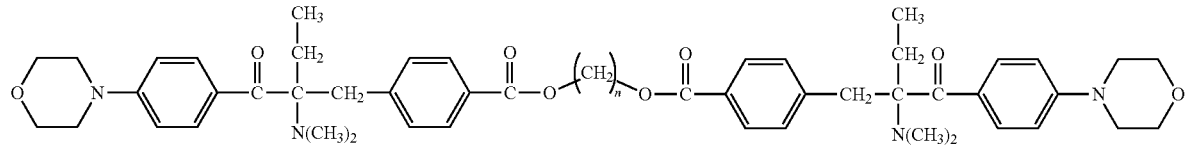
(M'1)
[In the structural formula (M'1) n indicates an integer of 2 to 18.]
[Chem. 82]
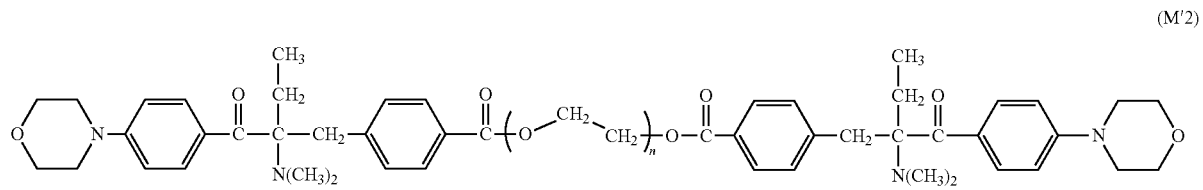
(M'2)
[In the structural formula (M'2), n indicates an integer of 2 to 18.]
[Chem. 83]
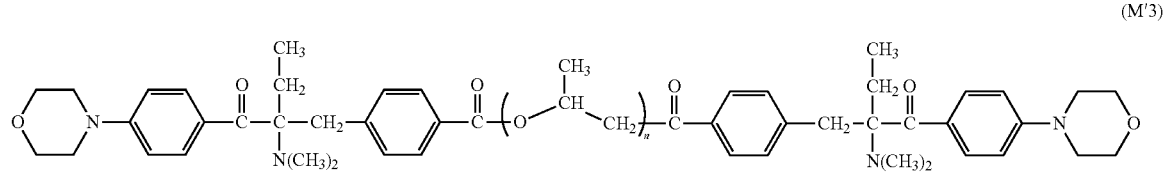
(M'3)
[In the structural formula (M'3), n indicates an integer of 1 to 15.]
[Chem. 84]
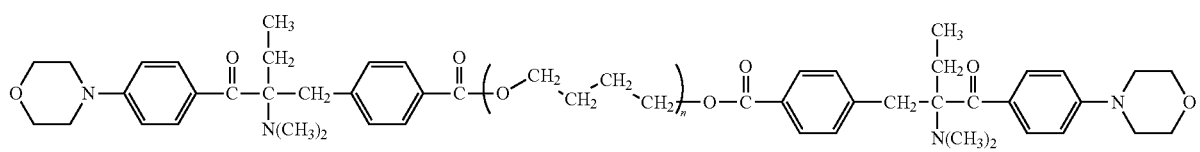
(M'4)
[In the structural formula (M'4), n indicates an integer of 1 to 15.]

[Chem. 85]
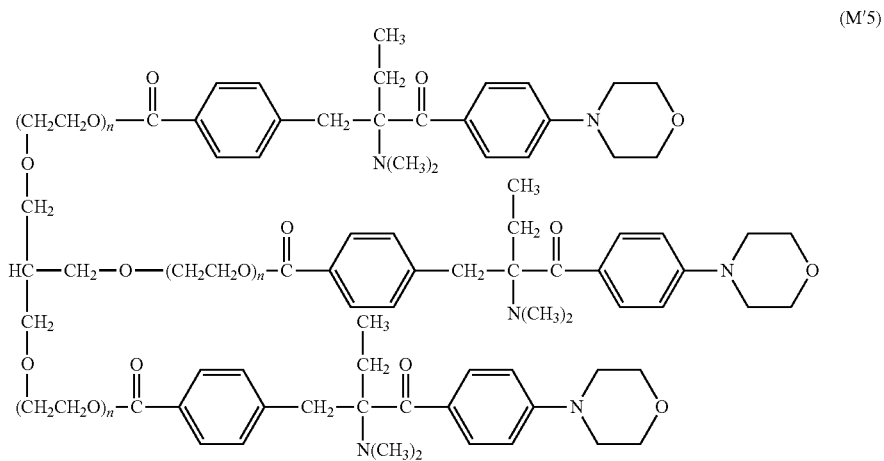
(M′5)
[In the structural formula (M′5), the total of three n's is 0 to 9.]
[Chem. 86]
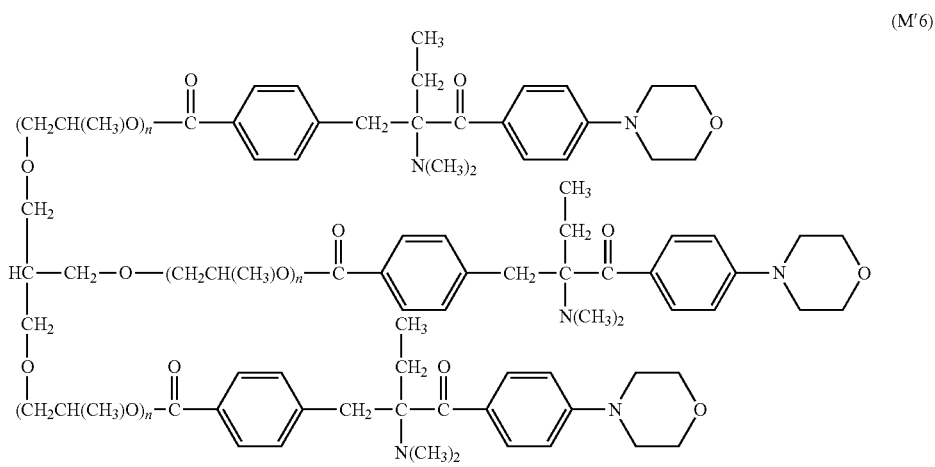
(M′6)
[In the structural formula (M′6), the total of three n's is 1 to 9.]

[Chem. 87]
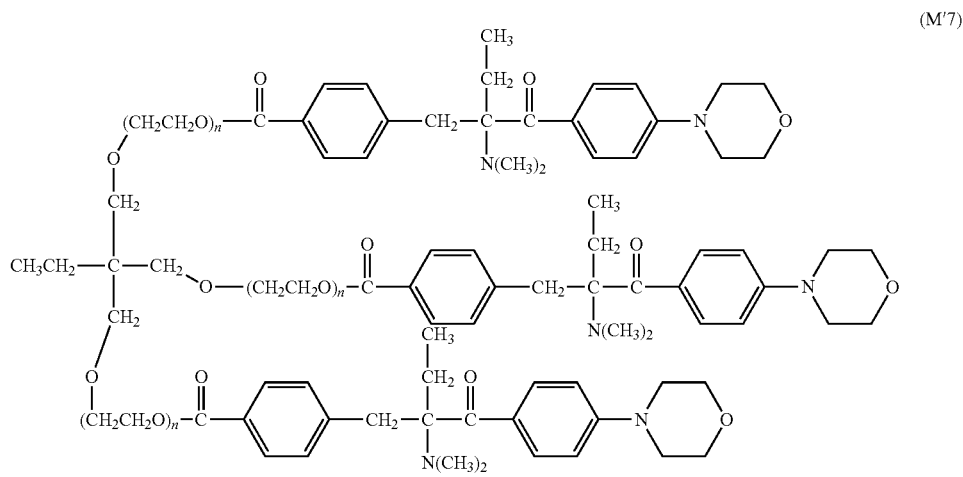
(M'7)
[In the structural formula (M'7), the total of three n's is 0 to 9.]
[Chem. 88]
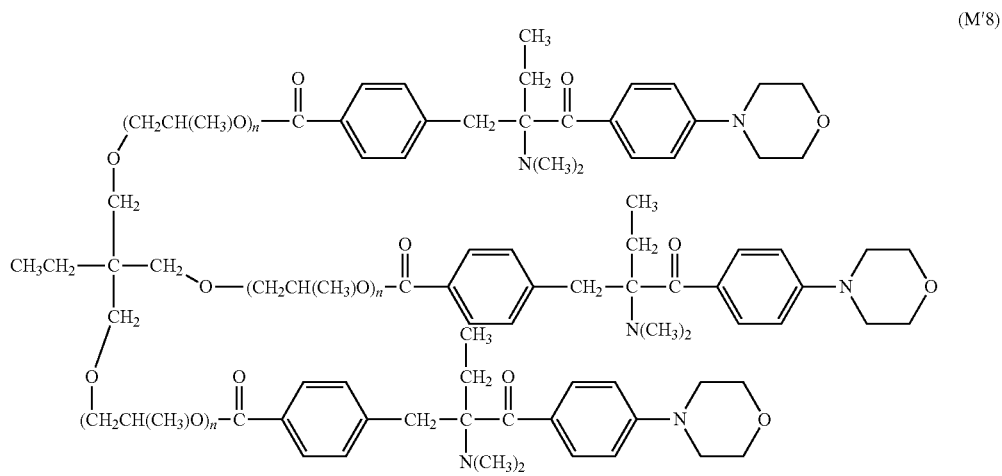
(M'8)
[In the structural formula (M'8), the total of three n's is 1 to 9.]

[Chem. 89]
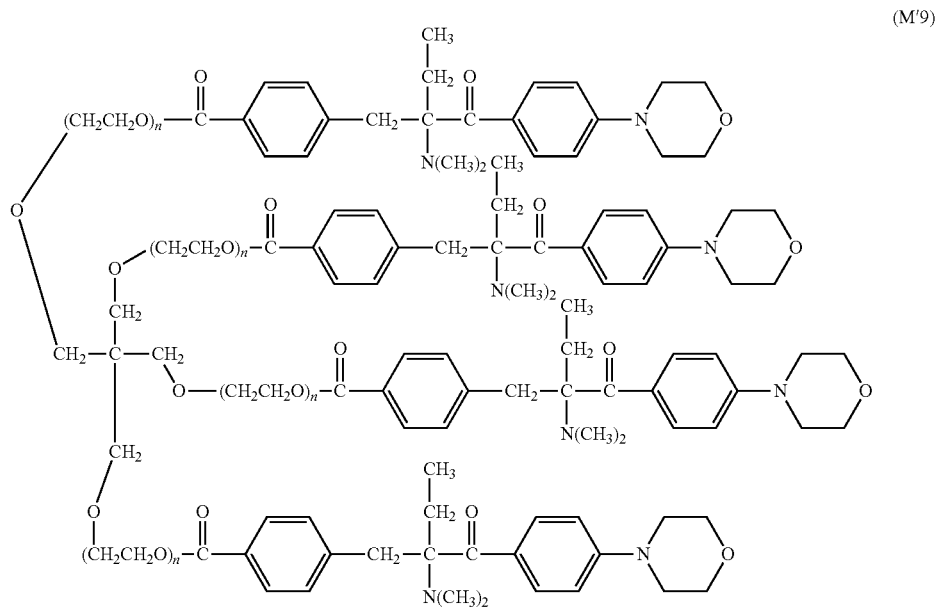
(M'9)
[In the structural formula (M'9), the total of three n's is 0 to 12.]
[Chem. 90]
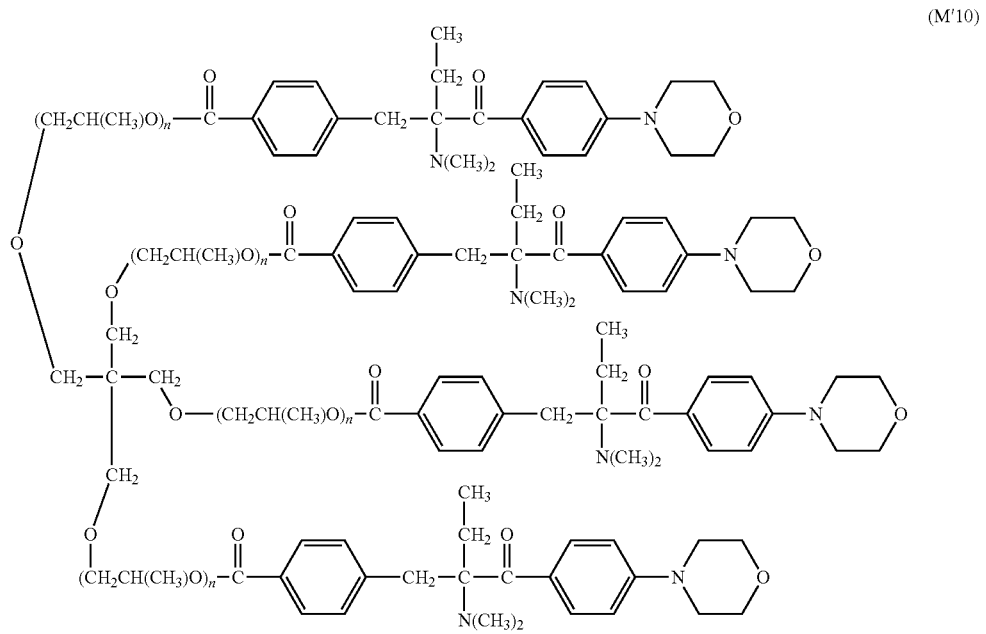
(M'10)
[In the structural formula (M'10), the total of three n's is 1 to 12.]

[Chem. 91]
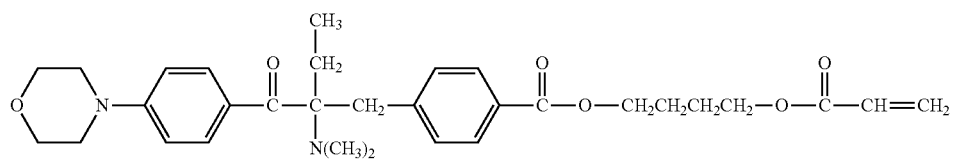
(M'11)
[Chem. 92]
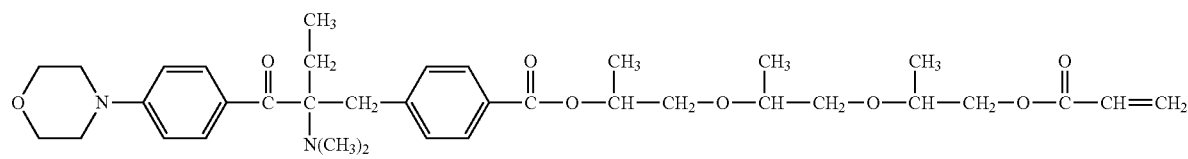
(M'12)
[Chem. 93]
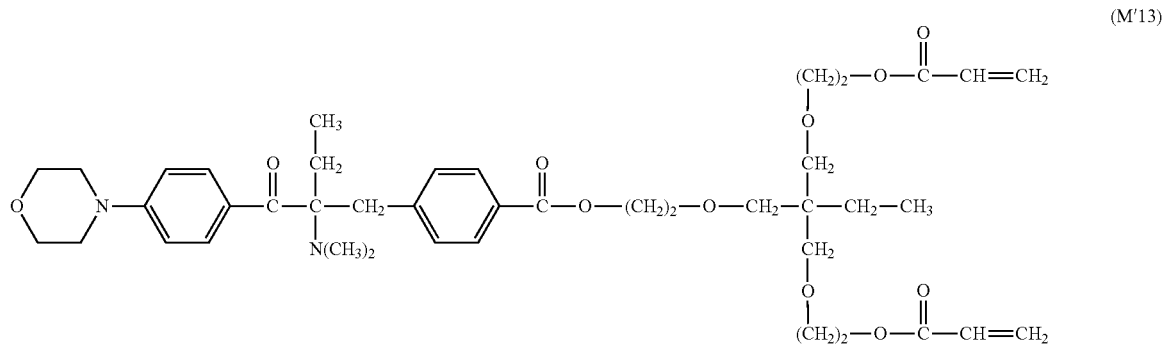
(M'13)
[Chem. 94]
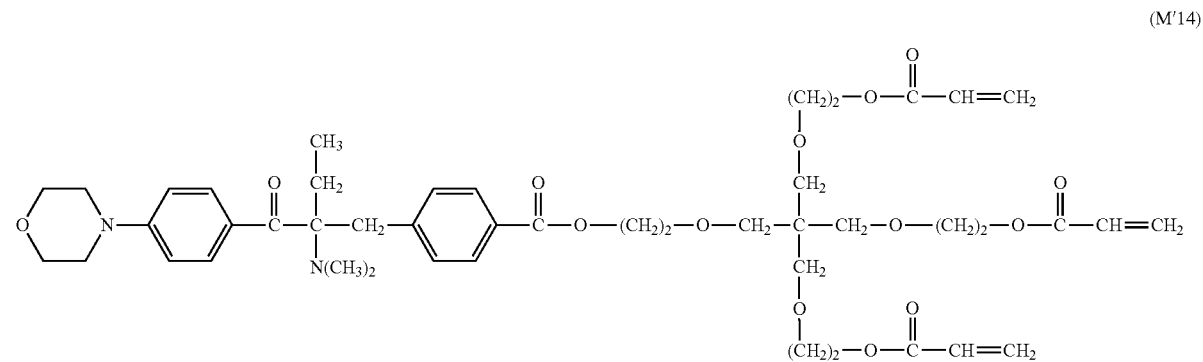
(M'14)
[Chem. 95]
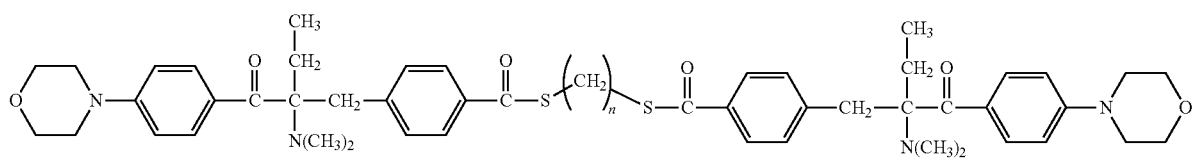
(M'15)
[In the structural formula (M'15), n indicates an integer of 2 to 18.]

[Chem. 96]
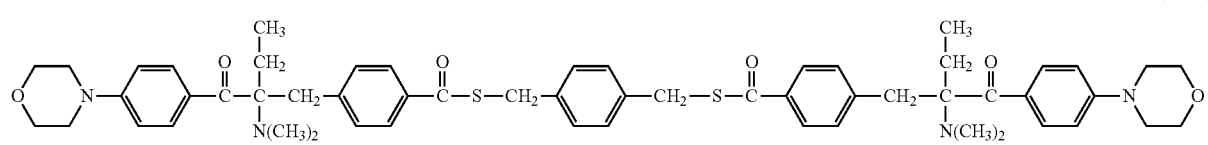
(M'16)
[Chem. 97]
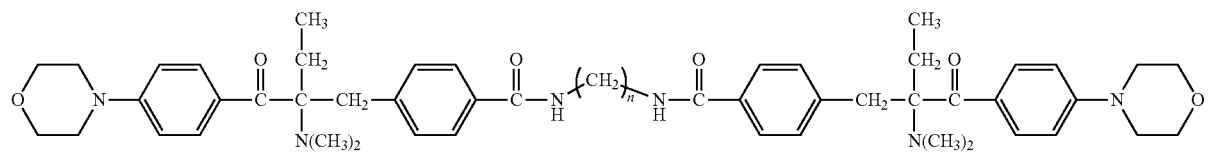
(M'17)
[In the structural formula (M'17), n indicates an integer of 2 to 18.]
[Chem. 98]
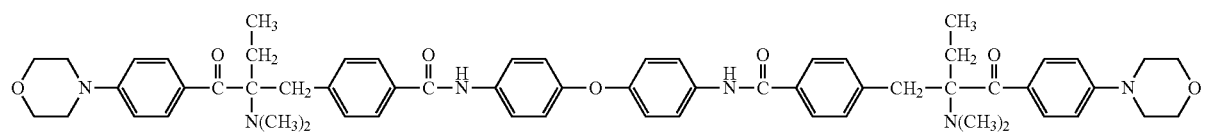
(M'18)
[Chem. 99]
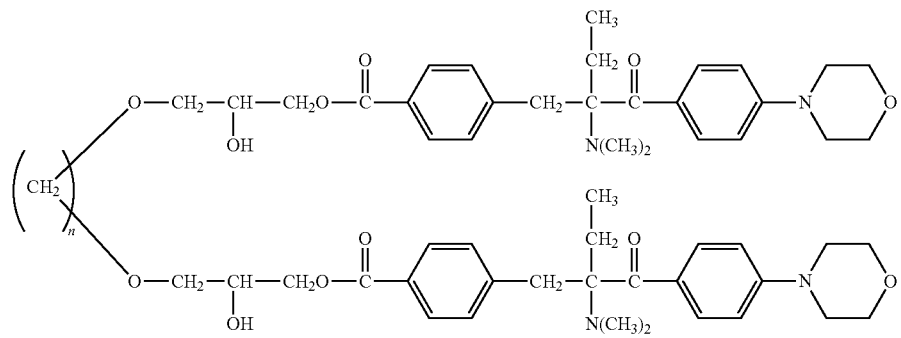
(M'19)
[In the structural formula (M'19), n indicates an integer of 2 to 18.]

[Chem. 100]
(M'20)
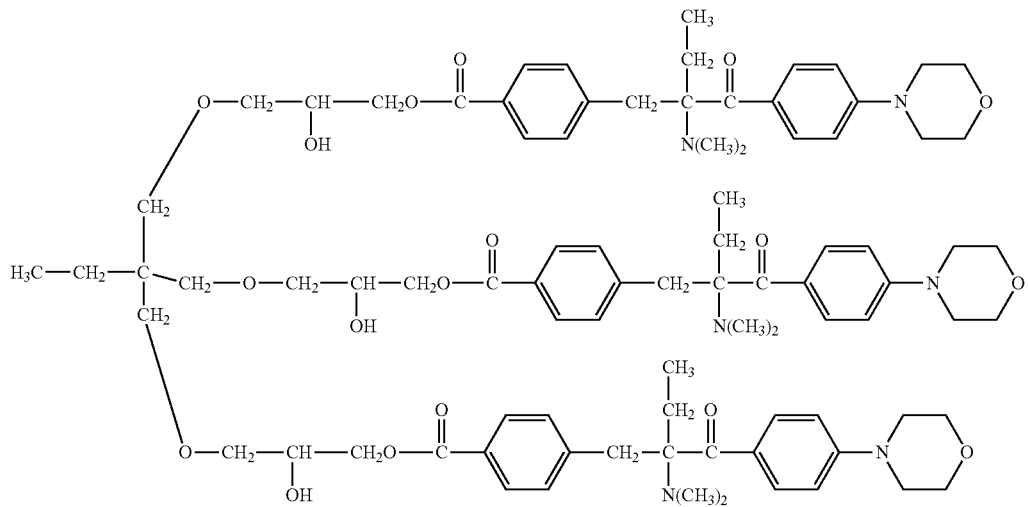
[Chem. 101]
(M'21)
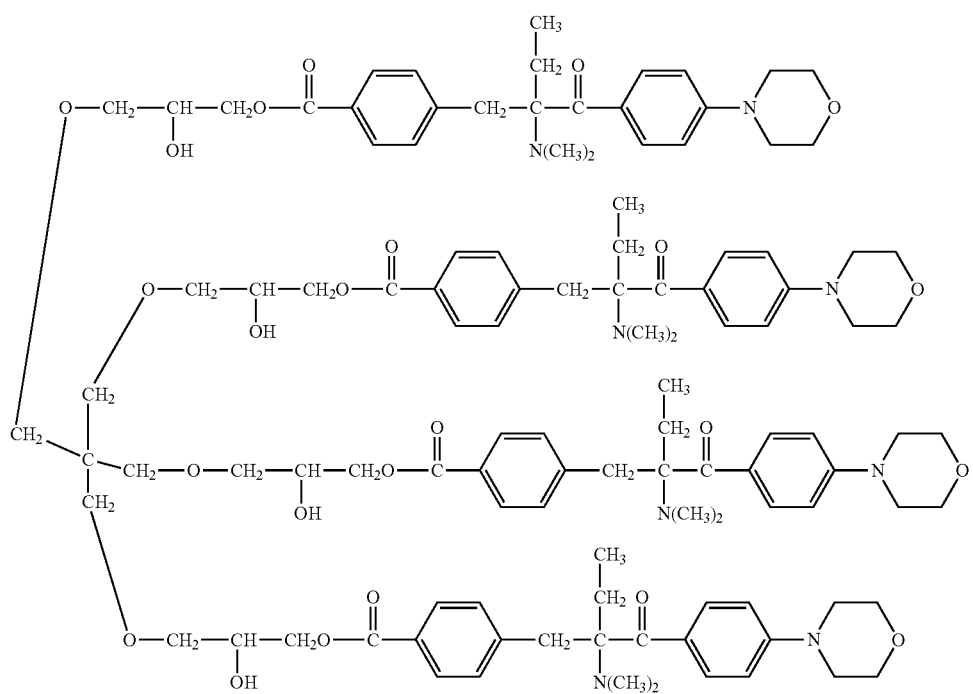

[Chem. 102]

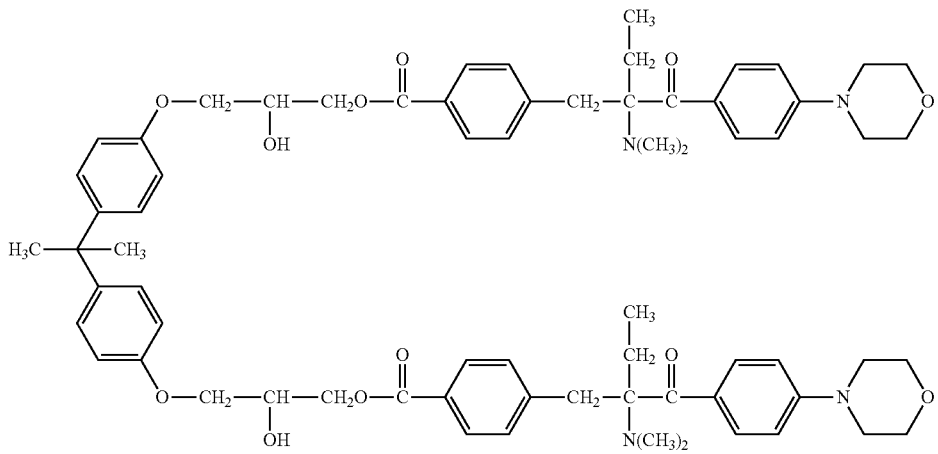

(M'22)

[Chem. 103]

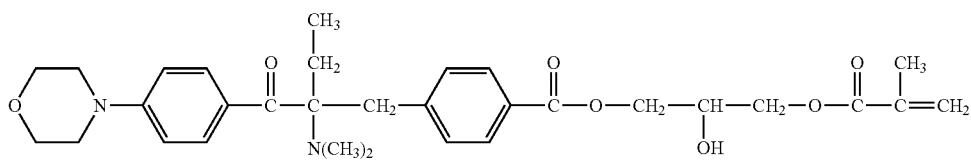

(M'23)

[Chem. 104]

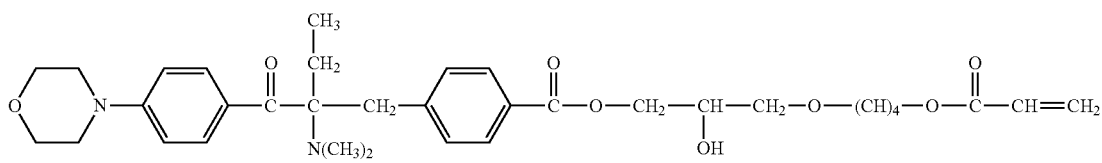

(M'24)

As described above, the compound (A) of the present invention can be favorably used as a photopolymerization initiator excellent in curability as it is. In addition, the compound (C) can also be favorably used as a photopolymerization initiator capable of reducing migration and excellent in curability. Accordingly, when the compound (A) of the present invention or the compound (C) is used as a photopolymerization initiator and when a photocurable reactive compound is incorporated, an active energy ray curable composition can be prepared.

However, in the present invention, use of a Michael addition reaction product of the above-mentioned α-aminoacetophenone skeleton-containing compound (I) having a function of a Michael addition donor and the reactive compound (II) having a function of a Michael acceptor (hereinafter this is abbreviated as "Michael addition reaction product (III)") as a photopolymerization initiator, is preferable as capable of exhibiting excellent curability and capable of bettering the effect of reducing migration.

Specifically, the active energy ray curable composition of the present invention contains the Michael addition reaction product (II) of the present invention as a photopolymerization initiator and contains a photocurable reactive compound.

The photocurable reactive compound includes an ethylenic double bond-having maleimide compound, a maleate compound, a fumarate compound, a (meth)acrylate compound and the like, like those described above. From the viewpoint of easy availability of starting materials and from the viewpoint of curing rate, a (meth)acrylate compound is preferred.

The (meth)acrylate compound is, though not specifically limited thereto, preferably a polyfunctional (meth)acrylate compound having plural reactive groups capable of contributing toward curing by irradiation, like those mentioned hereinabove.

In the case of an active energy ray curable composition whose viscosity is desired to be low, a low-viscosity monofunctional (meth)acrylate compound may be incorporated therein in addition to the above-mentioned (meth)acrylate compound, within a range not detracting from the advantageous effects of the present invention.

Here, examples of the low-viscosity (meth)acrylate compound include, for example, alkyl (meth)acrylates such as methyl acrylate, ethyl acrylate, butyl acrylate, 2-ethylhexyl acrylate, etc. hydroxylalkyl (meth)acrylates such as 2-hydroxyethyl acrylate, 2-hydroxypropyl acrylate, etc.; alkoxyalkyl (meth)acrylates such as butoxyethyl acrylate, methoxybutyl (meth)acrylate, etc.; polyalkylene glycol (meth)acrylates such as polyethylene glycol mono(meth)acrylate, methoxydiethylene glycol (meth)acrylate, phenoxypolyethylene glycol (meth)acrylate, polypropylene glycol mono(meth)acrylate, methoxypolypropylene glycol (meth)acrylate, nonylphenoxypolypropylene glycol (meth)

acrylate, etc.; cycloalkyl (meth)acrylates such as cyclohexyl (meth)acrylate, dicyclopentadienyl (meth)acrylate, isobornyl (meth)acrylate, etc.; (meth)acrylates such as benzyl (meth)acrylate, 2-hydroxyethyl (meth)acryloylphosphate, tetrahydrofuryl (meth)acrylate, diethylaminoethyl (meth) acrylate, dimethylaminomethyl (meth)acrylate, etc.; (meth) acrylamides such as diacetone (meth)acrylamide, acryloylmorpholine, etc.; alkylvinyl ethers and cycloalkyl vinyl ethers such as ethyl vinyl ether, isobutyl vinyl ether, 2-ethylhexyl vinyl ether, cyclohexyl vinyl ether, etc.; hydroxyl group-containing vinyl ethers such as 2-hydroxyethyl vinyl ether, 3-hydroxypropyl vinyl ether, etc.; vinyl ether acrylates such as 2-vinyloxyethoxyethyl (meth)acrylate, etc.; N-vinyllactams and N-vinylalkylamides such as N-vinyl-2-pyrrolidone, N-vinylcaprolactam, N-vinylacetamide, etc.

Among the above-mentioned (meth)acrylate compounds, use of N-vinyl-2-pyrrolidone, N-vinylcaprolactam, N-vinylacetamide or 2-vinyloxyethoxyethyl (meth)acrylate is especially preferred, as exhibiting a high viscosity-reducing effect and hardly reducing the curing rate; and among these, use of 2-vinyloxyethoxyethyl (meth)acrylate is more preferred.

The amount of the (meth)acrylate compound to be used is, though not specifically limited thereto, preferably 5 to 95 parts by mass relative to 5 to 95 parts by mass of the Michael addition reaction product of the present invention. When the content of the Michael addition reaction product of the present invention is less than 5 parts by mass, there is a possibility that sufficient curing performance could not be realized, but when the content of the (meth)acrylate is less than 5 parts by mass, the coating film properties may tend to worsen. In particular, the Michael addition reaction product of the present invention is contained preferably in an amount of 10 to 90 parts by mass.

In the case where the above-mentioned 2-vinyloxyethoxyethyl (meth)acrylate is used, the amount thereof is, though capable of suitably controlled depending on the desired viscosity and the curing rate, preferably 10 parts by mass to 90 parts by mass relative to 100 parts by mass of the active energy ray curable composition of the present invention, more preferably 20 parts by mass to 80 parts by mass. As commercial products of 2-vinyloxyethoxyethyl (meth) acrylate, there are mentioned "VEEA", "VEEEA-AI" and "VEEM" all manufactured by Nippon Shokubai Co., Ltd.

The active energy ray curable composition of the present invention can be cured even when an ordinary photopolymerization initiator is not added thereto, but for enhancing the curing performance, a photosensitizer or a photoinitiation promoter such as tertiary amines and the like may be used. The photosensitizer includes, though not specifically limited thereto, thioxanthones such as 2,4-diethylthioxanthone, 2,4-diisopropylthioxanthone, etc.; benzophenones such as 4,4'-bis(diethylamino)benzophenone, etc.; anthraquinone, etc. On the other hand, the tertiary amine includes, also though not specifically limited thereto, ethyl p-dimethylaminobenzoate, isoamyl p-dimethylaminobenzoate, N,N-dimethylbenzylamine, etc. A high-molecular-weight compound branched with plural photosensitizers or tertiary amines via polyalcohols and the like in one molecule can also be suitably used. Preferably, the photoinitiation promoter is used in an amount of 0.03 to 20 parts by mass relative to the total amount of the active energy ray curable composition, more preferably 0.1 to 10 parts by mass.

Within a range not detracting from the advantageous effects of the present invention, any known photopolymerization initiator may also be used concurrently. Specifically, benzoin isobutyl ether, 2,4-diehtylthioxanthone, 2-isopropylthioxanthone, benzil, 2,4,6-trimethylbenzoyldiphenylphosphine oxide, 2-benzyl-2-dimethylamino-1-(4-morpholinophenyl)-butan-1-one, bis(2,6-dimethoxybenzoyl)2,4,4-trimethylpentyl phosphine oxide and the like are preferably used, and as other molecular cleavage-type ones than these, 1-hydroxycyclohexyl phenyl ketone, benzoin ethyl ether, benzyl dimethyl ketal, 2-hydroxy-2-methyl-1-phenylpropan-1-one, 1-(4-isopropylphenyl)-2-hydroxy-2-methylpropan-1-one, 2-methyl-1-(4-methylthiophenyl)-2-morpholinopropan-1-one and the like are also usable concurrently. Further, as a hydrogen-drawing photopolymerization initiator, benzophenone, 4-phenylbenzophenone, isophthalphenone, 4-benzoyl-4'-methyl-diphenyl sulfide or the like is also usable concurrently.

In the case where the active energy ray curable composition of the present invention is used for coating materials or inks, a colorant may be used. The colorant to be used may be any of dye or pigment, but from the viewpoint of the durability of prints, pigment is preferably used. In the case where such a colorant is added, if desired, a known conventional dispersant is preferably used.

The dye to be used in the present invention includes various dyes for use in ordinary inkjet recording, such as direct dyes, acid dyes, edible dyes, basic dyes, reactive dyes, disperse dyes, vat dyes, soluble vat dyes, reactive disperse dyes, etc.

The pigment for use in the present invent ion includes inorganic pigments and organic pigments. The inorganic pigments include chrome yellow, iron blue, barium sulfate, cadmium red, titanium oxide, zinc flower, alumina white, calcium carbonate, ultramarine, carbon black, graphite, red iron oxide, iron oxide, as well as carbon black produced according to a known method such as a contact method, a furnace method, a thermal method or the like.

As the organic pigments, various types of known conventional pigments are usable, including azo pigments (including azo lakes, insoluble azo pigments, condensed azo pigments, chelate azo pigments, etc.), polycyclic pigments (for example, phthalocyanine pigments, perylene pigments, perinone pigments, anthraquinone pigments, quinacridone pigments, dioxazine pigments, thioindigo pigments, isoindolinone pigments, quinophthalone pigments, etc.), dye chelates (for example, basic dye-type chelates, acid dye-type chelates, etc.), nitro pigments, nitroso pigments, aniline black, various types of fluorescent pigments, metal powder pigments, etc.

The mean particle size of the pigment is suitably planned depending on the use thereof. For example, in the case where the active energy ray curable composition of the present invention is applied to a printing ink such as an offset ink or the like, the mean particle size of the pigment preferably falls within a range of 10 to 500 nm, more preferably 50 to 300 nm or so.

On the other hand, for example, in the case where the active energy ray curable composition of the present invention is applied to an inkjet recording ink, the mean particle size of the pigment is preferably within a range of 10 to 200 nm, more preferably 50 to 150 nm or so. The amount of the colorant to be added is preferably within a range of 1 to 20% by mass of the total amount of the composition for securing a sufficient image density and sufficient lightfastness of printed images. The particle size of the pigment can be suitably controlled according to the pigment dispersant to be used and to the pigment dispersion method.

In the case where a pigment is used, a pigment dispersant is preferably used for the purpose of enhancing the dispersion stability relative to the above-mentioned active energy ray polymerizing compound, etc. Concretely, though not limited thereto, there are mentioned "Ajisper PB821", "PB822" and "PB817" all manufactured by Ajinomoto Fine-Techno Co., Ink.; "Solsperse 5000", "24000GR", "32000", "33000", "36000", "39000" and "44000" all manufactured by Lubrizol Corporation; "Disparlon DA-703-50", "DA-705" and "DA-725" all manufactured by Kusumoto Chemicals, Ltd.; "DZSPERBYK111", "YK168" and "YK180" all manufactured by BYK Japan KK, etc. The amount of the pigment dispersant to be used is preferably within a range of 3 to 80% by mass relative to the pigment, more preferably within a range of 5 to 60% by mass. When the amount is less than 3% by mass, the dispersion stability tends to be insufficient, but when more than 80% by mass, the ink viscosity tends to increase.

Further, if desired and within a range not overstepping the object of the present invention and especially within a range capable of securing storage stability, heat resistance, and solvent resistance, any other component may be incorporated. As the other component, for example, various coupling agents; antioxidants; polymerization inhibitors; stabilizers; fillers and the like may be added.

The coupling agent is a compound that chemically binds two of inorganic materials and organic materials or improves affinity of the two, as accompanied by chemical reaction, to thereby enhance the function of composite materials, and for example, includes silane compounds such as γ-(2-aminoethyl)aminopropyltrimethoxysilane, γ-(2-aminoethyl)aminopropylmethyldimethoxysilane, γ-methacryloxypropyltrimethoxysilane, γ-glycidoxypropyltrimethoxysilane, etc.; titanium compounds such as tetra-isopropoxytitanium, tetra-n-butoxytitanium, etc.; aluminum compounds such as aluminum isopropylate, etc. The amount of the compound to be added may be 0.1 to 10 parts by mass relative to 100 parts by mass of the active energy ray curable composition of the present invention, preferably 0.2 to 5 parts by mass.

The antioxidant includes phenolic antioxidants such as 2,6-di-t-butyl-p-cresol, butylated hydroxyanisole, 2,4,6-tri-t-butylphenol, 2,2'-methylene-bis(4-methyl-6-t-butylphenol), etc.; antioxidant of 2,2,6,6-tetramethylpiperidine derivative that is referred to as HALS, and phosphorus or sulfur-containing secondary antioxidants. On the other hand, the polymerization inhibitor includes nitrosoamine salts, etc., but not limited thereto. One alone or two or more of these antioxidants and polymerization inhibitors may be used either singly or as combined. The amount of the compound to be added may be 0.01 to 2.0 parts by mass relative to 100 parts by mass of the active energy ray curable composition of the present invention, preferably 0.03 to 1.0 part by mass.

The active energy ray curable composition of the present invention may be used in the absence of a solvent, but if desired, a suitable solvent may be used. Not specifically limited, the solvent may be any one that does not react with the above-mentioned components, and one alone or two or more of solvents may be used either singly or as combined.

(Production Method)

For obtaining the active energy ray curable resin composition of the present invention, the above-mentioned components may be mixed, and the mixing order and method are not specifically defined. For example, the above-mentioned components are mixed in a range of room temperature to 100° C., using a kneading, mixing or preparing machine such as a kneader, a three-roll mill, a sand mill, a gate mixer, an ultrasonic homogenizer, a high-pressure homogenizer, a paint shaker, a sand grinder, a dyno-mill, a disper mat, a bead mill, an SC mill, a nanomizer, etc.

(Curing Method)

The active energy ray curable resin composition of the present invention can be polymerized/cured with active energy rays. The active energy rays for use herein include ionizing radiations such as UV rays, electron beams, α rays, β-rays and γ-rays; microwaves, high-frequency waves, visible rays, IR rays, laser beams, etc. Above all, UV rays are preferred.

UV rays having a wavelength of 180 to 400 nm are effective, and above all, those having a wavelength of 254 nm, 308 nm, 313 nm or 365 nm are effective for curing the active energy ray curable composition and the active energy ray curable ink composition of the present invention.

The light source includes, for example, low-pressure mercury lamp, high-pressure mercury lamp, ultra-high-pressure mercury lamp, metal halide lamp, chemical lamp, black light lamp, mercury-xenon lamp, excimer lamp, short arc lamp, helium/cadmium laser, argon laser, excimer laser, LED lamp.

The UV irradiation dose could not be indiscriminately determined as influenced by the type of the light source to be used and the amount of the Michael addition reaction product of the present invention to be used, but is, from the viewpoint of productivity, preferably within a range of 10 to 2000 J/m$^2$.

(Use)

The active energy ray curable composition of the present invention is usable in various applications utilizing polymerization or crosslinking reaction, including printing inks, inkjet recording inks, coating materials, molding resins, casting resins, photofabrication resins, sealants, polymerization resins for dental use, light-sensitive resins for printing plates, color proof for printing, resists for color filters, resists for black matrices, photospacers for liquid crystals, screen materials for rear projections, optical fibers, rib materials for plasma displays, dry film resists, resists for printing boards, solder resists, photoresists for semiconductors, resists for microelectronics, resists for manufacture of parts for micromachines, etching resists, microlens arrays, insulating materials, hologram materials, optical switches, materials for waveguides, overcoating materials, powder coatings, adhesives, pressure-sensitive adhesives, mold lubricants, optical recording media, sticky adhesives, release coating agents, compositions for image recording materials using microcapsules, various devices, etc.

In particular, the active energy ray curable composition of the present invention is free from coating film odor, extracts from cured coating film and ink migration that have heretofore been problematic, and is extremely effective from the aspect of safety and good hygiene, and is widely offered to various wrapping and packing applications, for example, for packaging foods, toys, sanitary cosmetics, medicines, etc. For example, the composition is favorably used as adhesives for lamination, coating materials, printing inks for offset printing, gravure printing, flexographic printing, silk screen printing or the like, as well as inkjet-recording inks, etc.

(Use in Coating Material)

In the case where the active energy ray curable composition of the present invention is used as a coating material, various additives of a flowability regulating agent such as silicone, polyamide or the like, inorganic fine particles such as silica, titanium oxide, zinc oxide or the like, various types of leveling agents of silicone-type, fluorine-containing, acrylic ones, a UV absorbent, a dripping inhibitor, a viscosity improver and the like may be added thereto in ordinary quantities, in addition to the above-mentioned additives and colorant.

(Use in Printing Ink)

In the present invention, a printing ink is a general term for ink for use in a printing method using a printing plate.

In the case where the active energy ray curable composition of the present invention is used as a printing ink, various binder resins may be used in addition to the above-mentioned additives and colorant. The binder resin as referred to herein indicates a general sense of resin that has suitable pigment affinity and dispersibility and has rheological characteristics required for a printing ink, and for example, as a nonreactive resin thereof, there are mentioned diallyl phthalate resins, epoxy resins, polyurethane resins, polyester resins, petroleum resins, rosin ester resins, poly(meth)acrylates, cellulose derivatives, vinyl chloride-vinyl acetate copolymers, polyamide resins, polyvinyl acetal resins, butadiene-acrylonitrile copolymers, etc.; and in addition, epoxyacrylate compounds, urethane acrylate compounds, polyester acrylate compounds and the like having at least one or more polymerizing groups in the resin molecule are also usable. One alone or two or more of these binder resin compounds may be used either singly or as combined.

For example, in the case of using in an offset ink, a composition containing 1 to 70 parts by mass of the above-mentioned pigment and 3 to 70 parts by mass of the above-mentioned binder resin in 100 parts by mass of a mixture of the Michael addition reaction product of the present invention and the above-mentioned photocurable reactive compound can be used. From the viewpoint of balance between the color density of prints and printing aptitude, it is desirable that the amount of the pigment is 5 to 30 parts by mass and that of the binder resin is 5 to 50 parts by mass relative to 100 parts by mass of the mixture of the Michael addition reaction product of the present invention and the photocurable reactive compound. Preferably, the offset ink to be produced in the manner as above is so planned as to have generally 3 to 200 Pa·s (25° C.), though depending on the printing device to be used.

In the case of multicolor printing with offset inks, the active energy ray curable composition of the present invention may be used in one color ink of four process color inks of yellow, magenta, cyan and black, or may be used in all of those color inks. For example, in the case where the print is for food packaging use, it is desirable that the active energy ray curable composition of the present invention is used in all color inks for preventing migration as much as possible.

If desired, various additives for offset ink may be used. As a typical additive for the purpose of imparting rub resistance, antiblocking performance, slidability and scratch resistance, for example, there are mentioned paraffin wax, polyethylene wax, polypropylene wax, polytetrafluoroethylene wax, a silicone compound, etc. In addition, in accordance with required performances, other additives of a UV absorbent, an IR absorbent, a microbicide and the like may also be added. The amount of these additives to be added may be 0 to 10 parts by mass relative to 100 parts by mass of the total amount of the composition.

(Use in Inkjet Recording Ink)

On the other hand, in the case where the active energy ray curable composition of the present invention is used for an inkjet recording ink not using a printing plate, a composition containing 0.1 to 30 parts by mass of a pigment, 0 to 20 parts by mass of the above-mentioned binder resin and 40 to 90 parts by mass of a (meth)acrylate derivative and/or a low-viscosity monomer relative to 100 parts by mass of the active energy ray curable composition can be used. From the viewpoint of balance between the color density of prints and printing aptitude, it is desirable that the amount of the pigment is 0.2 to 20 parts by mass, that of the binder resin is 0 to 10 parts by mass relative to 100 parts by mass and that of the acrylate derivative and/or low-viscosity monomer is 50 to 80 parts by mass relative to 100 parts by mass of the active energy ray curable composition. Preferably, the inkjet recording ink to be produced in the manner as above is so planned as to have generally 1 to 100 mPa·s (25° C.), though depending on the inkjet device to be used.

In the case where the active energy ray curable inkjet recording ink is used for multicolor printing and where a deep color or pale color ink of the same color series is added to the ink to be used, for example, to each of the four process color inks of yellow, magenta, cyan and black, the active energy ray curable composition of the present invention may be used in one color of magenta and pale light magenta and deep red in addition thereto, cyan and pale light cyan and deep blue in addition thereto, and black and pale gray, light black and deep mat black in addition thereto, or may be used in all of those color inks.

In addition, if desired but within a range not detracting from jetting stability, a surfactant, a leveling additive, a mat agent, as well as any of polyester resins, polyurethane resins, vinylic resins, acrylic resins, rubber resins and waxes for controlling film properties may be added.

EXAMPLES

Hereinunder the present invention is described in more detail with reference to Examples, but the present invention is not restricted by these Examples.

[$^1$H-NMR Measurement Condition]
  Apparatus: JEOL's FT-NMR, JNM-LA300 (300 MHz)
  Measurement solvent: heavy chloroform (CDCl$_3$-dl)
  Internal standard substance: tetramethylsilane (TMS)

[Synthesis of Compound (A) (Intermediate)]

(Example 1) Synthesis of Compound (5') (2-dimethylamino-1-(4-morpholinophenyl)-2-(4-carboxybenzyl)butan-1-one

[Step 1]

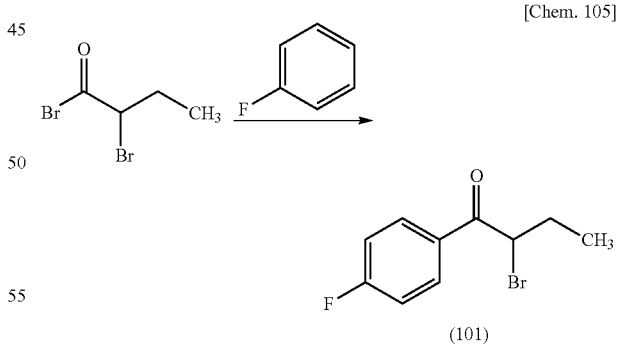

[Chem. 105]

(101)

121.8 g of aluminum chloride (anhydride) and 300 mL of dewatered dichloromethane were put into a 1-L four-neck flask equipped with a stirrer, a thermometer, a nitrogen-introducing tube, an alkali trap and a dropping funnel, and cooled with ice in an ice bath in a nitrogen stream atmosphere. 200 g of 2-bromobutyryl bromide was added thereto. A mixed solution of 83.6 g of fluorobenzene and 100 mL of dewatered dichloromethane was dropwise added to the foregoing flask through the dropping funnel, taking 20 minutes. After the addition, the ice bath was removed, and this was kept stirred as such for 2 hours.

After the stirring, the reaction liquid was put into 1 L of water with ice, and kept stirred for 2 hours. After left to stand as such, this was subjected to liquid-liquid separation and the lower layer was collected. This was washed twice with 2N hydrochloric acid, washed once with an aqueous saturated sodium hydrogencarbonate solution, and washed twice with a saturated saline solution. This was dried over magnesium sulfate for 24 hours, and then dichloromethane was evaporated out under reduced pressure to give 2-bromo-1-(4-fluorophenyl)-1-butanone (101).

Actual yield: 214.3 g, percent yield: 100%

$^1$H-NMR (CDCl$_3$): 1.11 ppm (t, 3H, —C$\underline{H}_3$), 2.20 ppm (m, 2H, —C$\underline{H}_2$—), 5.04 ppm (dd, 1H, Br—C$\underline{H}$), 7.19 ppm (m, 2H, aromatic), 8.07 ppm (m, 2H, aromatic)

[Step 2]

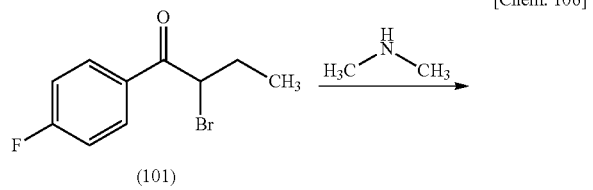

(101)

789.9 g of 11% dimethylamine/ethanol solution was put into a 2-L four-neck flask equipped with a stirrer and a thermometer, and cooled with ice in an ice bath. 157.7 g of the intermediate (101) was dropwise added thereto via a dropping funnel, taking 30 minutes. After the addition, the ice bath was removed, and kept stirred as such for 24 hours. After the stirring, ethanol was evaporated out, and toluene was added. This was washed with water, and the upper layer was made to have a pH of 1 using 2 N hydrochloric acid, this was subjected to liquid-liquid separation, and the lower layer was collected. The collected lower layer was made to have a pH of 12 by using an aqueous 10% sodium hydroxide solution, then toluene was added thereto, and the upper layer was collected. This was further washed twice with a saturated saline solution, the upper layer was collected, and dried over magnesium sulfate for 24 hours. Toluene was evaporated away under reduced pressure to give the intermediate (102).

Actual yield: 134.6 g. percent yield: 100%

$^1$H-NMR (CDCl$_3$): 0.85 ppm (t, 3H, —C$\underline{H}_3$), 1.71 ppm (m, 1H, —C$\underline{H}_2$—), 1.92 ppm (m, 1H, —C$\underline{H}_2$—), 2.31 ppm (s, 6H, N—C$\underline{H}_3$), 3.77 ppm (M, 1H, —C$\underline{H}$—), 7.11 ppm (m, 2H, aromatic) 8.10 ppm (m, 2H, aromatic)

[Step 3]

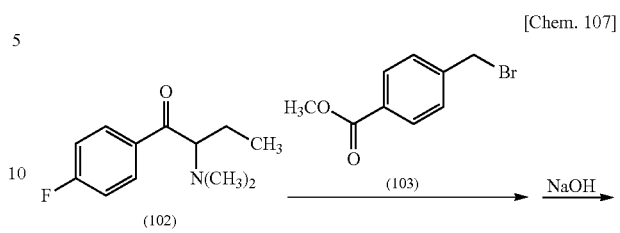

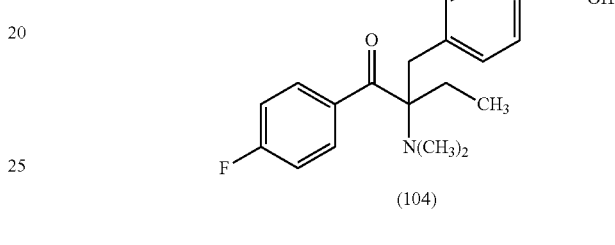

(104)

79.5 g of the intermediate (102), 87.0 g of methyl 4-(bromomethyl)benzoate (103) and 120 mL of IPA were put into a 500-mL four-neck flask equipped with a stirrer, a thermometer and a condenser tube, and stirred for 24 hours at 50° C. Subsequently, 105 mL of an aqueous 8 M sodium hydroxide solution was added, and stirred at 50° C. for 1 hour. After the stirring, this was controlled at a pH of 6 using an aqueous hydrochloric acid solution, then IPA was evaporated out, and the precipitated crystal was taken out through filtration to give the precipitate (104).

Actual yield: 110.9 g, percent yield: 85.0%

$^1$H-NMR (CDCl$_3$): 0.61 ppm (t, 3H, —C$\underline{H}_3$), 1.87 ppm (m, 1H, —C$\underline{H}_2$—), 2.03 ppm (m, 1H, —C$\underline{H}_2$—), 2.36 ppm (s, 6H, N—C$\underline{H}_3$), 3.25 ppm (dd, 2, —C$\underline{H}_2$-Ph), 7.06 ppm (dd, 2H, aromatic), 7.41 ppm (d, 2H, aromatic), 8.00 ppm (d, 2H, aromatic), 8.40 ppm (dd, 2H, aromatic)

[Step 4]

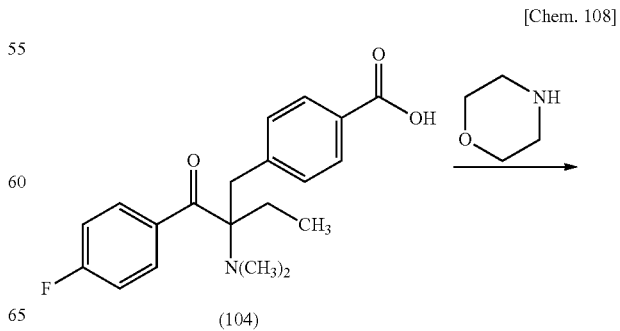

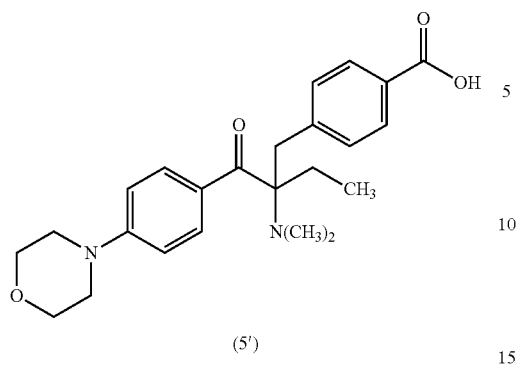

(5')

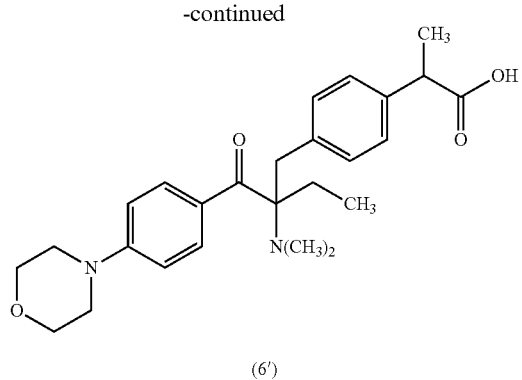

(6')

34.3 g of the intermediate (104), 35 mL of dimethyl sulfoxide (DMSO) and 70 mL of morpholine were added to a 1-L four-neck flask equipped with a stirrer, a thermometer and a condenser tube, and heated at 100*C in a nitrogen stream atmosphere for 24 hours. After the reaction, this was neutralized with 6 N hydrochloric acid to have a pH of 6, and then extracted with toluene. This was washed twice with water, and then dried over magnesium sulfate for 24 hours. Toluene was evaporated out under reduced pressure, and the residue was crystallized from ethyl acetate and hexane to give the compound (5') (2-dimethylamino-1-(4-morpholinophenyl)-2-(4-carboxybenzyl)butan-1-one.

Actual yield: 39.0 g, percent yield: 95.1%

$^1$H-NMR (CDCl$_3$): 0.64 ppm (t, 3H, —CH$_3$), 1.83 ppm (m, 1H, —CH$_2$—), 2.00 ppm (m, 1H, —CH$_2$—), 2.35 (s, 6H, N—CH$_3$), 3.26 (m, 2H, —CH$_2$-Ph), 3.30 ppm (m, 4H, Morpholine), 3.84 ppm (m, 4H, Morpholine), 6.82 ppm (d, 2H, aromatic), 7.39 ppm (d, 2, aromatic), 7.95 ppm (d, 2H, aromatic), 8.35 ppm (d, 2H, aromatic)

(Example 2) Synthesis of Compound (6') (2-dimethylamino-1-(4-morpholinophenyl)-2-(4-(1-hydroxy-1-oxopropan-2-yl)benzyl)butan-1-one)

The compound (6') (2-dimethylamino-1-(4-morpholinophenyl)-2-(4-(1-hydroxy-1-oxopropan-2-yl)benzyl)butan-1-one) was synthesized through reaction according to the method described in Example 1, except that in the step 1 in Example 1, 97.6 g of methyl 2-(4-bromomethyl)phenylpropionate (105) was used in place of 87.0 g of methyl 4-(bromomethyl)benzoate (103).

$^1$H-NMR (CDCl$_3$): 0.66 ppm (t 3H, —CH$_3$), 1.46 (d, 3H, CH—CH$_3$), 1.83 ppm (m, 1H, —CH$_2$—), 2.00 ppm (m, 1H, —CH$_2$—), 2.35 (s, 6H, N—CH$_3$), 3.16 (s, 2H, —CH$_2$-Ph), 3.30 ppm (m, 4H, Morpholine), 3.67 (q, 1H, CH—CH$_3$), 3.84 ppm (m, 4H, Morpholine), 6.82 ppm (d, 2H, aromatic), 7.39 ppm (d, 2H, aromatic), 7.95 ppm (d, 2H, aromatic), 8.35 ppm (d, 2H, aromatic)

(Example 3) Synthesis of Compound (8') [2-methyldodecylamino-1-(4-morpholinophenyl)-2-(4-carboxybenzyl)butan-1-one]

[Chem. 110]

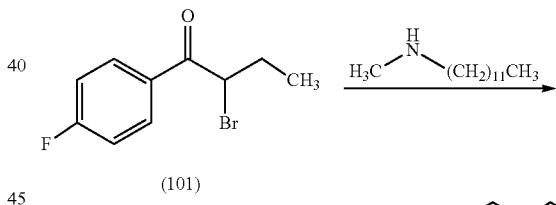

[Chem. 109]

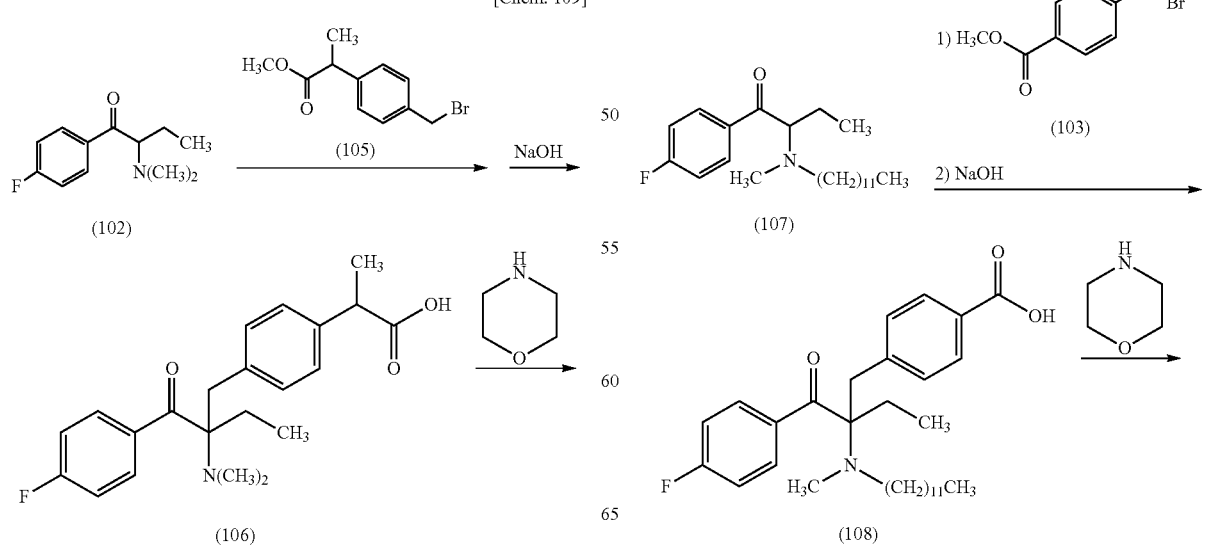

-continued

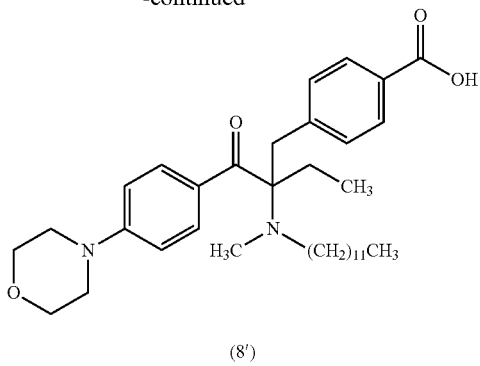

(8')

The compound (8') (2-methyldodecylamino-1-(4-morpholinophenyl)-2-(4-carboxybenzyl)butan-1-one) was synthesized according to the method described in Example 1, except that in the step 1 in Example 1, 256.6 g of methyldodecylamine was used in place of 789.9 q of 11% dimethylamine/ethanol solution.

$^1$H-NMR (CDCl$_3$): 0.66 ppm (t, 3H, —CH$_3$), 0.84 ppm (t, 3H, —CH$_3$), 1.20 ppm (m, 18H, —CH$_2$—), 1.34 ppm (m, 2H, N—CH$_2$—CH$_2$—CH$_2$—), 1.83 ppm (m, 1H, —CH$_2$—), 2.00 ppm (m, 1H, —CH$_2$—) 2.30 (s, 3H, N—CH$_3$), 2.40 (m, 1H, N—CH$_2$—), 2.60 (m, 1H, N—CH$_2$—), 3.10 (s, 2H, —CH$_2$-Ph), 3.30 ppm (m, 4H, Morpholine), 3.84 ppm (m, 4H, Morpholine), 6.82 ppm (d, 2H, aromatic), 7.39 ppm (d, 2H, aromatic), 7.95 ppm (d, 2H, aromatic), 8.35 ppm (d, 2H, aromatic)

(Example 4) Synthesis of Compound (10') [2-dimethylamino-1-(4-(4-methylpiperazinyl)phenyl)-2-(4-carboxybenzyl)butan-1-one]

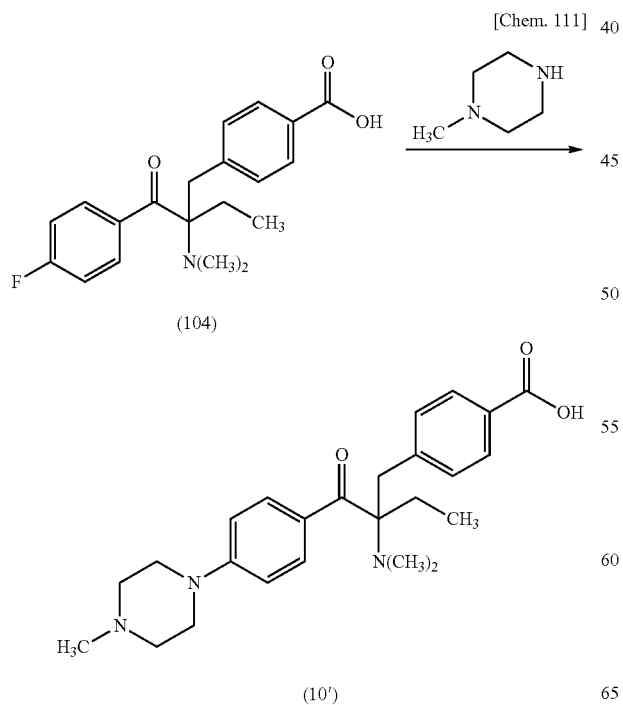

The compound (10') (2-dimethylamino-1-(4-(4-methylpiperazinyl)phenyl)-2-(4-carboxybenzyl)butan-1-one) was synthesized according to the method described in Example 1, except that in the step 3 in Example 1, 70 mL of 4-methylpiperazine was used in place of 70 mL of morpholine.

$^1$H-NMR (CDCl$_3$): 0.64 ppm (t, 3H, —CH$_3$), 1.83 ppm (m, 1H, —CH$_2$—), 2.00 ppm (m, 1H, —CH$_2$—), 2.35 (s, 6H, N—CH$_3$), 2.51 (m, 4H, 1-MethylPiperazine), 3.26 (m, 2H, —CH$_2$-Ph), 3.38 (m, 4H, 1-MethylPiperazine), 3.55 (br, 4H, Piperazine), 6.82 ppm (d, 2H, aromatic), 7.39 ppm (d, 2H, aromatic), 7.95 ppm (d, 2H, aromatic), 8.35 ppm (d, 2H, aromatic)

(Example 5) Synthesis of Compound (5') [2-dimethylamino-1-(4-morpholinophenyl)-2-(4-carboxybenzyl)butan-1-one (5')]

[Step 1]

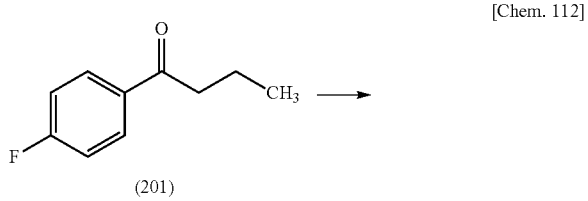

500 g of 4-fluorobutyrophenone (201), 250 mL of dimethyl sulfoxide (DMSO) and 1000 mL of morpholine were put into a 5-L flask equipped with a stirrer, a thermometer, a nitrogen-introducing tube, a condenser tube and an alkali trap, and reacted with stirring at 95° C. in nitrogen for 2 days. For tracing the reaction, the conversion ratio was confirmed through gas chromatography. After left cooled, 1.4 L of toluene and 2.1 L of water were added and left to stand as such for liquid-liquid separation, and subsequently the organic layer was washed three times with water, and then toluene was evaporated away under reduced pressure. 700 mL of isopropanol was added to the resultant residue with stirring, then the crystal precipitated out under cooling with ice was taken out through filtration, and dried under reduced pressure to give 1-(4-morpholinophenyl)-1-butanone (202).

Actual yield: 597 g, percent yield: 85%

$^1$H-NMR (CDCl$_3$): 1.01 ppm (t, 3H, —CH$_3$), 1.76 ppm (m, 2H, —CH$_2$—), 2.86 ppm (t, 2H, CO—CH$_2$—), 3.30 ppm (m, 4H, morpholine), 3.85 ppm (m, 4H, morpholine), 6.88 ppm (d, 2H, aromatic), 7.89 ppm (d, 2H, aromatic)

[Step 2]

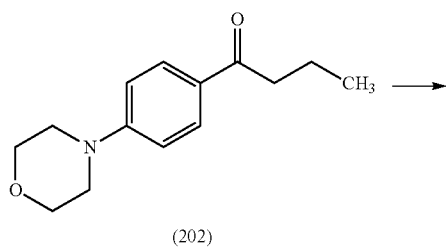

(202)

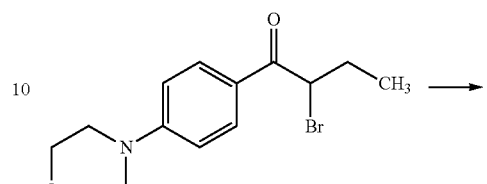

(203)

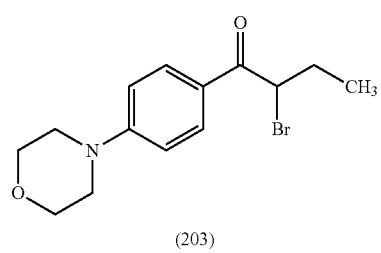

(203)

348 g of 1-(4-morpholinophenyl)-1-butanone (202) and 348 mL of methylene chloride were put into a 3-L flask equipped with a stirrer, a thermometer, a nitrogen-introducing tube, a condenser tube, a dropping funnel and an alkali trap, and with cooling with ice in nitrogen, 724 g of 25% hydrogen bromide-acetic acid solution was dropwise added thereto, taking 1 hour. After complete addition, 238 g of bromine was dropwise added taking 1 hour, with keeping a temperature not higher than 10° C., and stirred for 1 hour at the temperature to complete the reaction. 2 L of water was added, this was neutralized with sodium hydroxide, and the precipitated crystal of the product was dissolved by adding 1.5 L of methylene. The organic layer was washed once with 5% sodium hydrogencarbonate, once with water and once with an aqueous saturated sodium hydroxide solution, and then methylene chloride was evaporated out under reduced pressure. 1.5 L of hexane was added, this was cooled with ice, and the precipitated crystal was taken out through filtration and dried to give 1-(4-morpholinophenyl)-2-bromo-1-butanone (203).

Actual yield: 438 g, percent yield: 94%

$^1$H-NMR (CDCl$_3$): 1.06 ppm (t, 3H, —CH$_3$), 2.17 ppm (m, 2H, —CH$_2$—), 3.33 ppm (m, 4H, morpholine), 3.84 ppm (m, 4H, morpholine), 5.04 ppm (m, 1H, CO—CH—Br), 6.88 ppm (d, 2H, aromatic), 7.96 ppm (d, 2H, aromatic)

[step 3]

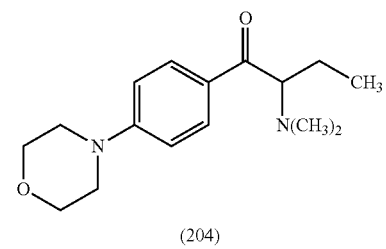

(204)

290 g of 1-(4-morpholinophenyl)-2-bromo-1-butanone (203) and 870 mL of 2-butanone were put into a 3-L flask equipped with a stirrer, a thermometer, a condenser tube and a dropping funnel, and with cooling with ice, 251 g of an aqueous 50% dimethylamine solution was dropwise added at 5 to 10° C., and stirred at the temperature for 5 hours to complete the reaction. The organic layer was washed four times with 500 mL of water, and 2-butanone was evaporated away under reduced pressure to give a crude product containing 2-dimethylamino-1-(4-morpholinophenyl) butan-1-one (204). Without any precipitation, the resultant crude product was used in the next step. A part of the crude product was sampled and recrystallized in hexane to give a pale yellow crystal, 2-dimethylamino-1-(4-morpholinophenyl) butan-1-one (204).

$^1$H-NMR (CDCl$_3$): 0.85 ppm (t, 3H, —CH$_3$), 1.71 ppm (m, 1H, —CH$_2$—), 1.87 ppm (m, 1H, —CH$_2$—), 2.32 ppm (s, 6H, N—CH$_3$), 3.31 ppm (m, 4H, morpholine), 3.83 ppm (m, 4H, morpholine), 3.87 ppm (d, 2H, aromatic), 8.00 ppm (d, 2H, aromatic)

[Step 4]

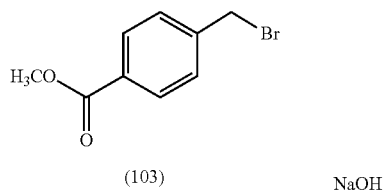

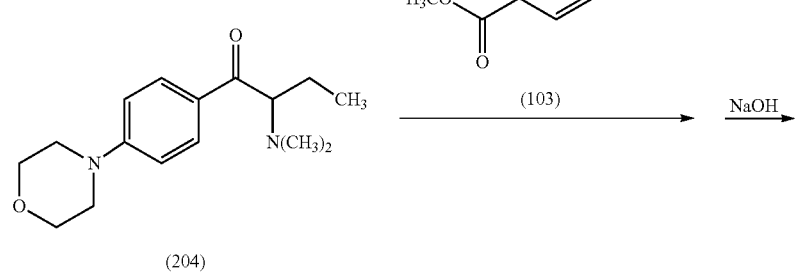

(204)

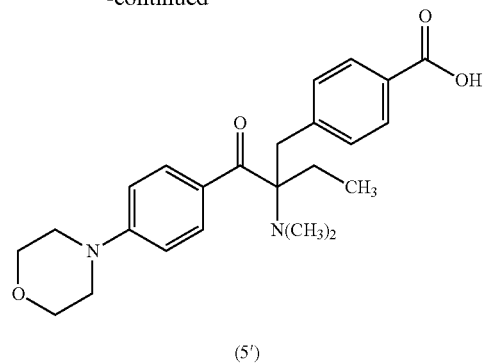

(5')

Figure 3:
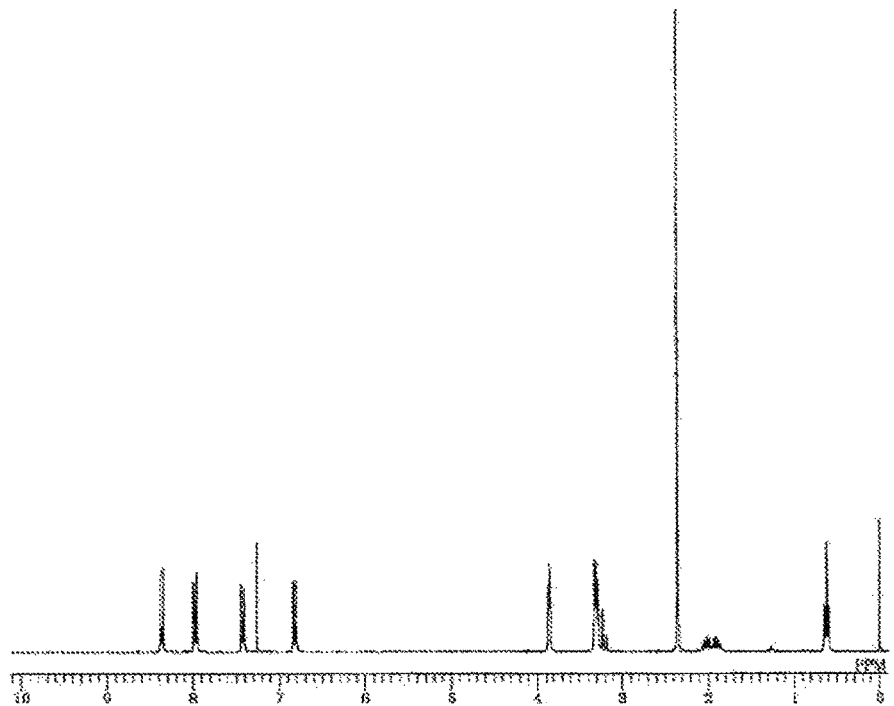
FIG. 3 shows a $^1$H-NMR chart of the compound (5') obtained in Example 5.

2-Dimethylamino-1-(4-morpholinophenyl)butan-1-one (204) obtained in the above, 256 g of methyl 4-(bromomethyl)benzoate (103) and 510 ml of IPA were put into a 3-L flask equipped with a stirrer, a thermometer and a condenser tube, and stirred at 50° C. for 3 hours. Subsequently, 232 mL of an aqueous 8 M sodium hydroxide solution was added and stirred at 50° C. for 1 hour. After the stirring, this was made to have a pH of 5.7 with an aqueous hydrochloric acid solution, and then IPA was evaporated out. The concentrated residue was extracted with ethyl acetate, and washed twice with water and once with a saturated saline solution. Ethyl acetate was evaporated away under reduced pressure, and the crystal precipitated out by addition of hexane was taken out through filtration, and dried under reduced pressure to give the compound (5') (2-dimethylamino-1-(4-morpholinophenyl)-2-(4-carboxybenzyl)butan-1-one) The $^1$H-NMR chart of the resultant compound (5') is shown in FIG. 3.

Actual yield: 290.0 g, percent yield: 76.0%

$^1$H-NMR (CDCl$_3$): 0.62 ppm (t, 3H, —C$\underline{H_3}$), 1.85 ppm (m, 1H, —C$\underline{H_2}$—), 2.01 ppm (m, 1H, —C$\underline{H_2}$—) 2.35 ppm (s, 6H, N—C$\underline{H_3}$), 3.25 ppm (dd, 2H, —C$\underline{H_2}$-Ph), 3.30 ppm (m, 4H, morpholine), 3.86 ppm (m, 4H, morpholine), 6.82 ppm (d, 2H, aromatic), 7.42 ppm (d, 2H, aromatic), 7.97 ppm (d, 2H, aromatic), 8.37 ppm (d, 2H, aromatic)

(Example 6) Synthesis of Compound (8') [2-methyldodecylamino-1-(4-morpholinophenyl)-2-(4-carboxybenzyl)butan-1-one]

[Chem. 116]

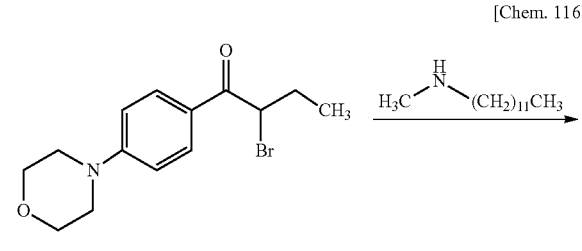

(203)

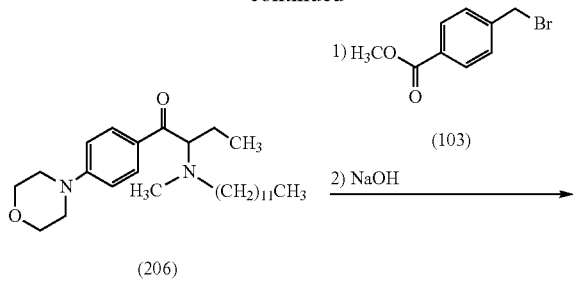

(206)

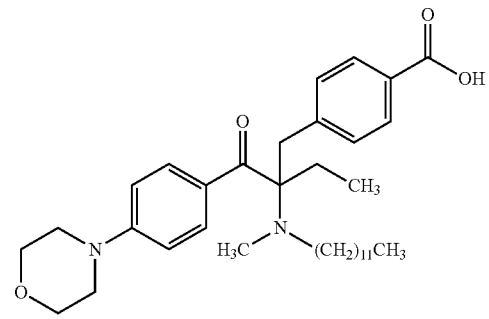

(8')

Figure 4:
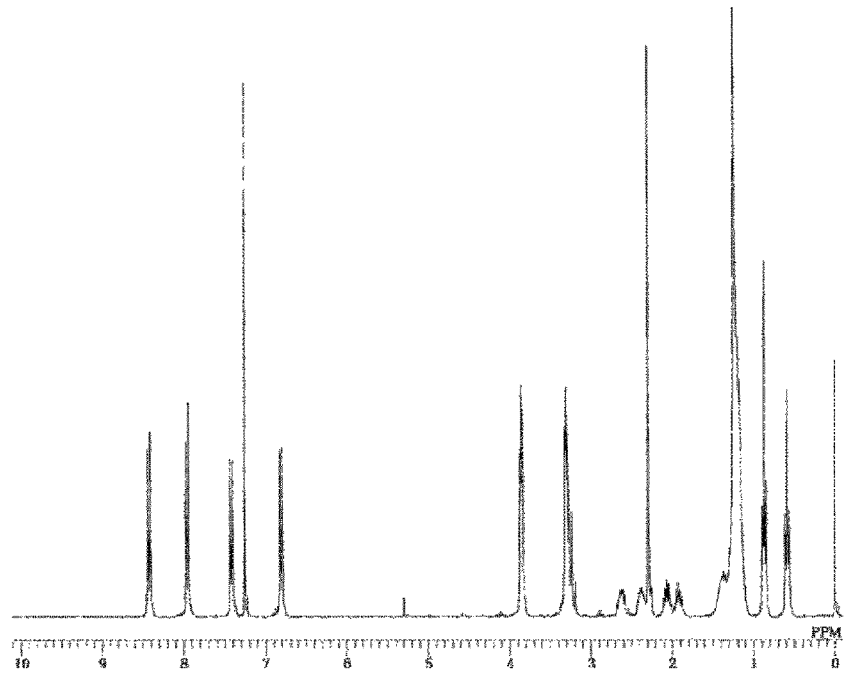
FIG. 4 shows a $^1$H-NMR chart of the compound (8') obtained in Example 6.

The compound (8') (2-methyldodecylamino-1-(4-morpholinophenyl)-2-(4-carboxybenzyl)butan-1-one) was produced in the same manner as in Example 5 except that, in the step 3 in Example 5, methyldodecylamine was used in place of the aqueous 50% dimethylamine solution. The $^1$H-NMR chart of the resultant compound (8') is shown in FIG. 4.

Actual yield: 231 g, percent yield: 44%

$^1$H-NMR (CDCl3): 0.62 ppm (t, 3H, —CH3), 0.86 ppm (t, 3H, —CH$_3$), 1.20 ppm (m, 18H, —CH$_2$—), 1.34 ppm (m, 2H, N—CH$_2$—CH$_2$—CH$_2$—), 1.45 ppm (d, 3H, CH—CH$_3$), 1.91 ppm (m, 1H, —CH$_2$—), 2.08 ppm (m, 1H, —CH2-), 2.30 ppm (s, 3H, N—CH$_3$), 2.40 (m, 1H, N—CH$_2$—), 2.65 (m, 1H, N—CH$_2$—), 3.25 ppm (dd, 2H, —CH2-Ph), 3.30 ppm (m, 4H, morpholine), 3.86 ppm (m, 4H, morpholine), 6.82 ppm (d, 2H, aromatic), 7.42 ppm (d, 2H, aromatic), 7.97 ppm (d, 2H, aromatic), 8.37 ppm (d, 2H, aromatic)

(Example 7) Synthesis of Compound (11') [2-methyldodecylamino-1-(4-methylpiperazinophenyl-2-(4-(1-hydroxy-1-oxopropan-2-yl)benzyl)butan-1-one]

[Step 1]

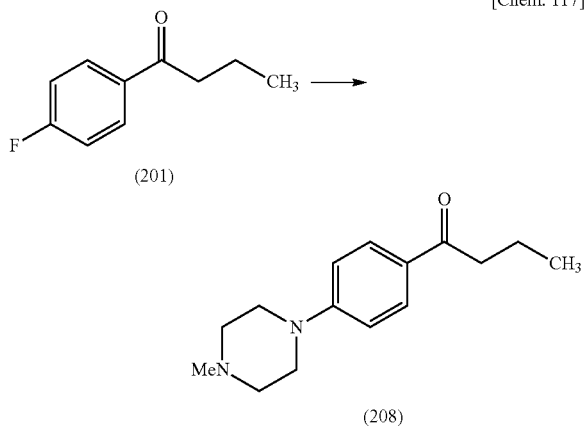

[Chem. 117]

(201)

(208)

50 g of 4-fluorobutyrophenone (201), 25 mL of dimethyl sulfoxide (DMSO) and 100 mL of 4-methylpiperazine were put into a 500-mL flask equipped with a stirrer, a thermometer, a nitrogen-introducing tube and a condenser tube, and reacted with stirring at 95° C. in nitrogen for 2 days. After left cooled, 150 mL of toluene and 250 mL of water were added and left to stand as such for liquid-liquid separation, and subsequently, the organic layer was washed three times with water, and then toluene was evaporated away under reduced pressure. The resultant residue was purified through silica gel chromatography to give 1-(4-methylpiperazinophenyl)-1-butanone (208).

Actual yield: 71.1 g, percent yield: 96%

$^1$H-NMR (CDCl$_3$): 1.01 ppm (t, 3H, —CH$_3$), 1.76 ppm (m, 2H, —CH$_2$—), 2.33 ppm (s, 3, —NCH$_3$), 2.55 ppm (m, 4H, methylpiperazine), 2.86 ppm (t, 2H, CO—CH$_2$—), 3.32 ppm (m, 4H methylpiperazine), 6.86 ppm (d, 2H, aromatic), 7.87 ppm (d, 2H, aromatic)

[Step 2]

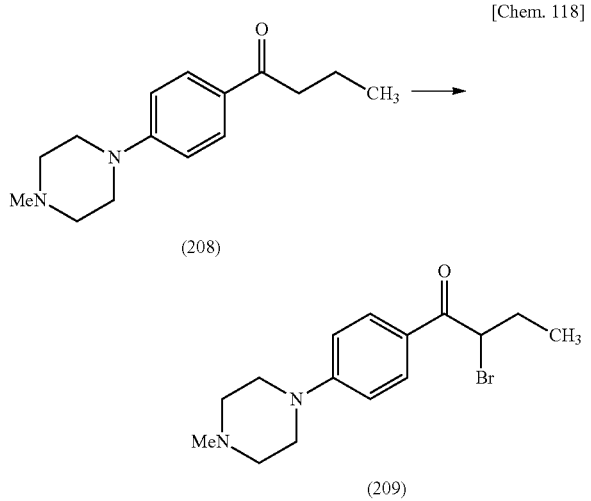

[Chem. 118]

(208)

(209)

34.8 g of 1-(4-methylpiperazinophenyl)-1-butanone (208) and 35 mL of methylene chloride were put into a 500-mL flask equipped with a stirrer, a thermometer, a nitrogen-introducing tube, a condenser tube, a dropping funnel and an alkali trap, cooled with ice in nitrogen, and 72.4 g of 25% hydrogen bromide-acetic acid solution was added thereto, taking 1 hour. After complete addition, 33.9 g of bromine was dropwise added thereto, taking 1 hour with keeping at a temperature not higher than 10° C., and this was stirred at the temperature for 1 hour to complete the reaction. 200 mL of water was added, this was neutralized with sodium hydroxide, and the precipitated crystal of the product was dissolved by adding 150 mL of methylene chloride thereto. The organic layer was washed once with 5% sodium hydrogencarbonate, once with water and once with an aqueous saturated sodium hydroxide solution, and then methylene chloride was evaporated away under reduced pressure. 150 mL of hexane was added, this was cooled with ice, and the precipitated crystal was taken out through filtration and dried to give 1-(4-methylpiperazinophenyl)-2-bromo-1-butanone (209).

Actual yield: 42.3 g, percent yield: 92%

$^1$H-NMR (CDCl$_3$): 1.06 ppm (t, 3H, —CH$_3$), 2.16 ppm (m, 2H, —CH$_2$—), 2.30 ppm (s, 3H, —NCH$_3$), 2.52 ppm (m, 4H, methylpiperazine), 3.32 ppm (m, 4H, methylpiperazine), 5.04 ppm (m, 1H, CO—CH—Br), 6.81 ppm (d, 2H, aromatic), 7.95 ppm (d, 2H, aromatic)

[Step 3]

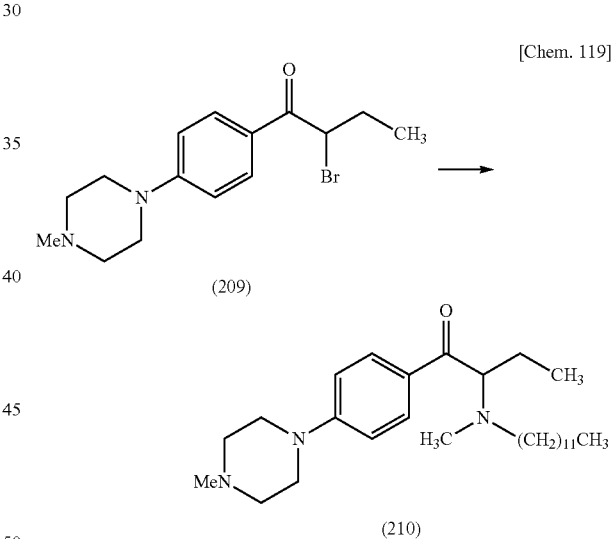

[Chem. 119]

(209)

(210)

30.0 g of 1-(4-methylpiperazinophenyl)-2-bromo-1-butanone (209), 46.0 g of methyldodecylamine and 90 mL of acetonitrile were put into a 300-mL flask equipped with a stirrer, a thermometer, a condenser tube and a dropping funnel, and stirred at 50° C. for 20 hours to complete the reaction. 100 mL, of ethyl acetate was added, the precipitated salt was separated through filtration, the filtrate was washed with water, and the organic solvent was evaporated away under reduced pressure to give a crude product containing (2-methyldodecylamino-1-(4-methylpiperazinophenyl)butan-1-one (210). Purifying through silica gel chromatography gave pale yellow oily 2-methyldodecylamino-1-(4-methylpiperazinophenyl)butan-1-one (210).

Actual yield: 27.8 g, percent yield: 68%

$^1$H-NMR (CDCl$_3$): 0.66 ppm (t, 3H, —CH$_3$), 0.86 ppm (t, 3H, —CH$_3$), 1.20 ppm (m, 18H, —CH$_2$—) 1.34 ppm (m, 2H, N—CH$_2$—CH$_2$—CH$_2$—), 1.75 ppm (m, 1H, CH—CH$_2$—), 1.89 ppm (m, 1H, CH—CH$_2$—), 2.26 ppm (s, 3H, —NCH$_3$), 2.31 (s, 3H, N—CH$_2$), 2.40 (m, 1H, N—CH$_2$—), 2.52 ppm (m, 4H, methylpiperazine), 2.60 (m, 1H, N—CH$_2$—), 3.32 ppm (m, 4H, methylpiperazine), 3.77 ppm (m, 1H, CO—CH), 6.87 ppm (d, 2H, aromatic), 8.00 ppm (d, 2H, aromatic)

[Esterified Product of Compound (A)]

(Example 8) Synthesis of Compound (M'1; n=6)

41.0 g of the compound (5') [2-dimethylamino-1-(4-morpholinophenyl)-2-(4-carboxybenzyl)butan-1-one] obtained in Example 1, 1 mL of N,N-dimethylformamide

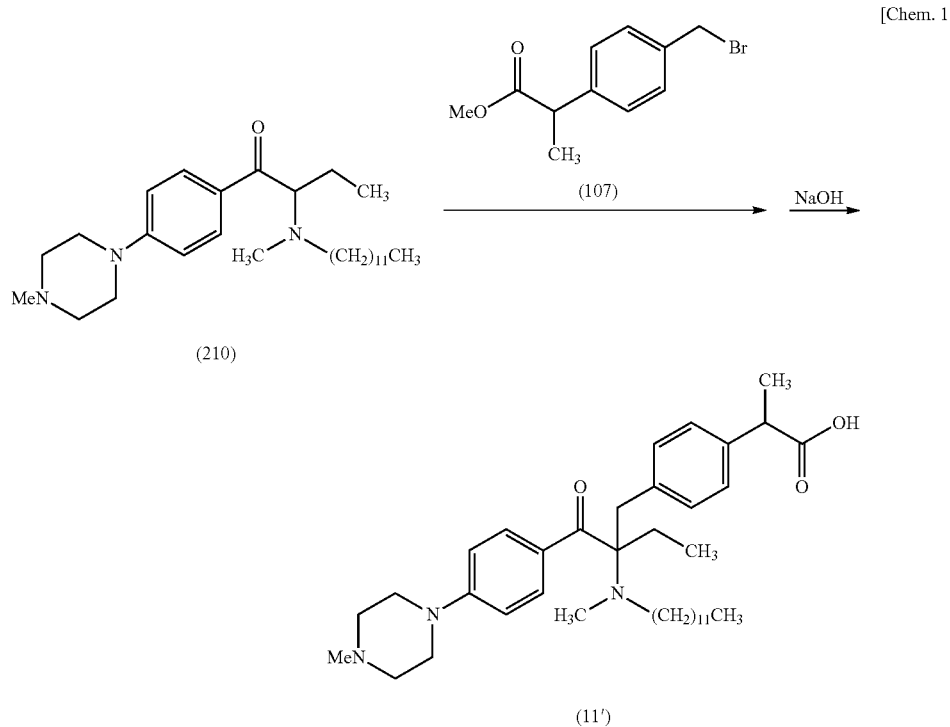

[Chem. 120]

[Step 4]

22.2 g of 2-methyldodecyamino-1-(4-methylpiperazinophenyl)butan-1-one (210) obtained in the above, 13.5 g of methyl 2-(4-bromomethyl)phenylpropionate (107) and 50 mL of IPA were put into a 300-mL flask equipped with a stirrer, a thermometer and a condenser tube, and stirred at 50° C. for 3 hours. Subsequently, 16 mL of an aqueous 8 M sodium hydroxide solution was added, and stirred at 50° C. for 1 hour to complete the reaction. Using an aqueous hydrochloric acid solution, this was made to have a pH of 5.7, and then IPA was evaporated away. The concentrated residue was extracted with ethyl acetate, washed twice with water and once with a saturated saline solution. Ethyl acetate was evaporated away under reduced pressure, and the crude product was purified through column chromatography to give a pale yellow oily compound (11'), (2-methyldodecylamino-1-(4-methylpiperazinophenyl)-2-(4-(1-hydroxy-1-oxopropan-2-yl)benzyl)butan-1-one).

Actual yield: 24.5 g, percent yield: 81%

$^1$H-NMR (CDCl$_3$): 0.62 ppm (t, 3H, —CH$_3$), 0.86 ppm (t, 3H, —CH$_3$), 1.20 ppm (m, 18H, —CH$_2$—) 1.34 ppm (m, 2H, N—CH$_2$—CH$_2$—CH$_2$—), 1.45 ppm (d, 3H, CH—CH$_3$), 1.75 ppm (m, 1H, CH—CH$_2$—), 1.89 ppm (m, 1H, CH—CH$_2$—), 2.26 ppm (s, 3H, —N—CH$_3$), 2.31 (s, 3H, N—CH$_3$), 2.40 (m, 1H, N—CH2-), 2.52 ppm (m, 4H, methylpiperazine), 2.65 (m, 1H, N—CH2-), 3.32 ppm (m, 4H, methylpiperazine), 3.16 (s, 2H, —CH$_2$-Ph), 3.67 (q, 1H, CH—CH$_3$), 6.82 ppm (d, 2H, aromatic), 7.39 ppm (d, 2H, aromatic), 7.95 ppm (d, 2H, aromatic), 8.35 ppm (d, 2H, aromatic)

(DMF) and 100 mL of methylene chloride were put into a 1-L three-neck flask equipped with a stirrer, a condenser and a thermocouple, and dissolved, and 13.1 g of thionyl chloride was dropwise added thereto and reacted for 2 hours. Further, 5.91 g of 1,6-hexanediol was added, and the mixed solution was dropwise added to 30.3 g of trimethylamine and 300 mL of methylene chloride put in a 2-L three-neck flask, and stirred at room temperature for 1 hour. After the reaction, this was extracted with methylene, washed twice with water, the organic layer was dried over anhydrous magnesium sulfate, and the organic solvent was evaporated away under reduced pressure to give a crude product of the compound (M'1; n=6). This was purified through silica gel column chromatography to give 40.1 g of the compound (M'1; n=6). (percent yield 89%)

(Example 9) Synthesis of Compound (M'2; n=4)

38.3 g of the compound (M'2) was synthesized according to the method described in Example 8, except that in synthesis in Example 8, 10.0 g of polyethylene glycol (PEG-200/mean molecular weight 200; Sanyo Chemical Industries, Ltd.) was used in place of 1,6-hexanediol. (percent yield 78%)

(Example 10) Synthesis of Compound (M'4; n=3)

45.8 g of the compound (M'4; n=3) was synthesized according to the method described in Example 8, except that in synthesis in Example 8, 12.5 g of polytetrahydrofuran (mean molecular weight 250) was used in place of 1,6-hexanediol. (percent yield 89%)

(Example 11) Synthesis of Compound (M'7; n=1)

40.8 g of the compound (M'7; n=1) was synthesized according to the method described in Example 8, except that in synthesis in Example 8, 8.87 g of EO-modified trimethylolpropane (TMP-30; Nippon Nyukazai Co., Ltd.) was used in place of 1,6-hexanediol. (percent yield 85%)

(Example 12) Synthesis of Compound (M'9; n=1)

43.9 g of the compound (M'9; n=1) was synthesized according to the method described in Example 8, except that in synthesis in Example 8, 7.81 g of EO-modified pentaerythritol (PNT-40; Nippon Nyukazai Co., Ltd.) was used in place of 1,6-hexanediol. (percent yield 93%)

(Example 13) Synthesis of Compound (M'11)

Figure 5:
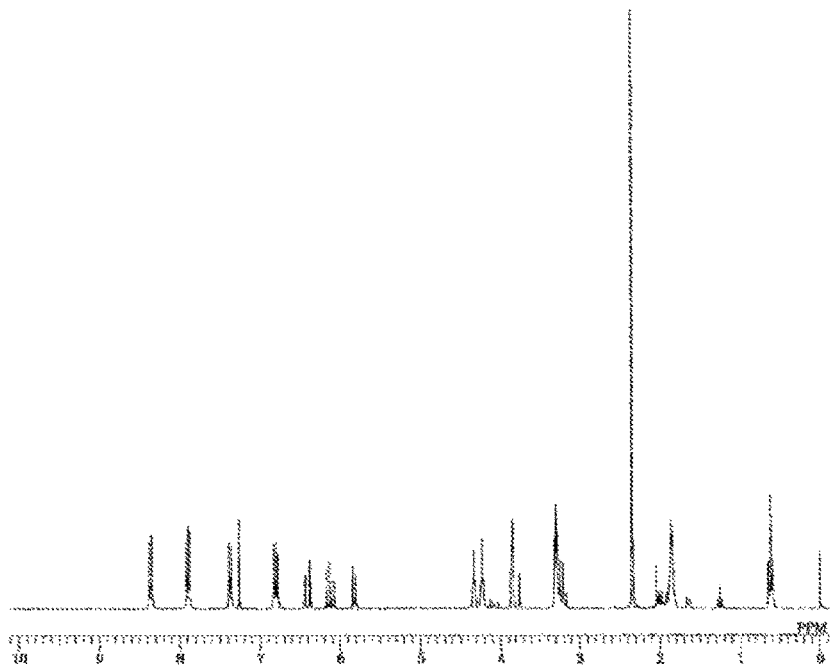
FIG. 5 shows a $^1$H-NMR chart of the compound (M'11) obtained in Example 13.

44.5 g of the compound (M'11) was synthesized according to the method described in Example 8, except that in synthesis in Example 8, 14.4 g of 4-hydroxybutyl acrylate (4-HBA; Osaka Organic Chemical Industry Ltd.) was used in place of 1,6-hexanedlol. (percent yield 83%) The $^1$H-NMR chart of the resultant compound (M'11) is shown in FIG. 5.

(Example 14) Synthesis of Compound (M'12)

51.3 g of the compound (M'12) was synthesized according to the method described in Example 8, except that in synthesis in Example 8, 24.6 g of tripropylene oxide monoacrylate was used in place of 1,6-hexanediol. (percent yield 80%)

(Example 15) Synthesis of Compound (M'13)

69.5 g of the compound (M'13) was synthesized according to the method described in Example 8, except that in synthesis in Example 8, 37.4 g of EO-modified (3) trimethylolpropane diacrylate was used in place of 1,6-hexanediol. (percent yield 91%)

(Example 16) Synthesis of Compound (M'14)

75.4 g of the compound (M'14) was synthesized according to the method described in Example 8, except that in synthesis in Example 8, 53.6 g of EO-modified (5) pentaerythritol triacrylate (MIRAMER M4003: MIWON Specialty Co., Ltd.) was used in place of 1,6-hexanediol. (percent yield 81%)

(Example 17) Synthesis of Compound (M'15; n=6)

34.5 g of the compound (M'15) was synthesized according to the method described in Example 8, except that in synthesis in Example 8, 15.0 g of 1,6-hexanedithiol was used in place of 1,6-hexanediol. (percent yield 74%)

(Example 18) Synthesis of Compound (M'17; n=6)

39.3 g of the compound (M'17; n=6) was synthesized according to the method described in Example 8, except that in synthesis in Example 8, 11.6 g of 1,6-hexanediamine was used in place of 1,6-hexanediol. (percent yield 86%)

(Example 19) Synthesis of Compound (M'19; n=6)

41.0 g of the compound (5') [2-dimethylamino-1-(4-morpholinophenyl)-2-(4-carboxybenzyl)butan-1-one] obtained in Example 1, 11.5 g of 1,6-hexanediol diglycidyl ether (EX-212; Nagase ChemteX Corporation), 2 g of tetraammonium bromide and 500 mL of acetonitrile were put into a 2-L three-neck flask equipped with a stirrer, a condenser and a thermocouple, and reacted with heating under reflux for 10 hours. After the reaction, this was left cooled to room temperature, extracted with methylene chloride, and washed twice with 5% sodium hydrogencarbonate and once with water. The organic layer was dried over anhydrous magnesium sulfate, and the organic solvent was evaporated away under reduced pressure to give a crude product of the compound (M'19; n=6). This was purified through silica gel column chromatography to give 46.2 g of the compound (M'19; n=6). (percent yield 88%)

(Example 20) Synthesis of Compound (M'23)

45.2 g of the compound (M'23) was synthesized according to the method described in Example 19, except that in synthesis in Example 19, 21.3 g of glycidyl methacrylate (GMA) was used in place of 1,6-hexanediol diglycidyl ether. (percent yield 82%)

(Example 21) Synthesis of Compound (M'24)

48.9 g of the compound (M'24) was synthesized according to the method described in Example 19, except that in synthesis in Example 19, 30.0 g of 4-hydroxybutyl acrylate glycidyl ether (4HBAGE; Nippon Kasei Co., Ltd.) was used in place of 1,6-hexanediol diglycidyl ether. (percent yield 81%)

(Synthesis Example 1) Synthesis of Compound (5) [2-dimethylamino-1-(4-piperazinylphenyl)-2-(4-piperazine-1-carbonyl)benzyl)butan-1-one]

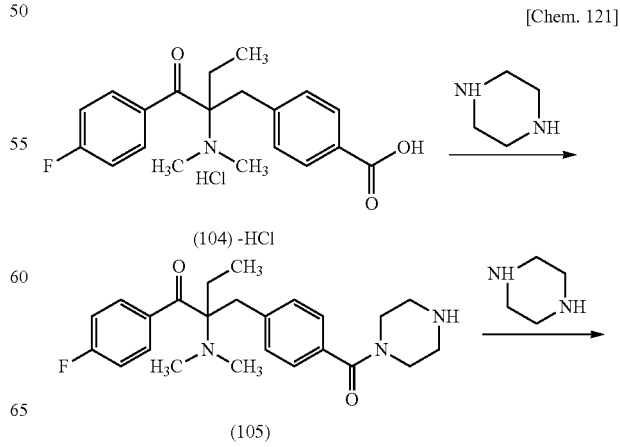

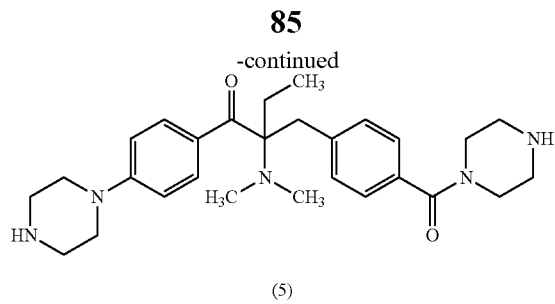

(5)

Figure 6:
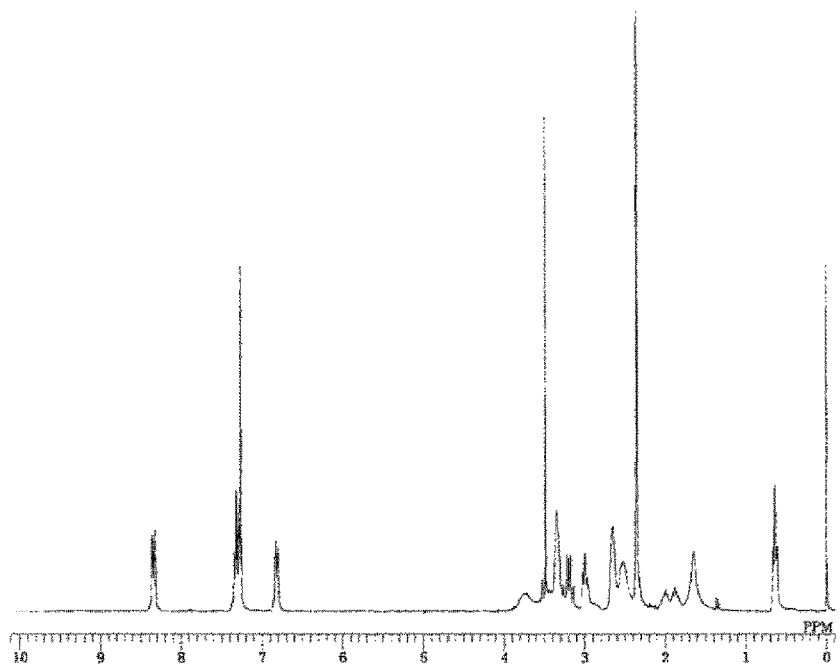
FIG. 6 shows a $^1$H-NMR chart of the compound (5) obtained in Synthesis Example 1.

In the same manner as in the step 1 to the step 3 in Example 1, the intermediate (104) was prepared, and then 19.3 g of 2-chloro-4,6-dimethoxy-1,3,5-triazine and 100 mL of dewatered dichloromethane were put into a 500-mL four-neck flask equipped with a stirrer, a thermometer and a dropping funnel, and cooled with ice using an ice bath. 33.3 g of N-methylmorpholine was dropwise added thereto via the dropping funnel, taking 10 minutes. After the addition, 38.0 g of the intermediate (104) was added, and stirred with cooling with ice for 2 hours. 200 ml of dewatered dichloromethane with 34.4 g of piperazine dissolved therein was dropwise added thereto via the dropping funnel, taking 20 minutes. The ice bath was removed, and this was kept stirred for 2 hours at room temperature. After the stirring, this was put into distilled water, and the lower layer was collected. Further, this was washed four times with distilled water, dried over magnesium sulfate for 24 hours, and then dichloromethane was evaporated away under reduced pressure to give the intermediate (105). Subsequently, 100 mL of DMSO and 34.4 g of piperazine were added, and heated at 120° C. in a nitrogen stream atmosphere for 15 hours. After this, distilled water was added, the precipitated crystal was taken out through filtration, washed twice alternately with distilled water and ethanol, and dried to give 2-dimethylamino-1-(4-piperazinylphenyl)-2-(4-piperazine-1-carbonyl)benzyl)butan-1-one (compound (5)). The $^1$H-NMR chart of the resultant compound (5) is shown in FIG. 6.

Actual yield: 41.7 g, percent yield: 87.4%

$^1$H-NMR (CDCl$_3$): 0.64 ppm (t, 3H, —CH$_3$), 1.83 ppm (m, 1H, —CH$_2$—), 2.00 ppm (m, 1H, —CH$_2$—) 2.03 ppm (m, 2H, Piperazine), 2.36 (s, 6H, N—CH$_3$), 2.45-2.90 ppm (br, 8H, Piperazine), 2.96-3.90 (br, 8H, Piperazine), 3.10 (m, 2H, —CH$_2$-Ph), 6.82 ppm (d, 2H, aromatic), 7.28 ppm (m, 4H, aromatic), 8.34 ppm (d, 2H, aromatic)

(Synthesis Example 2) Synthesis of Compound (6) [2-methyldodecylamino-1-(4-piperazinylphenyl)-2-(4-(piperazine-1-carbonyl)benzyl)butan-1-one]

[Chem. 122]

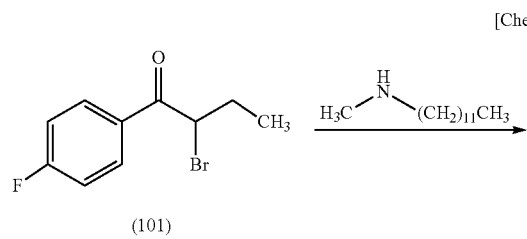

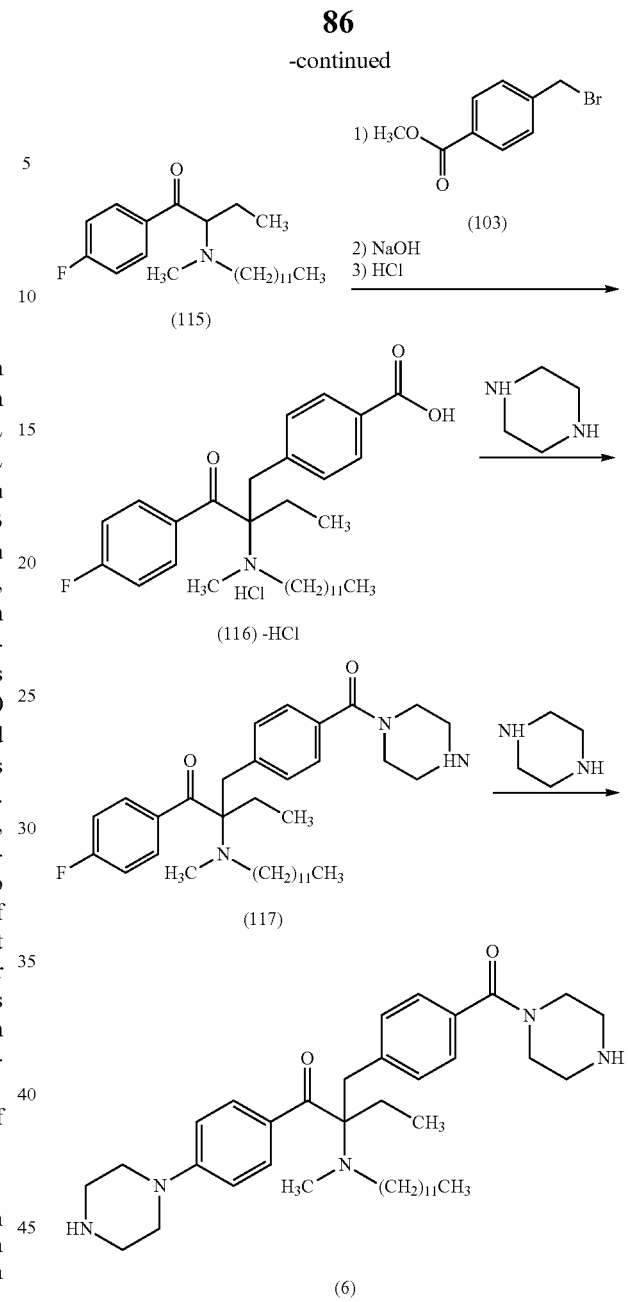

35.5 g of the compound (6) (2-methyldodecylamino-1-(4-piperazinylphenyl)-2-(4-(piperazinyl-1-carbonyl)benzyl)butan-1-one was obtained according to the method described in Synthesis Example 1, except that, in the production method of Synthesis Example 1, 385.0 g of methyldodecylamine was used in place of 157.7 g of 11% dimethylamine/ethanol solution.

$^1$H-NMR (CDCl$_3$): 0.64 ppm (t, 3H, —CH$_3$), 0.84 ppm (t, 3H, —CH$_3$), 1.20 ppm (m, 18H, —CH$_2$—), 1.34 ppm (m, 2H, N—CH$_2$—CH$_2$—CH$_2$—), 1.86 (m, 1H, C—CH$_2$—CH$_3$), 2.03 ppm (m, 2H, Piperazine), 2.13 (m, 1H, C—CH$_3$—CH$_3$), 2.30 (s, 3H, N—CH$_3$), 2.45-2.90 ppm (br, 8H, Piperazine), 2.40 (m, 1H, N—CH$_2$—), 2.60 (m, 1H, N—CH$_2$—), 2.96-3.90 (br, 8H, Piperazine), 3.10 (m, 2H, —CH$_2$-Ph), 6.82 ppm (d, 2H, aromatic), 7.28 ppm (m, 4H, aromatic), 8.34 ppm (d, 2H, aromatic)

(Synthesis Example 3) Synthesis of Compound (7) [2-dimethylamino-1-(4-(methyl(2-(methylamino) ethyl)amino)phenyl)-2-(4-(methyl(2-(methylamino) ethyl)amino)-1-carbonyl)benzyl)butan-1-one]

2-Dimethylamino-1-(4-(methyl(2-(methylamino)ethyl) amino)phenyl)-2-(4-(methyl(2-(methylamino)ethyl)amino)-1-carbonyl)benzyl)butan-1-one was synthesized according to the method described in Synthesis Example 1, except that 35.2 g of N,N'-dimethylethylenediamine was used in place of 34.4 g of piperazine.

$^1$H-NMR (CDCl$_3$): 0.64 ppm (t, 3H, —CH$_3$), 1.83 ppm (m, 1H, —CH$_2$—), 2.00 ppm (m, 1H, —CH$_2$—), 2.57 ppm (m, 4H, N—CH$_2$—), 2.65 ppm (s, 3H, Ar—N—CH$_3$), 2.36 (s, 6H, N—CH$_3$), 3.10 (m, 2H, —CH$_2$-Ph), 3.22 ppm (s, 3H, NH—CH$_3$), 3.26 ppm (s, 3H, NH—CH$_3$), 3.27 (s, 3H, —N—CH$_3$), 3.41 (m, 4H, MeN—CH$_2$—), 6.80 ppm (d, 2H, aromatic), 7.25 ppm (m, 4, aromatic), 8.31 ppm (d, 2H, aromatic)

(Synthesis Example 4) Synthesis of Compound (8) [2-dimethylamino-1-(4-piperazinylphenyl)-2-(4-(1-piperazinyl-1-oxopropan-2-yl)benzyl)butan-1-one]

[Step 1]

[Chem. 123]

20.7 g of the intermediate (102), 25.4 g of methyl 2-(4-bromomethyl)phenylpropionate (107) and 75 mL of IPA were put into a 500-mL four-neck flask equipped with a stirrer, a thermometer and a condenser tube, and stirred at room temperature for 24 hours. Subsequently, 105 mL of an aqueous 10 wt % sodium hydroxide solution was added, and stirred at room temperature for 24 hours. After the stirring, this was extracted with dichloromethane, washed three times with water, dried over magnesium sulfate, and dichloromethane was evaporated away under reduced pressure to give the intermediate (109).

Actual yield: 20.6 g, percent yield: 56.0%

$^1$H-NMR (CDCl$_3$): 0.65 ppm (t, 3H, —CH$_3$), 1.42 (d, 3H, CH—CH$_3$), 1.81 ppm (m, 1H, —CH$_2$—), 2.04 ppm (m, 1H, —CH$_2$—), 2.35 ppm (s, 6H, N—CH$_3$), 3.16 ppm (s, 2H, —CH$_2$-Ph), 3.69 (m, 1H, Ar—CH—), 7.04 ppm (dd, 2H, aromatic), 7.16 ppm (m, 4H, aromatic), 8.39 ppm (dd, 2H, aromatic)

[Step 3]

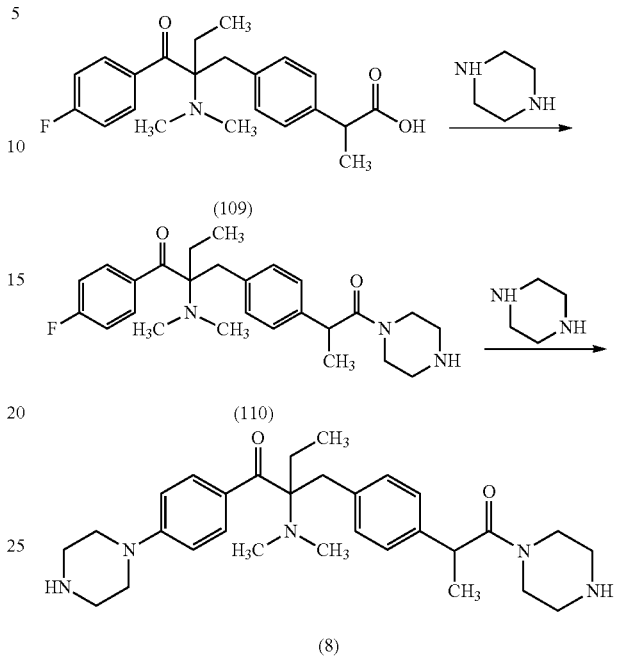

6.1 g of 2-chloro-4,6-dimethoxy-1,3,5-triazine and 50 mL of dewatered dichloromethane were put into a 300-mL four-neck flask equipped with a stirrer, a thermometer and a dropping funnel, and cooled with ice using an ice bath. 10.5 g of N-methylmorpholine was dropwise added thereto, taking 10 minutes. A solution of 11.7 g of the intermediate (109) dissolved in 100 mL of dewatered dichloromethane was dropwise added thereto, taking 30 minutes. After the addition, this was kept stirred as such for 2 hours in an ice bath. 50 mL of dewatered dichloromethane with 10.8 g of piperazine dissolved therein was dropwise added thereto taking 10 minutes. The ice bath was removed, and this was kept stirred at room temperature for 2 hours. After the stirring, this was put into distilled water, and the lower layer was collected. This was further washed four times with distilled water, and then dried over magnesium sulfate for 24 hours. Dichloromethane was evaporated away under reduced pressure to give the intermediate (110). Subsequently, 50 mL of DMSO and 10.8 g of piperazine were added, and heated at 120° C. in a nitrogen stream atmosphere for 15 hours. Subsequently, distilled water was added, and the precipitated crystal was taken out through filtration, washed twice with water, and dried to give the compound (8) (2-dimethylamino-(4-piperazinylphenyl)-2-(4-(1-piperazinyl-1-oxopropan-2-yl)benzyl)butan-1-one).

Actual yield: 11.2 g, percent yield: 70.0%

$^1$H-NMR (CDCl$_3$): 0.64 ppm (t, 3H, —CH$_3$), 1.62 (d, 3H, CH—CH$_3$), 1.83 ppm (m 1H, —CH$_2$—), 2.00 ppm (m, 1H, —CH$_2$—), 2.03 ppm (m, 2H, Piperazine), 2.36 (s, 6H, N—CH$_3$), 2.45-2.90 ppm (br, 8H, Piperazine), 3.01-3.97 (br, 8H, Piperazine), 3.15 (m, 2H, —CH$_2$-Ph), 3.77 (m, 1H, Ar—CH—), 6.82 ppm (d, 2H aromatic), 7.37 ppm (m, 4H, aromatic), 8.34 ppm (d, 2H, aromatic)

(Synthesis Example 5) Synthesis of Compound (14) [2-dimethylamino-1-(4-morpholino)phenyl)-2-(4-(piperazinyl-1-carbonyl)benzyl)butan-1-one]

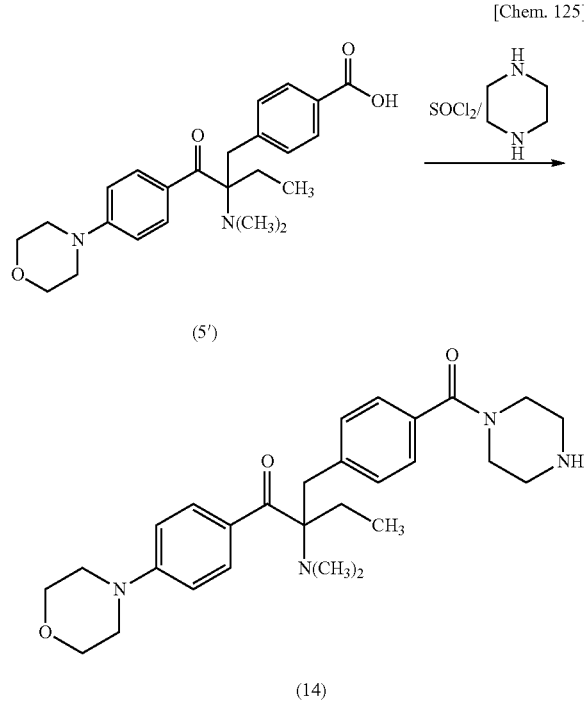

[Step 1]

28.9 g of 2-dimethylamino-1-(4-morpholinophenyl)-2-(4-carboxybenzyl)butan-1-one (5') obtained in Example 2, 1 mL of N,N-dimethylformamide (DMF) and 100 mL of methylene chloride were put into a 300-mL flask equipped with a stirrer, a thermometer and a dropping funnel, and dissolved, and 16.8 g of thionyl chloride was dropwise added thereto and reacted for 2 hours.

Figure 7:
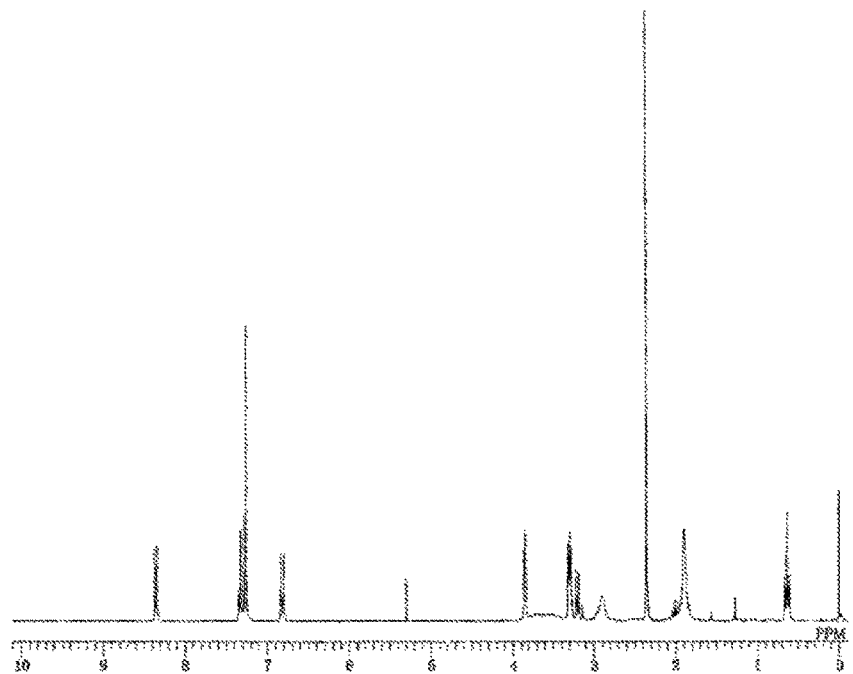
FIG. 7 shows a $^1$H-NMR chart of the compound (14) obtained in Synthesis Example 5.

The reaction solution was concentrated under reduced pressure, the concentrated residue was dissolved in 50 mL of dichloromethane to prepare a dichloromethane solution of the acid chloride. 30.3 g of piperazine and 200 mL of methylene chloride were put into a different 500-mL flask equipped with a stirrer, a thermometer and a dropping funnel, and dissolved, and the previous dichloromethane solution of the acid chloride was dropwise added thereto, taking 30 minutes. This was stirred for 30 minutes to complete the reaction, and an aqueous 1 M-sodium hydroxide solution was added thereto to stop the reaction. The reaction liquid was transferred into a separatory funnel, and the organic layer was washed twice with water, and dried over magnesium sulfate for 24 hours. Dichloromethane was evaporated away under reduced pressure to give the compound (14) (2-dimethylamino-1-(4-morpholino)phenyl)-2-(4-(piperazinyl-1-carbonyl)benzyl)butan-1-one). The $^1$H-NMR chart of the resultant compound (14) is shown in FIG. 7.

Actual yield: 33.0 g, percent yield: 98.0%

$^1$H-NMR (CDCl$_3$): 0.64 ppm (t, 3H, —CH$_3$), 1.83 ppm (m, 1H, —CH$_2$—), 2.00 ppm (m, 1H, —CH2-), 2.36 (s, 6H, N—CH$_3$), 2.80-3.80 ppm (br, 8H, Piperazine), 3.25 ppm (m, 4H, Morpholine), 3.85 ppm (m, 4H, Morpholine), 3.10 (m, 2H, —CH$_2$-Ph), 6.82 ppm (d, 2H, aromatic), 7.28 ppm (m, 4H, aromatic), 8.34 ppm (d, 2H, aromatic)

(Synthesis Example 6) Synthesis of Compound (15) [2-methyldodecyamino-1-(4-(morpholino)phenyl)-2-(4-(piperazinyl-1-carbonyl)benzyl)butan-1-one (15))]

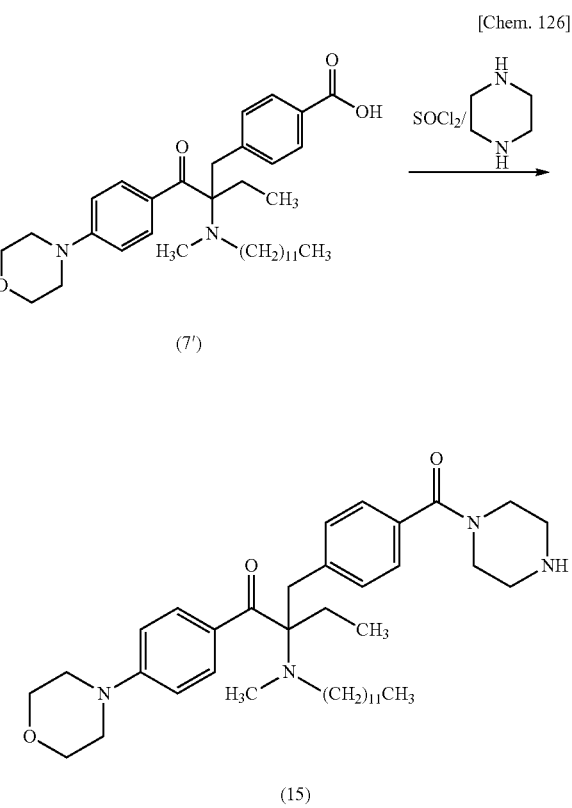

Figure 8:
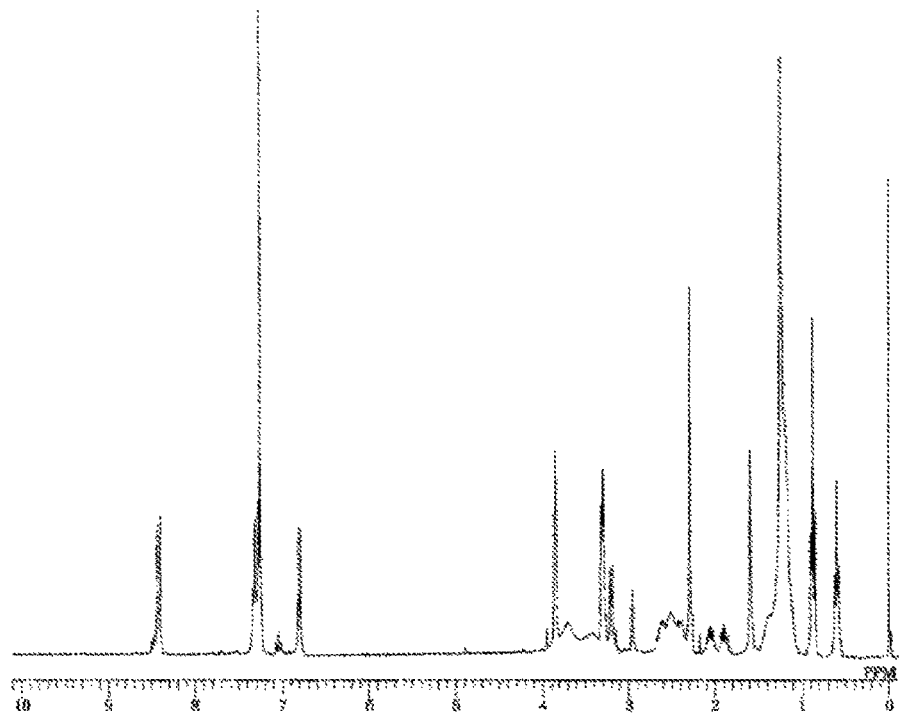
FIG. 8 shows a $^1$H-NMR chart of the compound (16) obtained in Synthesis Example 6.

The compound (15) (2-methyldodecylamino-1-(4-(morpholino)phenyl)-2-(4-(piperazinyl-1-carbonyl)benzyl)butan-1-one) was produced according to the method described in Synthesis Example 5, except that 2-methyldodecylamino-1-(4-morpholinophenyl)-2-(4-carboxybenzyl)butan-1-one (7') obtained in Example 3 was used in place of 2-dimethylamino-1-(4-morpholinophenyl)-2-(4-carboxybenzyl)butan-1-one (5'). The 1H-NMR chart of the resultant compound (15) is shown in FIG. 8.

$^1$H-NMR (CDCl$_3$): 0.64 ppm (t, 3H, —CH$_3$), 0.84 ppm (t, 3H, —CH$_3$), 1.20 ppm (m, 18H, —CH2-), 1.34 ppm (m, 2H, N—CH$_2$—CH$_2$—CH$_2$—), 1.86 (m, 1H, C—CH$_2$—CH$_3$), 2.60-3.81 ppm (br, 8H, Piperazine), 2.13 (m, 1H, C—CH$_2$—CH$_3$), 2.30 (s, 3H, N—CH$_3$), 2.40 (m, 1H, N—CH$_2$—), 2.60 (m, 1H, N—CH$_2$—), 3.10 (m, 2H, —CH$_2$-Ph), 3.29 ppm (m, 4H, Morpholine), 3.85 ppm (m, 4H, Morpholine), 6.82 ppm (d, 2H, aromatic), 7.28 ppm (m, 4H, aromatic), 8.34 ppm (d, 2H, aromatic)

(Synthesis Example 7) Synthesis of 2-methyldodecylamino-1-(4-(4-methylpiperazinyl)phenyl)-2-(4-(1-piperazinyl-1-oxopropan-2-yl)benzyl)butan-1-one (17)

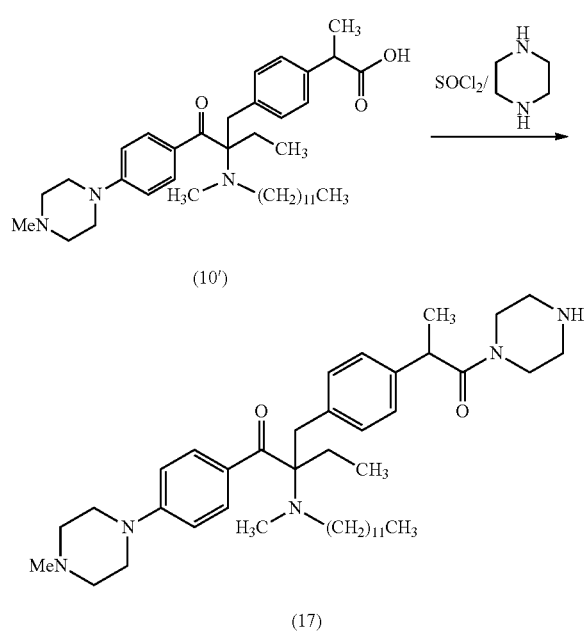

18.2 g of 2-methyldodecylamino-1-(4-methylpiperazinophenyl)-2-(4-1-hydroxy-1-oxopropan-2-yl)benzyl)butan-1-one (10') obtained in Example 4, 0.5 mL of N,N-dimethylformamide (DMF) and 60 mL of methylene chloride were put into a 200-mL flask equipped with a stirrer, a thermometer and a dropping funnel, and dissolved, and 7.15 g of thionyl chloride was dropwise added thereto and reacted for 2 hours. The reaction solution was concentrated under reduced pressure, and the concentrated residue was dissolved in 30 mL of dichloromethane to prepare a dichloromethane solution of the acid chloride. 12.9 g of piperazine and 100 mL of methylene chloride were put into a different 300-mL flask equipped with a stirrer, a thermometer and a dropping funnel, and dissolved, and the previous dichloromethane solution of the acid chloride was dropwise added thereto, taking 20 minutes. This was stirred for 30 minutes to complete the reaction, and an aqueous 1 M-sodium hydroxide solution was added thereto to stop the reaction. The reaction liquid was transferred into a separatory funnel, and the organic layer was washed twice with water, and dried over magnesium sulfate for 24 hours. Dichloromethane was evaporated away under reduced pressure to give 2-methyldodecylamino-1-(4-(4-methylpiperazinyl)phenyl)-2-(4-(1-piperazinyl-1-oxopropan-2-yl)benzyl)butan-1-one (17).

Actual yield: 19.4 g, percent yield: 96.0%

$^1$H-NMR (CDCl3): 0.62 ppm (t, 3H, —CH$_3$), 0.86 ppm (t, 3H, —CH$_3$), 1.20 ppm (m, 18H, —CH$_2$—), 1.34 ppm (m, 2H, N—CH$_2$—CH$_2$—), 1.45 ppm (d, 3H, CH—CH$_3$), 1.75 ppm (m, 1H, CH—CH$_2$—), 1.89 ppm (m, 1H, CH—CH$_2$—), 2.26 ppm (s, 3H, —N—CH$_3$), 2.31 (s, 3H, N—CH$_3$), 2.40 (m, 1H, N—CH$_2$—), 2.52 ppm (m, 4H, methylpiperazine), 2.75-3.660 ppm (br, 8H, piperazine), 3.32 ppm (m, 4H, methylpiperazine), 3.15 (s, 2H, —CH$_2$-Ph), 3.57 (q, 1H, CH—CH3), 6.80 ppm (d, 2H, aromatic), 7.39 ppm (d, 2H, aromatic), 7.95 ppm (d, 2H, aromatic), 8.34 ppm (d, 2H, aromatic)

(Synthesis Example 8) Synthesis of 2-dimethylamino-1-(4-(piperazinyl)phenyl)-2-(4-morpholino-1-(4-carbonyl)benzyl)butan-1-one (23)

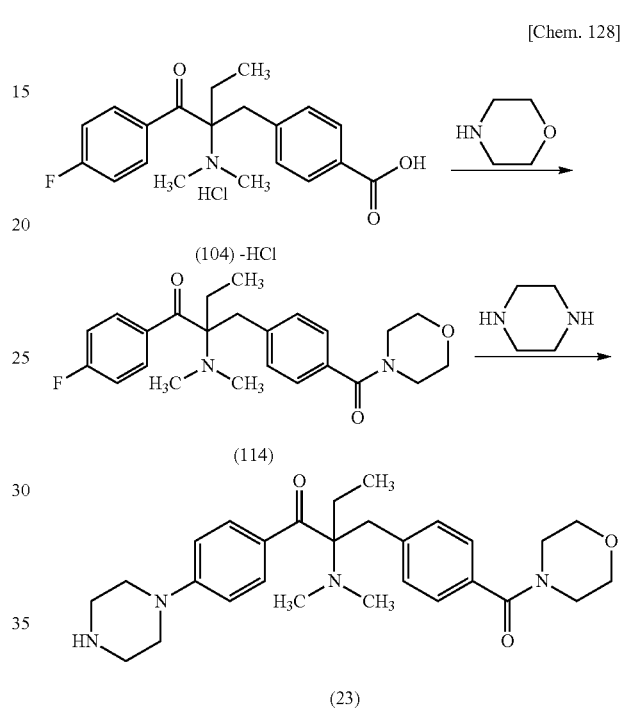

The intermediate (114) was synthesized according to the method described in Production Example 1 except that 34.8 g of morpholine was used in place of 34.4 g of piperazine in Synthesis Example 1.

Actual yield: 39.5 g, percent yield: 95.6%

$^1$H-NMR (CDCl$_3$): 0.63 ppm (t, 3H, —CH$_3$), 1.81 ppm (m, 1H, —CH$_2$—), 2.02 ppm (m, 1H, —CH$_2$—), 2.37 (s, 6H, N—CH$_3$), 3.20 (m, 2H, —CH$_2$-Ph), 3.69 (br, 8H, Morpholine), 7.05 ppm (d, 2H, aromatic), 7.28 ppm (m, 4H, aromatic), 8.41 ppm (d, 2H, aromatic)

Subsequently, 100 ml of DMSO and 34.4 q of piperazine were added, and heated at 120° C. in a nitrogen stream atmosphere for 15 hours. After this, distilled water was added, and the precipitated crystal was taken out through filtration, washed twice alternately with distilled water and ethanol, and dried to give the compound (23) (2-dimethylamino-1-(4-(piperazinyl)phenyl)-2-(4-morpholino-1-carbonyl)benzyl)butan-1-one).

Actual yield: 41.3 g, percent yield: 90.1%

$^1$H-NMR (CDCl$_3$), 0.63 ppm (t, 3H, —CH$_3$), 1.80 ppm (m, 1H, —CH$_2$—), 2.02 ppm (m, 1H, —CH$_2$—), 2.37 (s, 6H, N—CH$_3$), 3.02 ppm (m, 4H, Piperazine), 3.15 (m, 2H, —CH$_2$-Ph), 3.26 ppm (m, 4H, Piperazine), 3.73 (br, 8H, Morpholine), 6.82 ppm (d, 2H, aromatic), 7.28 ppm (m, 4H, aromatic), 8.34 ppm (d, 2H, aromatic)

(Synthesis Example 9) Synthesis of 2-methyldodecylamino-1-(4-(piperazinyl)phenyl)-2-(4-morpholino-1-carbonyl)benzyl)butan-1-one (24)

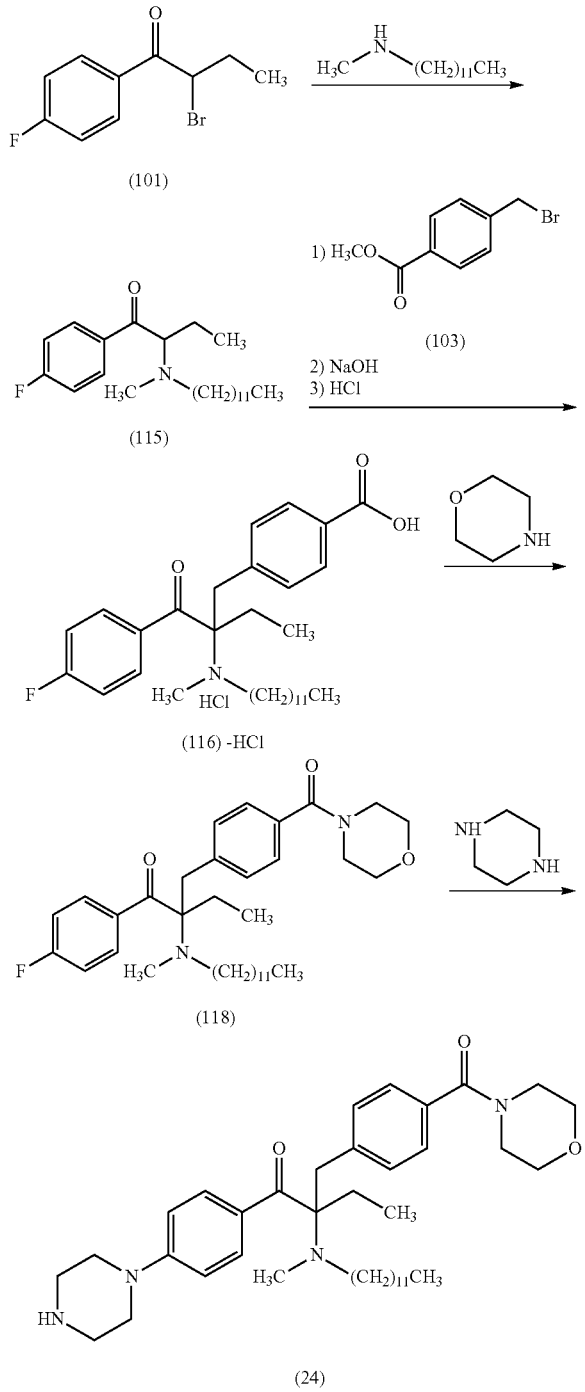

The compound (24) (2-methyldodecylamino-1-(4-(piperazinyl)phenyl)-2-(4-morpholino-1-carbonyl)benzyl)butan-1-one) was synthesized according to the method described in Synthesis Example 2, except that morpholine was used in place of piperazine to be amidated with the intermediate (116) in Synthesis Example 2.

$^1$H-NMR (CDCl$_3$): 0.64 ppm (t, 3H, —CH$_3$), 0.84 ppm (t, 3H, —CH$_3$), 1.20 ppm (m, 1H, C—CH$_2$—CH$_3$), 1.34 ppm (m, 2H, N—CH$_2$—CH$_2$—CH$_2$—), 1.86 (m, 1H, C—CH$_2$—CH$_3$), 2.13 (m, 1H, C—CH$_2$—CH$_3$), 2.30 (s, 3H, N—CH$_3$), 2.40 (m, 1H, N—CH$_2$—) 2.60 (m, 1H, N—CH$_2$—), 3.02 ppm (m, 4H, Piperazine), 3.10 (m, 2H, —CH$_2$-Ph), 3.26 (m, 4H, Piperazine), 3.70 ppm (br, 8H, Morpholine), 6.82 ppm (d, 2H, aromatic), 7.28 ppm (m, 4H, aromatic), 8.34 ppm (d, 2H, aromatic)

[Synthesis of Michael Addition Reaction Product (III)]

Example 22

36.6 g of ethylene oxide-modified pentaerythritol tetraacrylate ("Miramer 4004" manufactured by Miwon Specialty Chemical Co., Ltd.) and 9.2 g of the compound (4) obtained in Synthesis Example (1) were put into a 100-mL three-neck flask equipped with a stirrer, a condenser and a thermocouple, and stirred at room temperature for 24 hours to give 45.8 g of a Michael addition reaction product (above-mentioned compound (M1)) of the present invention. The ratio of the Michael addition donor function-having group to the Michael acceptor function-having group in the charged reactants was 1/3.6.

Example 23

32 g of ditrimethylolpropane tetraacrylate ("KAYARAD T1420" manufactured by Nippon Kayaku Co., Ltd.) and 8 g of the compound (5) obtained in Synthesis Example (1) were put into a 100-mL three-neck flask equipped with a stirrer, a condenser and a thermocouple, and stirred at room temperature for 24 hours to give 40 g of a Michael addition reaction product (above-mentioned compound (M2)) of the present invention. The ratio of the Michael addition donor function-having group to the Michael acceptor function-having group in the charged reactants was 1/4.1.

Example 24

28 g of ethylene oxide-modified trimethylolpropane triacrylate ("Aronix M-350" manufactured by Toagosel Co., Ltd.) and 12 g of the compound (5) obtained in Synthesis Example (1) were put into a 100-mL three-neck flask equipped with a stirrer, a condenser and a thermocouple, stirred at 80° C., and then 1 g of 1,8-diazabicyclo[5.4.0]undecane was gradually added. This was stirred at the temperature for 6 hours to give 40 g of a Michael addition reaction product (above-mentioned compound (M3)) of the present invention. The ratio of the Michael addition donor function-having group to the Michael acceptor function-having group in the charged reactants was 1/2.6.

Example 25

32 g of propylene oxide-modified glycerol triacrylate ("Miramer n320" manufactured by Miwon Specialty Chemical Co., Ltd.) and 8 g of the compound (5) obtained in Synthesis Example 1 were put into a 100-mL three-neck flask equipped with a stirrer, a condenser and a thermocouple, and stirred at room temperature for 24 hours to give 40 g of a Michael addition reaction product (above-mentioned compound (M4)) of the present invention. The ratio of the Michael addition donor function-having group to the Michael acceptor function-having group in the charged reactants was 1/4.5.

Example 26

0.35 g of dipentaerythritol hexaacrylate ("Aronix M-405" manufactured by Toagosei Co., Ltd.) and 5 g of the compound (5) obtained in Synthesis Example 1 were put into a 100-mL three-neck flask equipped with a stirrer, a condenser and a thermocouple, and stirred at room temperature for 24 hours to give 40 g of a Michael addition reaction product (above-mentioned compound (M5)) of the present invention. The ratio of the Michael addition donor function-having group to the Michael acceptor function-having group in the charged reactants was 1/5.8.

Example 27

34 g of ethylene oxide-modified pentaerythritol tetraacrylate ("Miramer 4004" manufactured by Miwon Specialty Chemical Co., Ltd.) and 6 g of the compound (6) obtained in Synthesis Example 2 were put into a 100-mL three-neck flask equipped with a stirrer, a condenser and a thermocouple, and stirred at room temperature for 24 hours to give 40 g of a Michael addition reaction product (above-mentioned compound (M6)) of the present invention. The ratio of the Michael addition donor function-having group to the Michael acceptor function-having group in the charged reactants was 1/5.9.

Example 28

34 g of ethylene oxide-modified pentaerythritol tetraacrylate ("Miramer 4004" manufactured by Miwon Specialty Chemical Co., Ltd.) and 6 g of the compound (7) obtained in Synthesis Example 3 were put into a 100-mL three-neck flask equipped with a stirrer, a condenser and a thermocouple, and stirred at room temperature for 24 hours to give 40 g of a Michael addition reaction product (above-mentioned compound (M7)) of the present invention. The ratio of the Michael addition donor function-having group to the Michael acceptor function-having group in the charged reactants was 1/5.1.

Example 29

34 g of ethylene oxide-modified pentaerythritol tetraacrylate ("Miramer 4004" manufactured by Miwon Specialty Chemical Co., Ltd.) and 6 g of the compound (8) obtained in Synthesis Example 4 were put into a 100-mL three-neck flask equipped with a stirrer, a condenser and a thermocouple, and stirred at room temperature for 24 hours to give 40 g of a Michael addition reaction product (above-mentioned compound (M8)) of the present invention. The ratio of the Michael addition donor function-having group to the Michael acceptor function-having group in the charged reactants was 1/5.4.

Example 30

11.0 g of ethylene oxide-modified pentaerythritol tetraacrylate ("Miramer 4004" manufactured by Miwon Specialty Chemical Co., Ltd.) and 10.0 g of the compound (14) obtained in Synthesis Example 5 were put into a 100-mL three-neck flask equipped with a stirrer, a condenser and a thermocouple, and stirred at room temperature for 24 hours to give 21.0 g of a Michael addition reaction product (above-mentioned compound (M9)) of the present invention. The ratio of the Michael addition donor function-having group to the Michael acceptor function-having group in the charged reactants was 1/4.0.

Example 31

12.2 g of ditrimethylolpropane tetraacrylate ("KAYARAD T1420" manufactured by Nippon Kayaku Co., Ltd.) and 10.0 g of the compound (14) obtained in Synthesis Example 5 were put into a 100-mL three-neck flask equipped with a stirrer, a condenser and a thermocouple, and stirred at room temperature for 24 hours to give 22.2 g of a Michael addition reaction product (above-mentioned compound (110)) of the present invention. The ratio of the Michael addition donor function-having group to the Michael acceptor function-having group in the charged reactants was 1/5.0.

Example 32

14.3 g of ethylene oxide-modified trimethylolpropane triacrylate ("Aronix M-350" manufactured by Toagosel Co., Ltd.) and 12 g of the compound (14) obtained in Synthesis Example (5) were put into a 100-mL three-neck flask equipped with a stirrer, a condenser and a thermocouple, and stirred at room temperature for 24 hours to give 26.3 g of a Michael addition reaction product (above-mentioned compound (M11)) of the present invention. The ratio of the Michael addition donor function-having group to the Michael acceptor function-having group in the charged reactants was 1/4.0.

Example 33

18.1 g of tripropylene glycol diacrylate ("Aronix M-220" manufactured by Toagosei Co., Ltd.) and 12 g of the compound (14) obtained in Synthesis Example (5) were put into a 100-mL three-neck flask equipped with a stirrer, a condenser and a thermocouple, and stirred at room temperature for 24 hours to give 30.1 g of a Michael addition reaction product (above-mentioned compound (M12)) of the present invention. The ratio of the Michael addition donor function-having group to the Michael acceptor function-having group in the charged reactants was 1/4.8.

Example 34

12.5 g of ethylene oxide-modified pentaerythritol tetraacrylate ("Miramer 4004" manufactured by Miwon Specialty Chemical Co., Ltd.) and 15.0 g of the compound (15) obtained in Synthesis Example 6 were put into a 100-mL three-neck flask equipped with a stirrer, a condenser and a thermocouple, and stirred at room temperature for 24 hours to give 27.5 g of a Michael addition reaction product (above-mentioned compound (M13)) of the present invention. The ratio of the Michael addition donor function-having group to the Michael acceptor function-having group in the charged reactants was 1/4.0.

Example 35

15.0 g of ethylene oxide-modified trimethylolpropane triacrylate ("Aronix M-350" manufactured by Toagosei Co., Ltd.) and 16.9 g of the compound (18) obtained in Synthesis Example 7 were put into a 100-mL three-neck flask equipped with a stirrer, a condenser and a thermocouple, and stirred at room temperature for 24 hours to give 31.9 g of a Michael addition reaction product (above-mentioned compound (M14)) of the present invention. The ratio of the Michael addition donor function-having group to the Michael acceptor function-having group in the charged reactants was 1/4.2.

Example 36

11.0 g of ethylene oxide-modified pentaerythritol tetraacrylate ("Miramer 4004" manufactured by Miwon Specialty Chemical Co., Ltd.) and 10.0 g of the compound (23) obtained in Synthesis Example 8 were put into a 100-mL three-neck flask equipped with a stirrer, a condenser and a thermocouple, and stirred at room temperature for 24 hours to give 21.0 g of a Michael addition reaction product (above-mentioned compound (M5)) of the present invention. The ratio of the Michael addition donor function-having group to the Michael acceptor function-having group in the charged reactants was 1/4.0.

Example 37

14.3 g of ethylene oxide-modified trimethylolpropane triacrylate ("Aronix M-350" manufactured by Toagosei Co., Ltd.) and 1.2 g of the compound (24) obtained in Synthesis Example 9 were put into a 100-mL three-neck flask equipped with a stirrer, a condenser and a thermocouple, and stirred at room temperature for 24 hours to give 26.3 g of a Michael addition reaction product (above-mentioned compound (M16)) of the present invention. The ratio of the Michael addition donor function-having group to the Michael acceptor function-having group in the charged reactants was 1/4.0.

Comparative Synthesis Example 1

Synthesis of 2-methyl-2-morpholin-4-yl-1-(4-piperazinylphenyl)propan-1-one (26) (Compound of Synthesis Example 2 in Paragraph 10067) in PTL 3)

[Chem. 130]

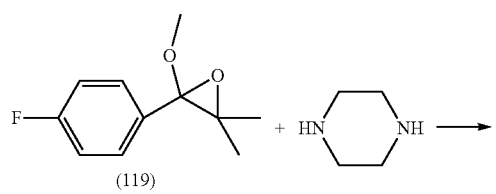

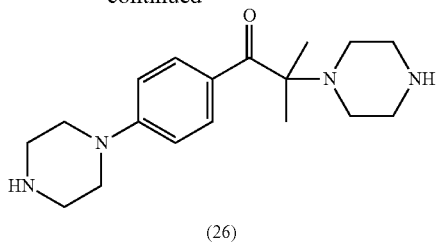

According to the method described in JP-A 60-84248, 2-(4-fluorophenyl)-3,3-dimethyl-2-methoxy-oxirane (119) was synthesized.

Next, 68 g of piperazine was put into a 300-mL four-neck flask equipped with a stirrer, a condenser, a thermocouple, a nitrogen-introducing tube and a dropping tube, and heated at 160° C. in a nitrogen stream atmosphere. 23 g of (43) was dropwise added thereto via a syringe pump at a rate of 4 mL/h, taking 5 hours and 15 minutes, and then further stirred at the temperature for 24 hours. After cooled, the reaction mixture was dissolved in 400 mL of dichloromethane, and washed with 100 mL of water to separate the organic layer. The aqueous layer was washed twice with 100 mL of dichloromethane, and all the resultant organic layers were concentrated to give 36 g of 2-methyl-2-piperazinyl-1-(4-piperazinylphenyl)propan-1-one (26).

$^1$H-NMR (CDCl$_3$): 1.25 ppm (s, 6H, —CH$_3$), 2.59 ppm (m, 4H, —CH$_2$—), 2.92 ppm (m, 4H, —CH$_2$—), 3.28 ppm (m, 4H, —CH$_2$—), 3.91 ppm (s, 2H, NH), 3.98 ppm (m, 4H, —CH$_2$—, 6.86 ppm (m, 2H, aromatic), 8.58 ppm (m, 2H, aromatic)

Comparative Example 1

32 g of ethylene oxide-modified pentaerythritol tetraacrylate ("Miramer 4004" manufactured by Miwon Specialty Chemical Co., Ltd.) and 8 g of 2-methyl-2-piperazinyl-1-(4-piperazinylphenyl)propan-1-one (26) obtained in Comparative Synthesis Example (1) were put into a 100-mL three-neck flask equipped with a stirrer, a condenser and a thermocouple, and stirred at room temperature for 24 hours to give 40 g of a Michael addition reaction product (H1). The ratio of the Michael addition donor function-having group to the Michael acceptor function-having group in the charged reactants was 1/4.8.

[Chem. 131]

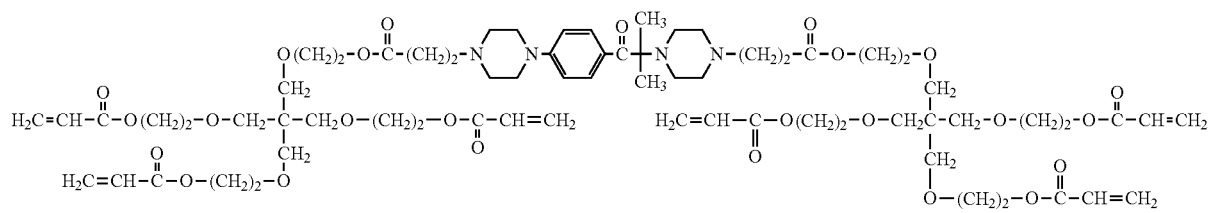

Examples 38 to 81 and Comparative Examples 4 to 7 (Examples and Comparative Examples Relating to Printing Ink)

[Method for Producing Active Energy Ray Curable Printing Ink]

Raw materials were blended according to the composition shown in Table 1, uniformly stirred with a mixer, and then kneaded with a three-roll mill to produce a base ink for printing ink.

Subsequently, according to the composition shown in Table 2 to Table 8, any of various photopolymerization initiators produced in Examples 1 to 37 and Comparative Example 1 and other commercially-available photopolymerization initiators was incorporated in the base ink, uniformly stirred with a mixer and again kneaded with a three-roll mill to produce active energy ray curable printing inks of Examples and Comparative Examples.

[Method for Producing Print Using Active Energy Ray Curable Printing Ink]

Using a simple drawing machine (RI tester, manufactured by Houei Seiko Co., Ltd.), 0.10 ml of the active energy ray curable printing ink produced in the above was uniformly spread on the rubber roll and the metal roll of the RI tester and uniformly drawn on the surface of a milk carton board (polyethylene laminate board) so as to be uniformly spread at a cyan density of 1.6 (measured with a densitometer "Spectro Eye" manufactured by X-Rite Inc.) to produce a print. The RI tester is a testing machine for drawing an ink on paper or film, and can control the ink transfer amount and the printing pressure.

[Method for Curing Active Energy Ray Curable Printing Ink with UV Lamp Light Source]

After printing with the active energy ray curable printing ink, the resultant print was irradiated with ultraviolet (UV) rays to cure and dry the ink coating film. Using a UV irradiation device with, as mounted thereon, a water-cooling metal halide lamp (power 100 W/cm/lamp) and a belt conveyor (attached with a cold mirror, manufactured by Eye Graphics Co., Ltd.), the print was put on the conveyor and led to pass just beneath the lamp (irradiation distance 11 cm) under predetermined conditions mentioned below. The UV irradiation dose under each condition was measured using a UV integral actinometer (Ushio Incorporated's UNIMETER UIT-150-A/light-receiving device UVD-C365).

[Method for Evaluation of Active Energy Ray Curable Printing Ink Composition: UV Curability]

After printed with the ink, the print was processed with the above-mentioned UV irradiation apparatus for four-time UV irradiation at a conveyor speed of 50 m/min to thereby cure the ink layer. Under the condition, the UV integral dose was about 200 mJ/cm$^2$. Immediately after the curing, the cured ink layer was rubbed with a nail (scratch resistance test) to evaluate the UV curability of the ink.

A: No scratch was given even by strong rubbing, and the UV curability is good.

B: A little scratch was given by strong rubbing.

C: Definite scratch was given by strong rubbing.

D: Scratch was given even by weak rubbing, and the UV curability is not good.

[Method for Evaluation of Print with Active Energy Ray Curable Printing Ink: Migration Resistance]

Regarding evaluation of migration resistance, the basic evaluation process is based on the guideline by the European Printing Ink Association, EuPIA (EuPIA Guideline on Printing Inks, applied to the non-food contact surface of food packaging materials and articles, November 2011 (Replaces the September 2009 version)).

Figure 2:
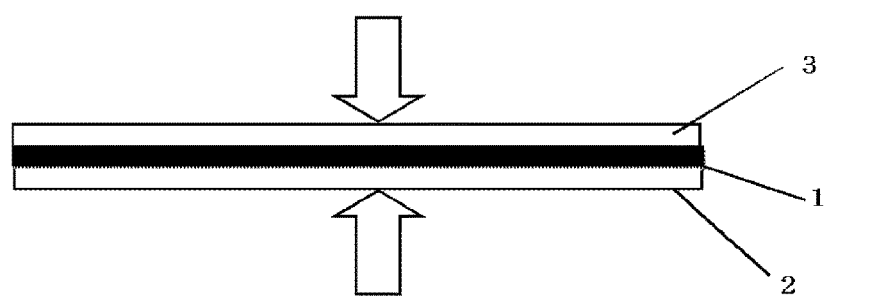
FIG. 2 This is a view showing a mode of overlaying a milk carton white board on the upper surface of the UV-irradiated print in such a manner that the back surface of the milk carton white board could face the upper surface of the print, followed by pressing in the arrowed direction.

First, the ink-coated print was processed with the above-mentioned UV irradiation apparatus for 3-time UV irradiation at a conveyor speed of 50 m/min to cure the ink layer. Under the condition, the UV integral dose was about 150 mJ/cm$^2$. Subsequently, a milk carton white board (hereinafter an unprinted milk carton board with no ink drawn thereon is referred to as a milk carton white board) was layered on the print in such a manner that the back surface of the milk carton board could face the cured ink layer of the print, and pressed using a hydraulic press under a pressing pressure of 40 kg/cm$^2$ in an atmosphere at a temperature of 25° C. for 48 hours, whereby the unreacted components in the cured ink layer were migrated onto the back surface of the milk carton white board (migration) (see FIGS. 1 and 2).

After pressing, the milk carton white board was removed and formed into a 1000-ml liquid container. In this liquid container, the back surface to which the ink components had migrated faced inside. Next, 1000 ml of an aqueous ethanol solution (mixed solution of 95% by weight of ethanol and 5% by weight of pure water) prepared as a pseudo fluid food was put into the liquid container and sealed up. Under the condition, the total area of the inner surface of the liquid container kept in contact with 1000 ml of the aqueous ethanol solution was about 600 cm$^2$. The closed liquid container was statically left as such in an atmosphere at room temperature of 25° C. for 24 hours so that the ink components having migrated to the back surface of the milk carton white board were extracted into the aqueous ethanol solution.

Subsequently, the aqueous ethanol solution was taken out of the liquid container, and using a UV-visible light spectrophotometer (V-570 manufactured by JASCO Corporation), the photopolymerization initiator release concentration (migration concentration) was quantified and the migration resistance was evaluated according to the following three ranks. The photopolymerization initiator has UV absorption performance (absorbance) in a region of 200 to 400 nm, and by previously preparing a calibration curve using the aqueous ethanol solution of all the photopolymerization initiators to be used, the photopolymerization initiator release concentration can be calculated from the absorbance. For realizing good measurement sensitivity, the solution was suitably concentrated and used for the absorbance measurement.

A: The photopolymerization initiator release concentration was less than 5 ppb, and the migration resistance is good.

B: The photopolymerization initiator release concentration was 5 ppb or more and less than 15 ppb.

C: The photopolymerization initiator release concentration was 1.5 ppb or more and less than 30 ppb.

D: The photopolymerization initiator release concentration was 30 ppb or more, and the migration resistance is not good.

TABLE 1

| | Base Ink Composition | | |
|---|---|---|---|
| | Raw Material (product name) | Raw Material (substance name) | Part by mass |
| Binder | Diallyl phthalate resin varnish | Mixture of 35 wt % Delso Dap A dissolved in 65 wt % SR355NS | 29.0 |

TABLE 1-continued

| Base Ink Composition | | | |
|---|---|---|---|
| | Raw Material (product name) | Raw Material (substance name) | Part by mass |
| Monomer | DPHA | Dipentaerythritol hexaacrylate | 40.0 |
| | SR355NS | Ditrimethylolpropane tetraacrylate | 6.8 |
| Pigment | HELIOGEN BLUE D 7079 | Pigment Blue 15:3 | 19.0 |
| Extender | Magnesium carbonate TT | Basic magnesium carbonate | 4.0 |
| Wax | S-381-N1 | Polyolefin wax | 1.0 |
| Polymerization Inhibitor | Stearer TBH | 2-tert-butylhydroquinone | 0.2 |
| Total | | | 100.0 |

In the table, the abbreviations are as follows.

Daiso Dap A: diallyl phthalate resin, manufactured by Osaka Soda Co., Ltd.

SR355NS: ditrimethylolpropane tetraacrylate manufactured by Sartomer

DPHA: dipentaerythritol hexaacrylate, manufactured by Sartomer

HELIOGEN BLUE D7079: Pigment Blue 15:3, manufactured by BASF

Magnesium carbonate TT: basic magnesium carbonate, manufactured by Naikai Salt Industries Co., Ltd.

S-381-N1: polyolefin wax, manufactured by Shamrock

Stearer TBH: 2-tert-butylhydroquinone, manufactured by Seiko Chemical Co., Ltd.

[Method for Evaluation of Print with Active Energy Ray Curable Printing Ink: Odor]

The print cured according to the above-mentioned curing method was cut into a piece having a length of 5 cm and a width of 2.5 cm, and 10 pieces of the type were prepared. These 10 pieces were quickly put into a collection vial having an outer diameter of 40 mm, a height of 75 mm, a mouth inner diameter of 20.1 mm and a volume of 50 ml, and the collection vial was capped and stored in a thermostat bath at 60° C. for one hour, and filled with odor. Next, the collection vial was left to be at room temperature, and 10 panelists for odor evaluation tested the vials and evaluated the intensity of the odor of each sample by 10 ranks.

The odor evaluation results by 10 panelists were averaged to indicate the odor intensity of the sample. Those having a higher numerical value are less odorful.

A: 10 to 9
B: 8 to 6
C: 5 to 3
D: 2 to 1

[Evaluation of Intermediate]

TABLE 2

| | | Example | | | | | Comparative Example | |
|---|---|---|---|---|---|---|---|---|
| | | 38 | 39 | 40 | 41 | 42 | 2 | 3 |
| Offset Base Ink | | 100 | 100 | 100 | 100 | 100 | 100 | 100 |
| Photopolymerization Initiator | Compound (5') | 1.5 | | | | | | |
| | Compound (6') | | 1.6 | | | | | |
| | Compound (7') | | | 2.1 | | | | |
| | Compound (9') | | | | 1.5 | | | |
| | Compound (14') | | | | | 1.5 | | |
| | Irg396 | | | | | | 1.4 | |
| | Irg907 | | | | | | | 1.1 |
| Total | | 101.5 | 101.6 | 102.1 | 101.5 | 101.5 | 101.4 | 101.1 |
| Polymerization Initiator Concentration (mmol/g) | | 0.036 | 0.036 | 0.036 | 0.035 | 0.035 | 0.038 | 0.039 |
| Evaluation Items | Curability | A | A | A | A | A | A | A |
| | Odor | C | C | C | C | C | C | C |

TABLE 3

| Example | | 43 | 45 | 46 | 47 | 48 | 49 | 50 |
|---|---|---|---|---|---|---|---|---|
| Offset Base Ink | | 100 | 100 | 100 | 100 | 100 | 100 | 100 |
| Photopolymerization Initiator | M'1 | 1.8 | | | | | | |
| | M'2 | | 1.8 | | | | | |
| | M'4 | | | 2 | | | | |
| | M'7 | | | | 1.8 | | | |
| | M'9 | | | | | 1.8 | | |
| | M'11 | | | | | | 2 | |
| | M'12 | | | | | | | 2.5 |
| | M'13 | | | | | | | |
| | M'14 | | | | | | | |
| | M'15 | | | | | | | |
| | M'17 | | | | | | | |
| | M'19 | | | | | | | |
| | M'23 | | | | | | | |
| | M'24 | | | | | | | |
| | H1 | | | | | | | |
| | Irg369 | | | | | | | |
| | Irg907 | | | | | | | |
| | Omnipol910 | | | | | | | |
| Total | | 101.8 | 101.8 | 102 | 101.8 | 101.8 | 102 | 102.5 |

TABLE 3-continued

| Example | | 43 | 45 | 46 | 47 | 48 | 49 | 50 |
|---|---|---|---|---|---|---|---|---|
| Polymerization Initiator | Concentration (mmol/g) | 0.039 | 0.036 | 0.038 | 0.037 | 0.038 | 0.037 | 0.038 |
| Evaluation Items | Curability | B | B | B | B | B | B | B |
| | Migration Resistance | B | B | B | B | B | A | A |
| | Odor | C | C | C | C | C | B | B |

TABLE 4

| Example | | 51 | 52 | 53 | 54 | 55 | 56 | 57 |
|---|---|---|---|---|---|---|---|---|
| Offset Base Ink | | 100 | 100 | 100 | 100 | 100 | 100 | 100 |
| Photopolymerization Initiator | M'1 | | | | | | | |
| | M'2 | | | | | | | |
| | M'4 | | | | | | | |
| | M'7 | | | | | | | |
| | M'9 | | | | | | | |
| | M'11 | | | | | | | |
| | M'12 | | | | | | | |
| | M'13 | 3 | | | | | | |
| | M'14 | | 3.6 | | | | | |
| | M'15 | | | 1.8 | | | | |
| | M'17 | | | | 1.8 | | | |
| | M'19 | | | | | 2 | | |
| | M'23 | | | | | | 2.1 | |
| | M'24 | | | | | | | 2.3 |
| | H1 | | | | | | | |
| | Irg369 | | | | | | | |
| | Irg907 | | | | | | | |
| | Omnipol910 | | | | | | | |
| Total | | 103 | 103.6 | 101.8 | 101.8 | 102 | 102.1 | 102.3 |
| Polymerization Initiator | Concentration (mmol/g) | 0.038 | 0.037 | 0.038 | 0.038 | 0.037 | 0.037 | 0.037 |
| Evaluation Items | Curability | B | B | B | B | B | B | B |
| | Migration Resistance | A | A | B | B | B | A | A |
| | Odor | B | B | C | C | C | B | B |

TABLE 5

| Example | | 58 | 59 | 60 | 61 | 62 | 63 | 64 |
|---|---|---|---|---|---|---|---|---|
| Offset Base Ink | | 100 | 100 | 100 | 100 | 100 | 100 | 100 |
| Photopolymerization Initiator | M'1 | 2.5 | | | | | | |
| | M'2 | | | | | | | |
| | M'4 | | | | | | | |
| | M'7 | | | | | | | |
| | M'9 | | | | | | | |
| | M'11 | | 3 | | | | | |
| | M'12 | | | 3.6 | | | | |
| | M'13 | | | | 4.4 | | | |
| | M'14 | | | | | 5.3 | | |
| | M'15 | | | | | | | |
| | M'17 | | | | | | | |
| | M'19 | | | | | | | |
| | M'23 | | | | | | 3.2 | |
| | M'24 | | | | | | | 3.5 |
| | H1 | | | | | | | |
| | Irg369 | | | | | | | |
| | Irg907 | | | | | | | |
| | Omnipol910 | | | | | | | |
| Total | | 102.5 | 103 | 103.6 | 104.4 | 105.3 | 103.2 | 103.5 |
| Polymerization Initiator | Concentration (mmol/g) | 0.054 | 0.054 | 0.054 | 0.055 | 0.055 | 0.056 | 0.056 |
| Evaluation Items | Curability | B | A | A | A | A | A | A |
| | Migration Resistance | C | A | A | A | A | A | A |
| | Odor | C | B | B | B | B | B | B |

TABLE 6

| Comparative Example | | 4 | 5 | 6 | 7 |
|---|---|---|---|---|---|
| Offset Base Ink | | 100 | 100 | 100 | 100 |
| Photopolymerization Initiator | M'1 | | | | |
| | M'2 | | | | |
| | M'4 | | | | |
| | M'7 | | | | |
| | M'9 | | | | |
| | M'11 | | | | |
| | M'12 | | | | |
| | M'13 | | | | |
| | M'14 | | | | |
| | M'15 | | | | |
| | M'17 | | | | |
| | M'19 | | | | |
| | M'23 | | | | |
| | M'24 | | | | |
| | H1 | 6.1 | | | |
| | Irg369 | | 1.4 | | |
| | Irg907 | | | 1.1 | |
| | Omnipol910 | | | | 3.8 |
| Total | | 106.1 | 101.4 | 101.1 | 103.8 |
| Polymerization Initiator Concentration (mmol/g) | | 0.036 | 0.038 | 0.039 | 0.035 |
| Evaluation Items | Curability | D | A | A | D |
| | Migration Resistance | A | D | D | C |
| | Odor | C | C | C | C |

TABLE 7

| Example | | 65 | 66 | 67 | 68 | 69 | 70 | 71 | 72 |
|---|---|---|---|---|---|---|---|---|---|
| Offset Base Ink | | 100 | 100 | 100 | 100 | 100 | 100 | 100 | 100 |
| Photopolymerization Initiator | M1 | 9.2 | | | | | | | |
| | M2 | | 9.2 | | | | | | |
| | M3 | | | 6.2 | | | | | |
| | M4 | | | | 9.2 | | | | |
| | M5 | | | | | 14.7 | | | |
| | M6 | | | | | | 16.2 | | |
| | M7 | | | | | | | 12.4 | |
| | M8 | | | | | | | | 13 |
| | M9 | | | | | | | | |
| | M10 | | | | | | | | |
| | M11 | | | | | | | | |
| | M13 | | | | | | | | |
| | M14 | | | | | | | | |
| | M15 | | | | | | | | |
| | M16 | | | | | | | | |
| | H1 | | | | | | | | |
| | Irg369 | | | | | | | | |
| | Irg907 | | | | | | | | |
| | Omnipol910 | | | | | | | | |
| Total | | 109.2 | 109.2 | 106.2 | 109.2 | 114.7 | 116.2 | 112.4 | 113 |
| Polymerization Initiator Concentration (mmol/g) | | 0.035 | 0.035 | 0.036 | 0.035 | 0.034 | 0.033 | 0.034 | 0.034 |
| Evaluation Items | Curability | B | B | B | B | C | C | B | C |
| | Migration Resistance | A | A | A | A | A | A | A | A |
| | Odor | C | C | C | C | C | C | C | C |

TABLE 8

| Example | | 73 | 74 | 75 | 76 | 77 | 78 | 79 | 80 | 81 |
|---|---|---|---|---|---|---|---|---|---|---|
| Offset Base Ink | | 100 | 100 | 100 | 100 | 100 | 100 | 100 | 100 | 100 |
| Photopolymerization Initiator | M1 | 18.4 | | | | | | | | |
| | M2 | | | | | | | | | |
| | M3 | | 12.4 | | | | | | | |
| | M4 | | | | | | | | | |
| | M5 | | | | | | | | | |
| | M6 | | | | | | | | | |
| | M7 | | | | | | | | | |
| | M8 | | | | | | | | | |
| | M9 | | | 3.9 | | | | | | |
| | M10 | | | | 3.8 | | | | | |
| | M11 | | | | | 3.9 | | | | |
| | M13 | | | | | | 5.4 | | | |
| | M14 | | | | | | | 5.2 | | |
| | M15 | | | | | | | | 3.9 | |
| | M16 | | | | | | | | | 5.3 |
| | H1 | | | | | | | | | |
| | Irg369 | | | | | | | | | |
| | Irg907 | | | | | | | | | |
| | Omnipol910 | | | | | | | | | |
| Total | | 118.4 | 112.4 | 104 | 104 | 104 | 105 | 105 | 104 | 105 |
| Polymerization Initiator Concentration (mmol/g) | | 0.065 | 0.069 | 0.037 | 0.034 | 0.036 | 0.037 | 0.035 | 0.037 | 0.037 |
| Evalution Items | Curability | A | A | A | A | A | C | C | A | C |

TABLE 8-continued

| Example | 73 | 74 | 75 | 76 | 77 | 78 | 79 | 80 | 81 |
|---|---|---|---|---|---|---|---|---|---|
| Migration Resistance | A | A | A | A | A | A | A | A | A |
| Odor | C | C | C | C | C | A | A | C | A |

In the tables, the blank means no component incorporated, and the abbreviations are as follows.

Irgacure 369: 2-benzyl-2dimethylamino-1-(4-morpholinophenyl)-butanone-1, manufactured by BASF Irgacure 907: 2-methyl-1-[4-(methylthio)phenyl]-2-morpholinopropan-1-one, manufactured by BASF Omnipol 910: polyethylene glycol di($\beta$-4[4-(2-dimethylamino-2-benzyl)butanoylphenyl]piperazine)propionate, mean molecular weight 910, manufactured by Insight High Technology Examples 82 to 121 and Comparative Examples 10 to 13 (Examples and Comparative Examples of Inkjet Recording Ink)

Raw materials were blended according to the composition shown in Table 9, uniformly stirred with a mixer, and then processed with a bead mill for 4 hours to prepare a mill base.

Next, according to the composition shown in Table 10, the resultant mill base and the other raw materials were blended, and uniformly stirred with a mixer to produce an inkjet base ink.

Finally, according to the composition shown in Table 11 to Table 17, any of various photopolymerization initiators produced in Examples 1 to 37 and Comparative Example 1 and other commercially-available photopolymerization initiators was incorporated in the inkjet base ink, and uniformly stirred with a mixer to produce active energy ray curable inkjet recording inks of Examples and Comparative Examples.

[Method for Producing Print Using Inkjet Recording Ink]

Using an inkjet printer (Konica Minolta's inkjet tester EB100) and using a printer head for evaluation KM512L (discharge amount: 42 pl), a milk carton board (polyethylene laminate board) was printed with the active energy ray curable inkjet recording ink produced in the above to form on the surface of the milk carton board a solid test pattern having a cyan density of 1.6 (measured with a densitometer X-Rite's Spectro Eye), thereby providing a print.

[Method for Curing Inkjet Recording Ink with UV Lamp Light Source]

After printing with the inkjet recording ink, the resultant print was irradiated with ultraviolet (UV) rays to cure and dry the ink coating film. Using a UV irradiation device with, as mounted thereon, a water-cooling metal halide lamp (power: 100 W/cm/lamp) and a belt conveyor (attached with a cold mirror, manufactured by Eye Graphics Co., Ltd.), the print was put on the conveyor and led to pass just beneath the lamp (irradiation distance 11 cm) under predetermined conditions mentioned below. The UV irradiation dose under each condition was measured using a UV integral actinometer (Ushio Incorporated's UNIMETER UIT-150-A/light-receiving device UVD-C365).

[Method for Evaluation of Ink Jet Recording Ink Composition: UV Curability]

After printed with the ink, the print was processed with the above-mentioned UV irradiation apparatus for eight-time UV irradiation at a conveyor speed of 50 m/min to thereby cure the ink layer. Under the condition, the UV integral dose was about 400 mJ/cm$^2$. Immediately after the curing, the cured ink layer was rubbed with a nail (scratch resistance test) to evaluate the UV curability of the ink.

A: No scratch was given even by strong rubbing, and the UV curability is good.

B: A little scratch was given by strong rubbing.

C: Definite scratch was given by strong rubbing.

D: Scratch was given even by weak rubbing, and the UV curability is not good.

[Method for Evaluation of Print with Inkjet Recording Ink: Migration Resistance]

Regarding evaluation of migration resistance, the basic evaluation process is based on the guideline by the European Printing Ink Association, EuPIA (EuPIA Guideline on Printing Inks, applied to the non-food contact surface of food packaging materials and articles, November 2011 (Replaces the September 2009 version)).

First, the ink-coated print was processed with the above-mentioned UV irradiation apparatus for 7-time UV irradiation at a conveyor speed of 50 m/min to cure the ink layer. Under the condition, the UV integral dose was about 350 mJ/cm$^2$. Subsequently, a milk carton white board (hereinafter an unprinted milk carton board with no ink drawn thereon is referred to as a milk carton white board) was layered on the print in such a manner that the back surface of the milk carton board could face the cured ink layer of the print, and pressed using a hydraulic press under a pressing pressure of 40 kg/cm$^2$ in an atmosphere at a temperature of 25° C. for 48 hours, whereby the unreacted components in the cured ink layer were migrated onto the back surface of the milk carton white board (migration) (see FIGS. 1 and 2). After pressing, the milk carton white board was removed and formed into a 1000-ml liquid container. In this liquid container, the back surface to which the ink components had migrated faced inside. Next, 1000 ml of an aqueous ethanol solution (mixed solution of 95% by weight of ethanol and 5% by weight of pure water) prepared as a pseudo fluid food was put into the liquid container and sealed up. Under the condition, the total area of the inner surface of the liquid container kept in contact with 1000 ml of the aqueous ethanol solution was about 600 cm$^2$. The closed liquid container was statically left as such in an atmosphere at room temperature of 25° C. for 24 hours so that the ink components having migrated to the back surface of the milk carton white board were extracted into the aqueous ethanol solution.

Subsequently, the aqueous ethanol solution was taken out of the liquid container, and using a UV-visible light spectrophotometer (V-570 manufactured by JASCO Corporation), the photopolymerization initiator release concentration (migration concentration) was quantified and the migration resistance was evaluated according to the following three ranks. The photopolymerization initiator has UV absorption performance (absorbance) in a region of 200 to 400 nm, and by previously preparing a calibration curve using the aqueous ethanol solution of all the photopolymerization initiators to be used, the photopolymerization initiator release concentration can be calculated from the absorbance. For realizing good measurement sensitivity, the solution was suitably concentrated and used for the absorbance measurement.

A: The photopolymerization initiator release concentration was less than 5 ppb, and the migration resistance is good.

B: The photopolymerization initiator release concentration was 5 ppb or more and less than 15 ppb.

C: The photopolymerization initiator release concentration was 15 ppb or more and less than 30 ppb.

D: The photopolymerization initiator release concentration was 30 ppb or more, and the migration resistance is not good.

TABLE 9

Mill Base Composition

|  | Raw Material (product name) | Raw Material (substance name) | Part by mass |
|---|---|---|---|
| Pigment | FASTGEN BLUE TGR-G | Pigment Blue 15:3 | 25.0 |
| Dispersant | Solsperse 32000 | Basic dispersant | 12.0 |
|  | Miramer M-222 | Dipropylene glycol diacrylate | 63.0 |
|  |  | Total | 100.0 |

In the table, the abbreviations are as follows.

FASTGEN BLUE TGR-G: Pigment Blue 15:3, manufactured by DIC Corporation

Solsperse 32000: basic dispersant, manufactured by Lubrizol Corporation

Miramer M-222: dipropylene glycol diacrylate, manufactured by MIWON Specialty Chemical Co., Ltd.

TABLE 10

|  |  | Raw Material (substance name) | Part by mass |
|---|---|---|---|
| Mill base (part by mass) |  |  | 12.0 |
| Monomer | VEEA-AI | Vinyloxyethoxyethyl acrylate | 38.8 |
|  | Miramer M-222 | Dipropylene glycol diacrylate | 16.5 |
|  | SR341 | 3-methyl-1,5-pentanediol diacrylate | 32.3 |
| Polymerization inhibitor | NONFLEX Alba | 2,5-di-tert-butylhydroquinone | 0.1 |
| Surface tension regulator | KF-351A | Polyether-modified polydimethylsiloxane | 0.3 |
|  |  | Total | 100.0 |

In the table, the abbreviations are as follows.

Miramer M-222: dipropylene glycol diacrylate, manufactured by MIWON Specialty Chemical. Co., Ltd.

VEEA-AI: 2-vinyloxyethoxyethyl acrylate, manufactured by Nippon Shokubai Co., Ltd.

SR341: 3-methyl-1,5-pentanediol diacrylate, manufactured by Sartomer

NONFLEX Alba: 2,5-di-tert-butylhydroquinone, manufactured by NSK Ltd.

KF-351A: polyether-modified polydimethylsiloxane, manufactured by Shin-etsu Chemical Co., Ltd.

TABLE 11

|  |  | Example |  |  |  |  | Comparative Example |  |
|---|---|---|---|---|---|---|---|---|
|  |  | 82 | 83 | 84 | 85 | 86 | 8 | 9 |
| Offset ink base |  | 100 | 100 | 100 | 100 | 100 | 100 | 100 |
| Photopolymerization initiator | Compound (5') | 3 |  |  |  |  |  |  |
|  | Compound (6') |  | 3.2 |  |  |  |  |  |
|  | Compound (8') |  |  | 4.2 |  |  |  |  |
|  | Compound (10') |  |  |  | 3.1 |  |  |  |
|  | Compound (15') |  |  |  |  | 3.1 |  |  |
|  | Irg369 |  |  |  |  |  | 3 |  |
|  | Irg907 |  |  |  |  |  |  | 2.5 |
| Total |  | 103 | 103.2 | 104.2 | 103.1 | 103.1 | 103 | 102.5 |
| Polymerization initiator concentration (mmol/g) |  | 0.071 | 0.071 | 0.071 | 0.071 | 0.071 | 0.079 | 0.087 |
| Evaluation items | Curability | A | A | A | A | A | A | A |
|  | Odor | C | C | C | C | C | C | C |

TABLE 12

|  | Example | 87 | 88 | 89 | 90 | 91 | 92 | 93 |
|---|---|---|---|---|---|---|---|---|
| Inkjet base ink |  | 100 | 100 | 100 | 100 | 100 | 100 | 100 |
| Photopolymerization initiator | M'1 | 3.3 |  |  |  |  |  |  |
|  | M'2 |  | 3.6 |  |  |  |  |  |
|  | M'4 |  |  | 3.8 |  |  |  |  |
|  | M'7 |  |  |  | 3.5 |  |  |  |
|  | M'9 |  |  |  |  | 3.4 |  |  |
|  | M'11 |  |  |  |  |  | 3.9 |  |
|  | M'12 |  |  |  |  |  |  | 4.6 |
|  | M'13 |  |  |  |  |  |  |  |
|  | M'14 |  |  |  |  |  |  |  |
|  | M'15 |  |  |  |  |  |  |  |
|  | M'17 |  |  |  |  |  |  |  |
|  | M'19 |  |  |  |  |  |  |  |
|  | M'23 |  |  |  |  |  |  |  |
|  | M'24 |  |  |  |  |  |  |  |
|  | H1 |  |  |  |  |  |  |  |

TABLE 12-continued

| Example | | 87 | 88 | 89 | 90 | 91 | 92 | 93 |
|---|---|---|---|---|---|---|---|---|
| | Irg369 | | | | | | | |
| | Irg907 | | | | | | | |
| | Omnipol910 | | | | | | | |
| Total | | 103.3 | 103.6 | 103.8 | 103.5 | 103.4 | 103.9 | 104.6 |
| Polymerization initiator concentration (mmol/g) | | 0.071 | 0.071 | 0.071 | 0.07 | 0.07 | 0.07 | 0.069 |
| Evaluation items | Curability | C | C | C | C | C | B | B |
| | Migration resistance | B | B | B | B | B | A | A |
| | Odor | C | C | C | C | C | B | B |

TABLE 13

| Example | | 94 | 95 | 96 | 97 | 98 | 99 | 100 |
|---|---|---|---|---|---|---|---|---|
| Inkjet base ink | | 100 | 100 | 100 | 100 | 100 | 100 | 100 |
| Photopolymerization initiator | M'1 | | | | | | | |
| | M'2 | | | | | | | |
| | M'4 | | | | | | | |
| | M'7 | | | | | | | |
| | M'9 | | | | | | | |
| | M'11 | | | | | | | |
| | M'12 | | | | | | | |
| | M'13 | 5.7 | | | | | | |
| | M'14 | | 7 | | | | | |
| | M'15 | | | 3.4 | | | | |
| | M'17 | | | | 3.3 | | | |
| | M'19 | | | | | 3.8 | | |
| | M'23 | | | | | | 4.1 | |
| | M'24 | | | | | | | 4.5 |
| | H1 | | | | | | | |
| | Irg369 | | | | | | | |
| | Irg907 | | | | | | | |
| | Omnipol910 | | | | | | | |
| Total | | 105.7 | 107 | 103.4 | 103.3 | 103.8 | 104.1 | 104.5 |
| Polymerization initiator concentration (mmol/g) | | 0.07 | 0.07 | 0.07 | 0.07 | 0.07 | 0.071 | 0.071 |
| Evaluation items | Curability | B | B | C | C | C | A | A |
| | Migration resistance | A | A | B | B | B | A | A |
| | Odor | B | B | C | C | C | B | B |

TABLE 14

| Example | | 101 | 102 | 103 | 104 | 105 | 106 | 107 |
|---|---|---|---|---|---|---|---|---|
| Inkjet base ink | | 100 | 100 | 100 | 100 | 100 | 100 | 100 |
| Photopolymerization initiator | M'1 | 5 | | | | | | |
| | M'2 | | | | | | | |
| | M'4 | | | | | | | |
| | M'7 | | | | | | | |
| | M'9 | | | | | | | |
| | M'11 | | 5.8 | | | | | |
| | M'12 | | | 7 | | | | |
| | M'13 | | | | 8.5 | | | |
| | M'14 | | | | | 10.2 | | |
| | M'15 | | | | | | | |
| | M'17 | | | | | | | |
| | M'19 | | | | | | | |
| | M'23 | | | | | | 6.1 | |
| | M'24 | | | | | | | 6.6 |
| | H1 | | | | | | | |
| | Irg369 | | | | | | | |
| | Irg907 | | | | | | | |
| | Omnipol910 | | | | | | | |
| Total | | 105 | 105.8 | 107 | 108.5 | 110.2 | 106.1 | 106.6 |
| Polymerization initiator concentration (mmol/g) | | 101.5 | 0.102 | 0.102 | 0.102 | 0.103 | 0.104 | 0.102 |
| Evaluation items | Curability | B | A | A | A | A | A | A |
| | Migration resistance | C | A | A | A | A | A | A |
| | Odor | C | B | B | B | B | B | B |

TABLE 15

| Comparative Example | | 10 | 11 | 12 | 13 |
|---|---|---|---|---|---|
| Inkjet base ink | | 100 | 100 | 100 | 100 |
| Photopolymerization initiator | M'1 | | | | |
| | M'2 | | | | |
| | M'4 | | | | |
| | M'7 | | | | |
| | M'9 | | | | |
| | M'11 | | | | |
| | M'12 | | | | |
| | M'13 | | | | |
| | M'14 | | | | |
| | M'15 | | | | |
| | M'17 | | | | |
| | M'19 | | | | |
| | M'23 | | | | |
| | M'24 | | | | |
| | H1 | 12.5 | | | |
| | Irg369 | | 3 | | |
| | Irg907 | | | 2.5 | |
| | Omnipol910 | | | | 7.8 |
| Total | | 112.5 | 103 | 102.5 | 107.8 |
| Polymerization initiator concentration (mmol/g) | | 0.07 | 0.079 | 0.087 | 0.07 |
| Evaluation items | Curability | D | A | A | D |
| | Migration resistance | A | D | D | C |
| | Odor | C | C | C | C |

TABLE 16

| Example | | 108 | 109 | 110 | 111 | 112 | 113 | 114 |
|---|---|---|---|---|---|---|---|---|
| Inkjet base ink | | 100 | 100 | 100 | 100 | 100 | 100 | 100 |
| Photopolymerization initiator | M1 | 17.2 | | | | | | |
| | M2 | | 16.4 | | | | | |
| | M3 | | | 10.8 | | | | 21.6 |
| | M4 | | | | 16.5 | | | |
| | M7 | | | | | 24.1 | | |
| | M8 | | | | | | 24.9 | |
| | M9 | | | | | | | |
| | M11 | | | | | | | |
| | M12 | | | | | | | |
| | M13 | | | | | | | |
| | M15 | | | | | | | |
| | M16 | | | | | | | |
| | H1 | | | | | | | |
| | Irg369 | | | | | | | |
| | Irg907 | | | | | | | |
| | Omnipol910 | | | | | | | |
| Total | | 117.2 | 116.4 | 110.8 | 116.5 | 124.1 | 124.9 | 121.6 |
| Polymerization initiator concentration (mmol/g) | | 0.061 | 0.059 | 0.061 | 0.059 | 0.06 | 0.059 | 0.112 |
| Evaluation items | Curability | C | C | B | B | C | C | A |
| | Migration resistance | A | A | A | A | A | A | A |
| | Odor | C | C | C | C | C | C | C |

TABLE 17

| Example | | 115 | 116 | 117 | 118 | 119 | 120 | 121 |
|---|---|---|---|---|---|---|---|---|
| Inkjet base ink | | 100 | 100 | 100 | 100 | 100 | 100 | 100 |
| Photopolymerization initiator | M1 | | | | | | | |
| | M2 | | | | | | | |
| | M3 | | | | | | | |
| | M4 | 34.5 | | | | | | |
| | M7 | | | | | | | |
| | M8 | | | | | | | |
| | M9 | | 6.7 | | | | | |
| | M11 | | | 6.9 | | | | |
| | M12 | | | | 10 | | | |
| | M13 | | | | | 9.1 | | |
| | M15 | | | | | | 6.3 | |
| | M16 | | | | | | | 9.1 |
| | H1 | | | | | | | |
| | Irg369 | | | | | | | |
| | Irg907 | | | | | | | |
| | Omnipol910 | | | | | | | |
| Total | | 134.5 | 106.7 | 106.9 | 110 | 109.1 | 106.3 | 109.1 |
| Polymerization initiator concentration (mmol/g) | | 0.107 | 0.059 | 0.061 | 0.085 | 0.06 | 0.059 | 0.06 |
| Evaluation items | Curability | A | B | B | A | C | B | C |
| | Migration resistance | A | A | A | A | A | A | A |
| | Odor | C | C | C | C | A | C | A |

In the tables, the blank means no component incorporated, and the abbreviations are as follows.

Irgacure 369: 2-benzyl-2-dimethylamino-1-(4-morpholinophenyl)-butanone-1, manufactured by BASF Irgacure 907: 2-methyl-1-[4-(methylthio)phenyl]-2-morpholinopropan-1-one, manufactured by BASF Omnipol 910: polyethylene glycol di(β-4[4-(2-dimethylamino-2-benzyl)butanoylphenyl]piperazine)propionate, mean molecular weight 910, manufactured by Insight High Technology As a result, both the active energy ray curable printing ink and the inkjet recording ink using the active energy ray curable composition of the present invention attained good curability through UV irradiation so that the migration into inclusions was 5 ppb, and realized good results.

On the other hand, regarding the active energy ray curable composition using the Michael addition reaction product described in PTL 3 obtained in Comparative Example 1, as a photopolymerization initiator, both the active ray energy curable printing ink and the inkjet recording ink using the composition were good in migration resistance, but were somewhat poor in curability. The active ray energy curable printing ink and the inkjet recording ink using "Irgacure 379", "Irgacure 907" or "Omnipol 910" were poor in migration resistance.

REFERENCE SIGNS LIST

1 Cured Ink Layer
2 Milk Carton Board
3 Milk Carton White Board

The invention claimed is:

1. A compound to be obtained through Michael addition reaction of an α-aminoacetophenone skeleton-containing compound (I) having a function as a Michael addition donor represented by the following general formula (1), and a reactive compound (II) having a function as a Michael acceptor:

General Formula (1)

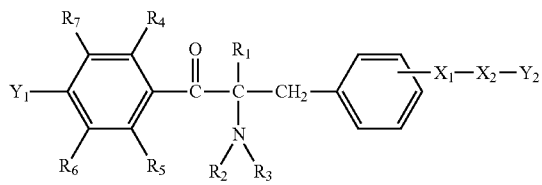

wherein $R_1$ represents an aliphatic group or an aryl group,
$R_2$ to $R_3$ each independently represent an aliphatic group or an aryl group,
$R_2$ and $R_3$ may together form a ring,
$R_4$ to $R_7$ each independently represent a hydrogen atom, an aliphatic group or aryl group,
$X_1$ represents a single bond or a linear or branched alkylene group having 1 to 6 carbon atoms,
$X_2$ represents a carbonyl group or a thiocarbonyl group,
$Y_1$ represents a group represented by the following general formula (2), general formula (3) or general formula (4), and $Y_2$ represents a group represented by the following general formula (2) or general formula (3), provided that when $Y_1$ and $Y_2$ both have a structure represented by the general formula (2), $X_5$ in at least one of them is —NH—;

General Formula (2)

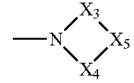

wherein $X_3$ and $X_4$ each independently represent a linear or branched alkylene or oxyalkylene group having 2 to 6 carbon atoms, and $X_5$ represents a single bond, —O— or —NH—;

General Formula (3)

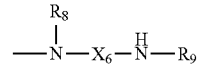

wherein $X_6$ represents a substituted or unsubstituted, linear or branched alkylene or oxyalkylene group having 2 to 6 carbon atoms, and $R_8$ and $R_9$ each independently represent an aliphatic group or an aryl group; and General Formula (4)

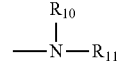

wherein $R_{10}$ and $R_{11}$ each independently represent an aliphatic group or an aryl group.

2. The compound according to claim 1, wherein the reactive compound (II) having a function as a Michael acceptor is a polyfunctional (meth)acrylate compound.

3. The compound according to claim 1, wherein (the number of the Michael addition donor function-having groups in the α-aminoacetophenone skeleton-containing compound (I) having a function as a Michael addition donor)/(the number of the Michael acceptor function-having groups in the reactive compound) is within a range of 1/20 to 1/2.

4. The compound according to claim 1, wherein the α-aminoacetophenone skeleton-containing compound (I) having a function as a Michael addition donor represented by the general formula (1) is a compound represented by any of the following structural formulae (5) to (26):

(5)

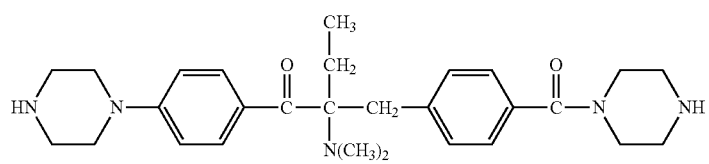

(6)
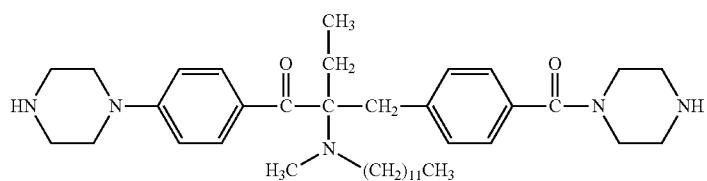
(7)
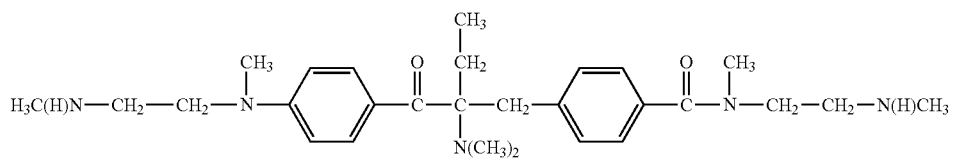
(8)
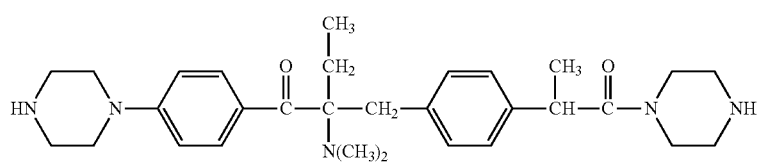
(9)
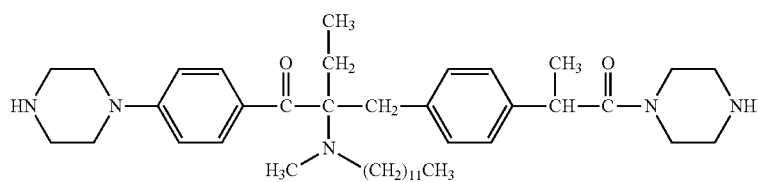
(10)
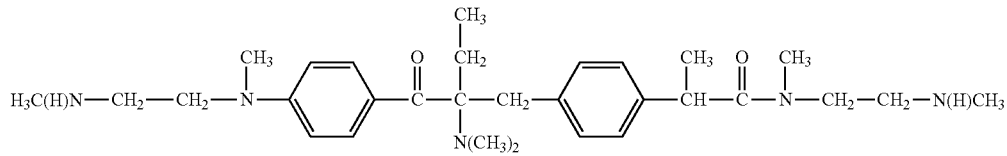
(11)
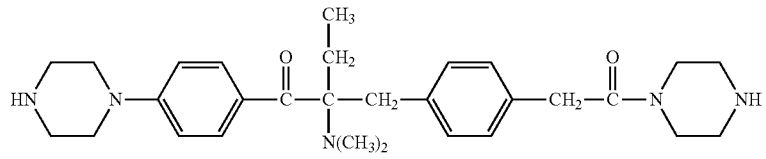
(12)
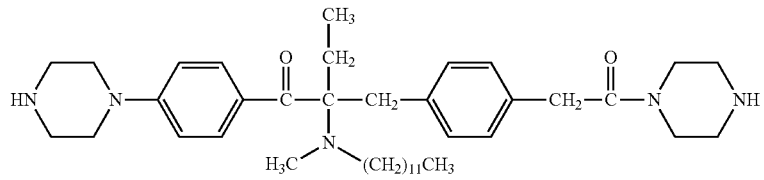
(13)
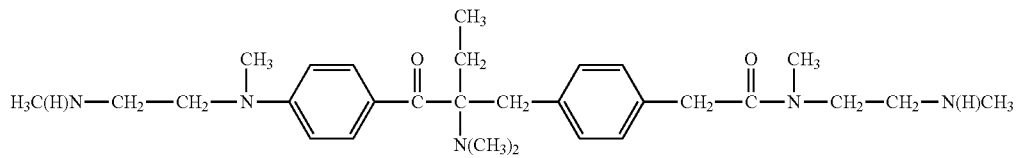
(14)
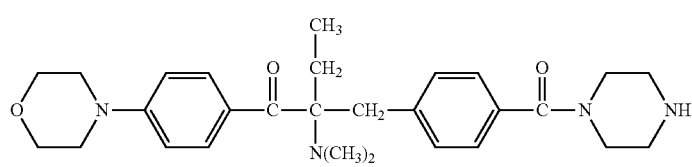

(15)
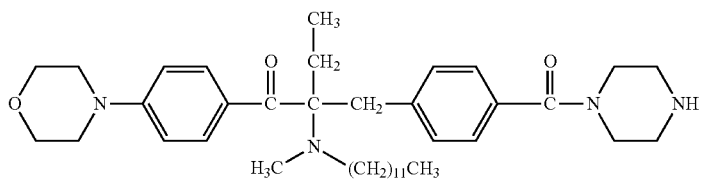
(16)
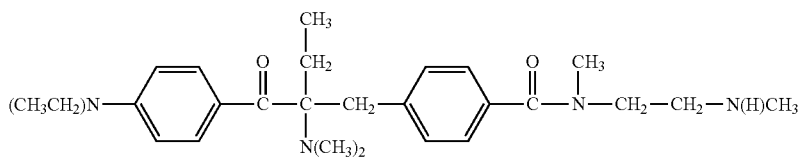
(17)
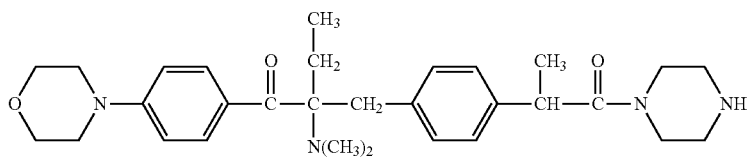
(18)
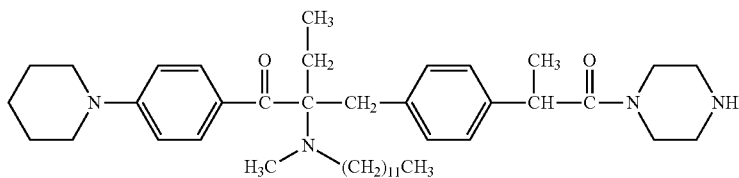
(19)
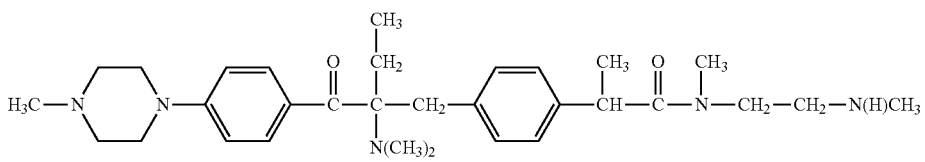
(20)
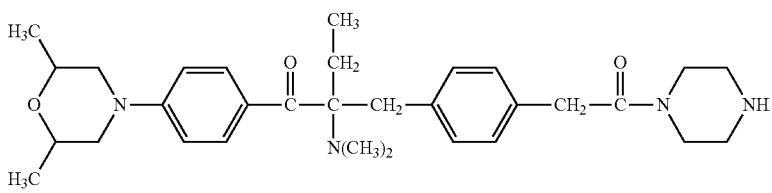
(21)
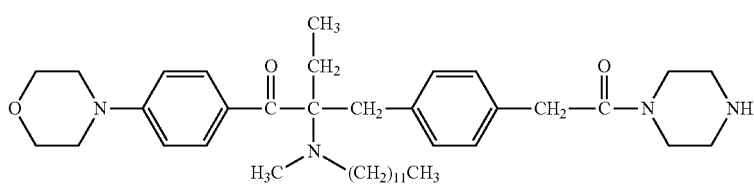
(22)
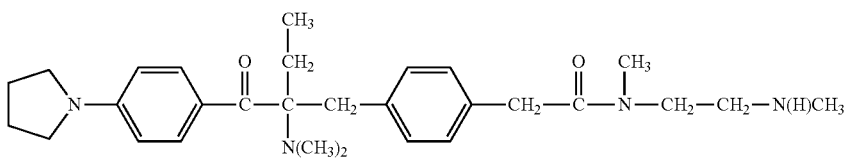
(23)
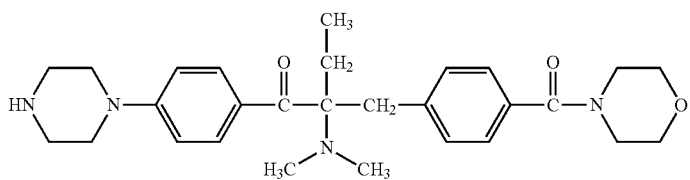

-continued

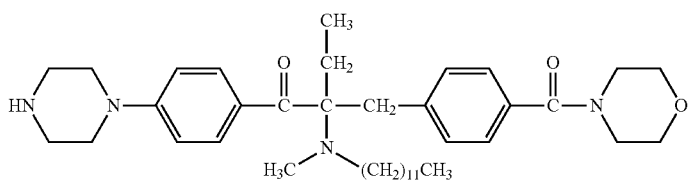
(24)

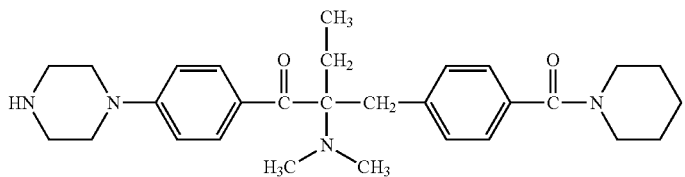
(25)

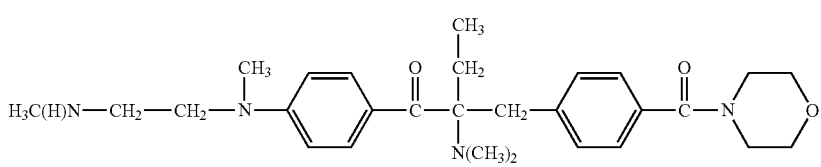
(26)

5. A compound represented by a general formula (1'):

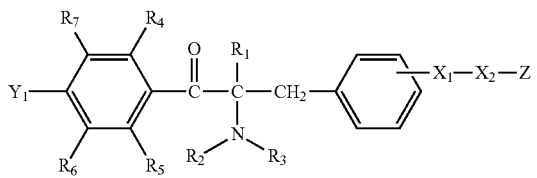
General Formula (1')

wherein R₁ represents an aliphatic group or an aryl group,

R₂ to R₃ each independently represent an aliphatic group or an aryl group,

R₂ and R₃ may together form a ring,

R₄ to R₇ each independently represent a hydrogen atom, an aliphatic group or an optionally substituted aryl group, X₁ represents a single bond or a linear or branched alkylene group having 1 to 6 carbon atoms, X₂ represents a carbonyl group or a thiocarbonyl group, Y₁ represents a group represented by a general formula (2'), a general formula (3') or a general formula (4'), and Z represents a hydroxyl group or a thiol group;

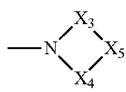
General Formula (2')

wherein X₃ to X₄ each independently represent a linear or branched alkylene or oxyalkylene group having 2 to 6 carbon atoms, and X₅ represents —O— or —NH—;

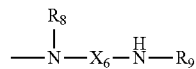
General Formula (3')

wherein X₆ represents a substituted or unsubstituted, linear or branched alkylene or oxyalkylene group having 2 to 6 carbon atoms, and R₈ and R₉ each independently represent an aliphatic group or an aryl group; and

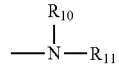
General Formula (4')

wherein R₁₀ and R₁₁ each independently represent an aliphatic group or an aryl group.

6. The compound according to claim 5, wherein the compound represented by the general formula (1') (hereinafter this is abbreviated as "compound (A)") is a compound represented by any of the following structural formula (5') to (15'):

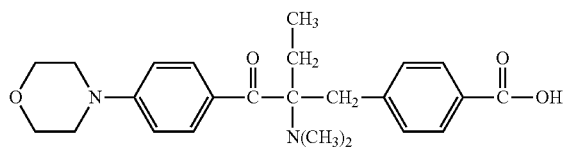
(5')

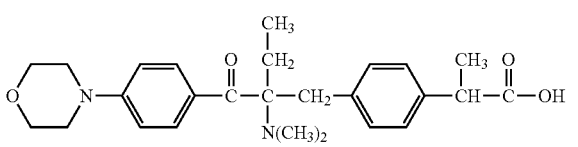
(6')

-continued

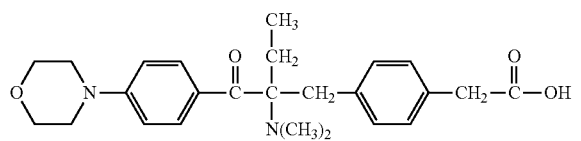
(7')

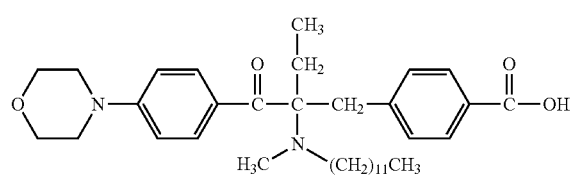
(8')

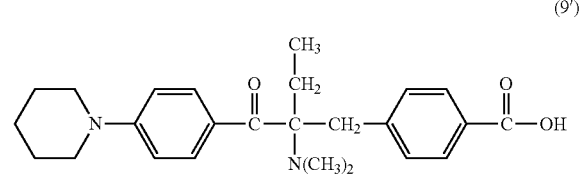
(9')

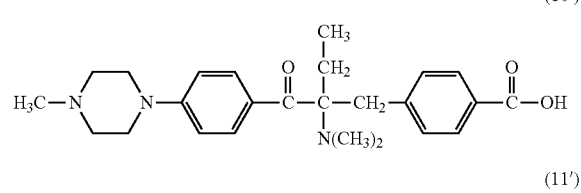
(10')

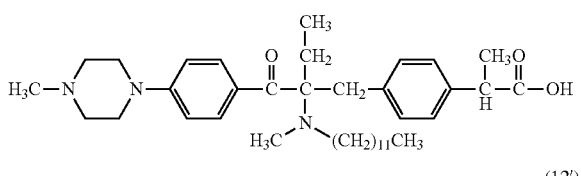
(11')

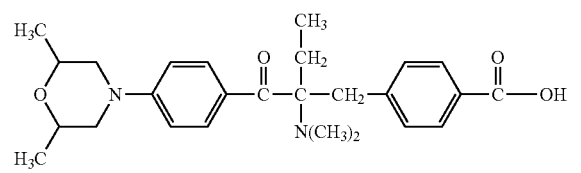
(12')

-continued

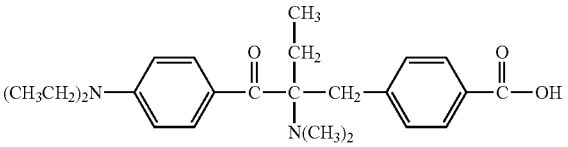
(13')

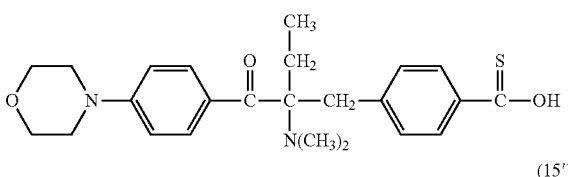
(14')

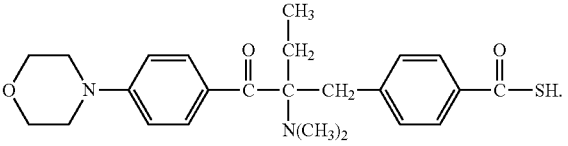
(15')

7. A compound having polymerization initiation performance, which is obtained through reaction of the compound (A) of claim 6 and a compound (B) capable of reacting with the compound (A).

8. The compound according to claim 7, wherein the compound (B) having a functional group reactive with the amino group in the compound or a functional group reactive with the structural moiety represented by:

—X$_2$—Z, in the general formula (1') is a hydroxyl group-containing (meth)acrylate compound.

9. A photopolymerization initiator comprising the compound of claim 1.

10. An active energy ray curable composition comprising the photopolymerization initiator of claim 9.

11. A cured product produced by curing the active energy ray curable composition of claim 10.

12. An active energy ray curable printing ink comprising the active energy ray curable composition of claim 10.

13. An active energy ray curable inkjet recording ink comprising the active energy ray curable composition of claim 10.

* * * * *